(12) United States Patent
Miyamoto et al.

(10) Patent No.: US 11,052,154 B2
(45) Date of Patent: *Jul. 6, 2021

(54) RAS PROTEIN DEGRADATION INDUCING MOLECULE AND PHARMACEUTICAL COMPOSITION

(71) Applicant: Tokyo University of Science Foundation, Tokyo (JP)

(72) Inventors: Etsuko Miyamoto, Tokyo (JP); Masaaki Ozawa, Tokyo (JP)

(73) Assignee: Tokyo University of Science Foundation, Tokyo (JP)

( * ) Notice: Subject to any disclaimer, the term of this patent is extended or adjusted under 35 U.S.C. 154(b) by 194 days.

This patent is subject to a terminal disclaimer.

(21) Appl. No.: 16/349,689

(22) PCT Filed: Nov. 13, 2017

(86) PCT No.: PCT/JP2017/040779
§ 371 (c)(1),
(2) Date: Aug. 28, 2019

(87) PCT Pub. No.: WO2018/092723
PCT Pub. Date: May 24, 2018

(65) Prior Publication Data
US 2020/0000927 A1    Jan. 2, 2020

(30) Foreign Application Priority Data
Nov. 15, 2016 (JP) .............................. JP2016-222683

(51) Int. Cl.
*A61K 47/54* (2017.01)
*A61P 35/00* (2006.01)
*A61K 38/05* (2006.01)

(52) U.S. Cl.
CPC ............ *A61K 47/545* (2017.08); *A61K 38/05* (2013.01); *A61P 35/00* (2018.01)

(58) Field of Classification Search
CPC .. A61K 38/00; C07D 239/49; C07K 14/4703; C07K 2319/70; C07K 2319/95; C07K 5/00; C12P 21/06; C12Q 1/02; G01N 2500/02; G01N 2500/10; C12N 9/00; C12N 9/6427
See application file for complete search history.

(56) References Cited

U.S. PATENT DOCUMENTS

| | | | |
|---|---|---|---|
| 5,882,941 A | 3/1999 | Essigmann et al. | |
| 7,208,157 B2 | 4/2007 | Dashaies et al. | |
| 2009/0270439 A1 | 10/2009 | Ohyagi | |
| 2010/0074908 A1 | 3/2010 | Solomon et al. | |
| 2012/0115232 A1 | 5/2012 | Kanemaki et al. | |
| 2013/0190340 A1 | 7/2013 | Hedstrom et al. | |
| 2016/0264627 A1 | 9/2016 | Henning et al. | |
| 2018/0164289 A1 | 6/2018 | Miyamoto et al. | |

FOREIGN PATENT DOCUMENTS

| | | |
|---|---|---|
| CN | 103153335 A | 6/2013 |
| EP | 3542821 A1 | 9/2019 |
| EP | 3543349 A1 | 9/2019 |
| JP | 2008-081508 A | 4/2008 |
| JP | 2008-533986 A | 8/2008 |
| JP | 2009-149524 A | 7/2009 |
| JP | 2013056837 | 3/2013 |
| JP | 2013-177444 A | 9/2013 |
| WO | WO00/45165 A1 | 8/2000 |
| WO | WO2008/147536 A1 | 12/2008 |
| WO | WO2012/003281 | 1/2012 |
| WO | WO2013/106643 A2 | 7/2013 |
| WO | WO2016204197 | 12/2016 |

OTHER PUBLICATIONS

Psahoulia et al. Carcinogenesis (2007) 28(5): 1021-1031). (Year: 2007).*
Office Action issued in the related CN Patent Application No. CN201680048166.8, dated Jul. 22, 2020.
I.N. Lavrik et al: "Caspases: pharmacological manipulation of cell death", Journal of Clinical Investigation, vol. 115, No. 10, Oct. 1, 2005 (Oct. 1, 2005), pp. 2665-2672, XP055522159.
J.T. Nguyen: "Direct activation of the apoptosis machinery as a mechanism to target cancer cells", Proceedings of the National Academy of Sciences, vol. 100, No. 13, Jun. 16, 2003 (Jun. 16, 2003), pp. 7533-7538, XP055072593.
Niki Chondrogianni et al: "Proteasome activation delays aging in vitro and in vivo", Free Radical Biology and Medicine, vol. 71, Jun. 1, 2014 (Jun. 1, 2014), pp. 303-320, XP055361652.
Florian Lienert et al: "Synthetic biology in mammalian cells: next generation research tools and therapeutics", Nature Reviews Molecular Cell Biology, vol. 15, No. 2, Jan. 17, 2014 (Jan. 17, 2014), pp. 95-107, XP055206837.
Neklesa, T.K., et al., "Greasy tags for protein removal.", Nature, 2012, 487, 308-309.
Cabrol et al. PLoS One (2009) 4(4): e5724, pp. 1-8 (Year: 2009).
Lee et al. Nature (2010) 467: 179-188 (Year: 2010).
Office Action (Restriction requirement) issued in the U.S. Appl. No. 15/736,089, dated Nov. 26, 2019.
Shi et al. abstract from Federation Am. Soc. Exp. Biology Journal (FASEB Journal) (Apr. 1, 2015) vol. 29(1, supplement) (Year:2015).
Office Action issued in the U.S. Appl. No. 15/736,089, dated May 1, 2020.

(Continued)

*Primary Examiner* — Susan M Hanley
(74) *Attorney, Agent, or Firm* — Pearl Cohen Zedek Latzer Baratz LLP

(57) ABSTRACT

A Ras protein degradation inducing molecule that can induce degradation of Ras proteins, and a pharmaceutical composition that contains this Ras protein degradation inducing molecule are provided. The Ras protein degradation inducing molecule is a conjugate of a Ras protein affinity molecule which has affinity to Ras proteins, and a proteolysis-inducing tag which has affinity to protease and does not inhibit proteolysis of proteins by the protease.

9 Claims, 15 Drawing Sheets
Specification includes a Sequence Listing.

(56) References Cited

OTHER PUBLICATIONS

Bell, S. et al., p. 53 Contains Large Unstructured Regions in its Native State, J Mol Biol, 2002, vol. 322, pp. 917-927, ISSN 0022-2836.

Weisi Wang et al.: "Small molecule agents targeting the p53-MDM2 pathway for cancer therapy", Medicinal Research Reviews, vol. 32, No. 6, Nov. 16, 2012 (Nov. 16, 2012), pp. 1159-1196, XP055115939, ISSN; 0198-6325, DOI: 10. 1002/med.20236.

Yoshikazu Johmura et al.: "SCFFbxo22-KDM4A targets methylated p53 for degradation and regulates senescence", Nature Communications, vol. 7, No. 1, Feb. 12, 2016 (Feb. 12, 2016), XP055686014, DOI: 10.1038/ncomms10574.

Extended European Search Report issued in the EP Patent Application No. 17871163.6, dated Apr. 24, 2020.

"Invitation pursuant to Rule 62a(1) EPC and Rule 63(1) EPC" issued in the EP Patent Application No. EP16811671.3, dated Nov. 20, 2018.

Long, M.J. et al., Inhibitor Mediated Protein Degradation, Chem Biol, 2012, vol. 19, p. 629-37, ISSN 1074-5521.

Shi, Y. et al., Boc3Arg-Linked Ligands Induce Degradation by Localizing Target Proteins to the 20S Proteasome, ACS Chem Biol, 2016.10.05, vol. 11, p. 3328-37, ISSN 1554-8937.

Itoh, Y. et al., "Development of target protein-selective degradation inducer for protein knockdown", Bioorg. Med. Chem., 2011, 19, 3229-3241.

Demizu, Y. et al., "Design and synthesis of estrogen receptor degradation inducer based on a protein knockdown strategy.", Bioorg. Med. Chem. Lett., 2012, 15, 1793-1796.

Hines, J. et al., "Posttranslational protein knockdown coupled to receptor tyrosine kinase activation with phosphoPROTACs.", Proc. Natl. Acad. Sci. U.S.A., 2013, 110(22), 8942-8947.

2012, entire text, Astellas Foundation for Research on Metabolic Disorders non-official translation (INOBE, Tomonao. Molecular Structure of Protein Degradation by Proteasomes, 44th Annual Research Report.).

Kovrigina, E. A. et al., The Ras G Domain Lacks the Intrinsic Propensity to Form Dimers, Biophys J, 2015, vol. 109, pp. 1000-1008, ISSN 0006-3495, Abstract, etc.

Gurung A. B. et al., Significance of Ras Signaling in Cancer and Strategies for its Control. Oncology & Hematology Review, Nov. 23, 2015, vol. 11, No. 2, pp. 147-152.

Sun Q. et al., Discovery of Small Molecules that Bind to K-Ras and Inhibit Sos-Mediated Activation. Angew Chem Int Ed Engl, May 8, 2012, vol. 51, No. 25, pp. 6140-6143.

Office Action issued in the corresponding SG Patent Application No. SG11201904296R, dated Oct. 1, 2020.

Zhi Tan et al.: "Past, Present, and Future of Targeting Ras for Cancer Therapies", Mini Reviews in Medicinal Chemistry, vol. 16, No. 5, Feb. 1, 2016 (Feb. 1, 2016), p. 345-357, XP55731807.

Extended European Search Report issued in the corresponding EP Patent Application No. EP17870778.2, dated Oct. 5, 2020.

Pullarkat et al. Hemoglobin (2014) 38(3): 188-195 (Year: 2014).

Shkedy et al. FEBS Left. (1994) 348: 126-130 (Year: 1994).

Office Action issued in the related U.S. Appl. No. 16/349,708, dated Oct. 27, 2020.

Taavi K Neklesa et al. "Small-molecule hydrophobic tagging-induced degradation of halotab fusion proteins", Nature Chemical Biology, Jul. 3, 2011, vol. 7, p. 538-543.

Office Action issued in the CN Patent Application No. CN201680048166.8, dated Jan. 14, 2021.

* cited by examiner

HeLa (K-Ras-WT)

SW1990 (K-Ras-G12D)

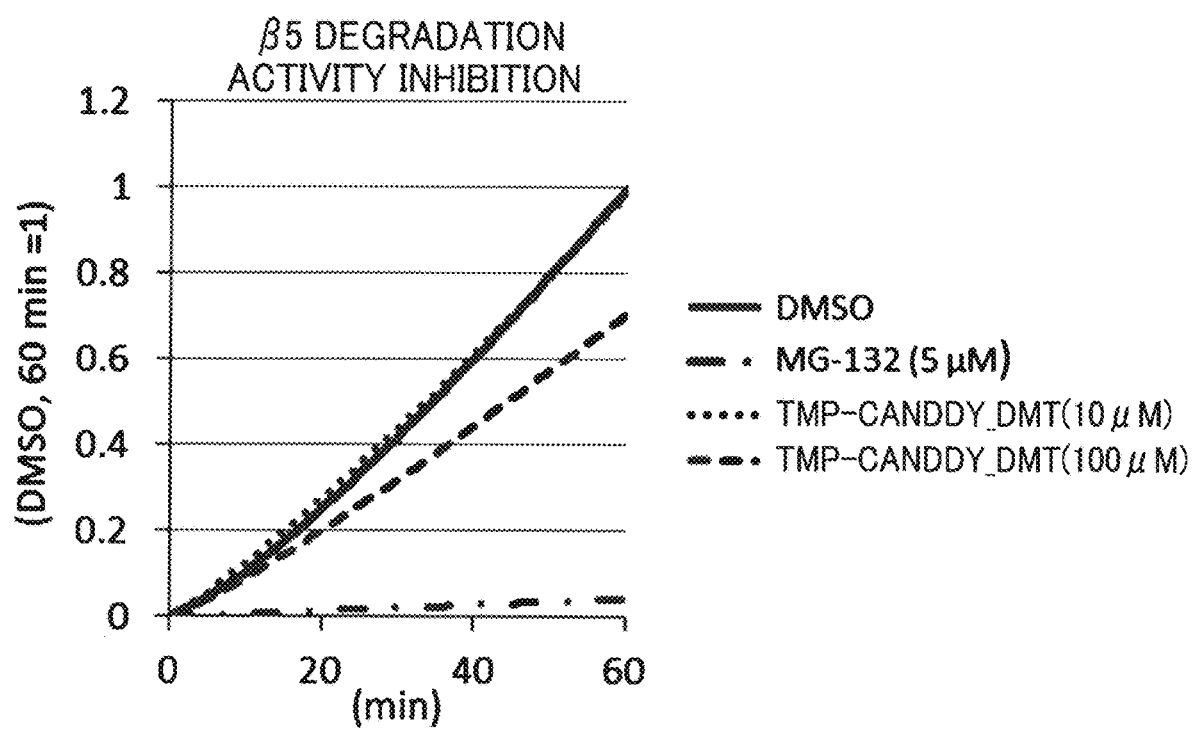

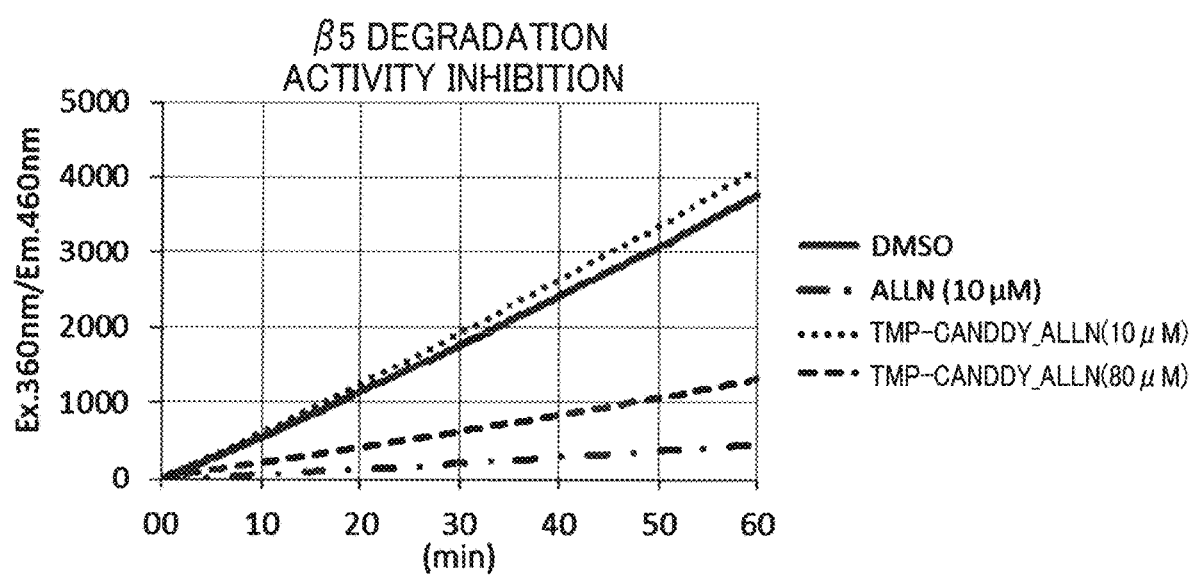

RAS PROTEIN DEGRADATION INDUCING MOLECULE AND PHARMACEUTICAL COMPOSITION

CROSS-REFERENCE TO RELATED APPLICATIONS

This application is a National Phase Application of PCT International Application No. PCT/JP2017/040779, International Filing Date Nov. 13, 2017, claiming priority to and benefit of Japanese Patent Application No. 2016-222683, filed Nov. 15, 2016, which are hereby all incorporated by reference in their entireties.

TECHNICAL FIELD

The present disclosure relates to a Ras protein-degradation inducing molecule and a pharmaceutical composition.

BACKGROUND ART

A Ras protein is a type of a low molecule GTP (Guanosine triphosphate)-binding protein, and has isoforms such as a K-Ras protein, an H-Ras protein, and an N-Ras protein. The Ras protein functions in mediating signals, such as for cell proliferation, differentiation, and adhesion by various extracellular stimuli, from upstream receptor tyrosine kinases to downstream effectors.

The Ras protein regulates cell proliferation and the like by transition between the active form bound to GTP (Ras/GTP) and the inactive form bound to GDP (Guanosine diphosphate) (Ras/GDP). On the other hand, it is known that in human cancers, the Ras protein is mutated at high frequency, and due to this mutation, the Ras protein is permanently the active form. For example, mutations in the Ras protein has been identified in about 95% of pancreatic cancers, about 45% of colorectal cancers, and about 35% of lung cancers. Thus, the Ras protein has attracted attention as the most promising molecular target in the development of anticancer agents.

However, the binding of Ras protein to GTP is very strong, and there are few pockets on the surface of the Ras protein into which an inhibitor can enter. Therefore, the Ras protein is still considered to be difficult target (undruggable target) for drug discovery. The development of a farnesyl transferase inhibitor that target post-translational modifications of Ras protein rather than the Ras protein itselves has been performed, but such development has been unsuccessful.

Thus, in recent years, methodologies have been developed to reduce the amount of the Ras protein (expression) instead of inhibiting the function of the Ras protein.

As a technique for controlling the amount of a target protein at the RNA level, known is the RNAi (RNA interference) technique in which mRNA of the target protein is degraded with siRNA (small interfering RNA).

Furthermore, as a technique for controlling the amount of a target protein at the protein level, known is a technique using a complex obtained by linking a molecule that binds to the target protein and a molecule that binds to a ubiquitin ligase (E3) (see, for example, Patent Documents 1 to 2, and non-Patent Documents 1 to 3). This technique binds a target protein to a ubiquitin ligase via the complex and specifically ubiquitinates the target protein, leading to degradation by a proteasome. The complex may be referred to as SNIPER (Specific and Nongenetic IAP-dependent Protein ERaser), PROTAC (PROteolysis TArgeting Chimera), etc.

Patent Document 1: Japanese Unexamined Patent Application, Publication No. H2013-056837
Patent Document 2: U.S. Pat. No. 7,208,157, Specification
Non-Patent Document 1: Itoh, Y. et al., "Development of target protein-selective degradation inducer for protein knockdown.", Bioorg. Med. Chem., 2011, 19, 3229-3241
Non-Patent Document 2: Demizu, Y. et al., "Design and synthesis of estrogen receptor degradation inducer based on a protein knockdown strategy.", Bioorg. Med. Chem. Lett., 2012, 15, 1793-1796
Non-Patent Document 3: Hines, J. et al., "Posttranslational protein knockdown coupled to receptor tyrosine kinase activation with phosphoPROTACs.", Proc. Natl. Acad. Sci. U.S.A., 2013, 110(22), 8942-8947

DISCLOSURE OF THE INVENTION

Problems to be Solved by the Invention

However, the RNAi technique suffers from off-target effects, and thus the amount of a target protein is difficult to be controlled in a specific manner. Further, the RNAi technique has been challenged in terms of the delivery of siRNA, and many problems need to be solved for applying to medicine.

On the other hand, the technique using a complex obtained by linking a molecule that binds to a target protein and a molecule that binds to a ubiquitin ligase is easier to be applied to medicine than the RNAi technique. However, it is known that mono-ubiquitination of the Ras protein increases their binding to GTP and also increases their affinity with downstream effectors (Sasaki, A. T. et al., 2011, Sci. Signal., 4, ra13). Therefore, there is a concern that the process of specifically ubiquitinating the Ras protein, leading to degradation by a proteasome, may promote carcinogenesis.

In addition, the method for ubiquitinating the target protein has the following problems.
(1) There are many types of ubiquitin ligases. The ubiquitin ligases have target specificity. Accordingly, in order to ubiquitinate an individual specific target protein, it is necessary to address the protein individually; for example, it is necessary to design the molecule in accordance with the target protein.
(2) It is difficult to control a ubiquitinated signal. For example, ubiquitination of proteins is known to be associated with signals such as differentiation and carcinogenesis, in addition to degradation of proteins. It is also known that ubiquitination of proteins has tissue specificity and time specificity. Thus, it is presumed that ubiquitination of a target protein may be not a signal for degradation of the target protein but another signal.
(3) Ubiquitin or ubiquitinating enzyme may be defective. For example, there are cases where the ubiquitin or the ubiquitinating enzyme does not function normally (malfunctions) due to mutation or the like, which is often a cause of diseases. Thus, in some cases, it is assumed that ubiquitination of the target protein does not induce degradation of the target protein.

In view of the above circumstances, an object of the present disclosure is to provide a Ras protein-degradation inducing molecule capable of inducing degradation of a Ras protein, and a pharmaceutical composition including the Ras protein-degradation inducing molecule.

Means for Solving the Problems

Specific means for achieving the above object include the following embodiments.

<1> A Ras protein-degradation inducing molecule being a conjugate of a Ras protein affinity molecule that has an affinity with a Ras protein, and a protein-degradation inducing tag that has an affinity with a protease and does not inhibit degradation of a protein by the protease; and being capable of inducing degradation of a Ras protein.

<2> The Ras protein-degradation inducing molecule according to <1>, in which the Ras protein-degradation inducing molecule is capable of inducing degradation of the Ras protein in a ubiquitin-independent manner.

<3> The Ras protein-degradation inducing molecule according to <1> or <2>, in which the protein-degradation inducing tag has a structure where a protease inhibitory activity of a protease inhibitor is inactivated.

<4> The Ras protein-degradation inducing molecule according to any one of <1> to <3>, in which the protease is a proteasome.

<5> The Ras protein-degradation inducing molecule according to <4>, in which the protein-degradation inducing tag has a structure where a proteasome inhibitory activity of a proteasome inhibitor is inactivated.

<6> The Ras protein-degradation inducing molecule according to <5>, in which the proteasome inhibitory activity is an inhibitory activity against at least one selected from a caspase-like activity, a trypsin-like activity, and a chymotrypsin-like activity.

<7> A pharmaceutical composition including the Ras protein-degradation inducing molecule according to any one of <1> to <6>.

<8> The pharmaceutical composition according to <7>, in which the pharmaceutical composition is used for preventing or treating a Ras protein-mediated disease or condition.

<9> The pharmaceutical composition according to <8>, in which the Ras protein-mediated disease or condition is a cancer, an immune disease, an infection, a neurological disease, a RAS/MAPK syndrome, cirrhosis, chronic hepatitis, or a memory impairment.

<10> The pharmaceutical composition according to <9>, in which the Ras protein-mediated disease or condition is a cancer.

Effects of the Invention

The present disclosure can provide a Ras protein-degradation inducing molecule capable of inducing degradation of a Ras protein, and a pharmaceutical composition including the Ras protein-degradation inducing molecule.

BRIEF DESCRIPTION OF THE DRAWINGS

FIG. 10C shows inhibitory activity of TMP-CANDDY_DMT, and MG-132 with respect to a catalytic subunit β5 of the proteasome.

FIG. 13C shows inhibitory activity of TMP-CANDDY_ALLN and ALLN with respect to the catalytic subunit β5 of the proteasome.

PREFERRED MODE FOR CARRYING OUT THE INVENTION

Figure 1:
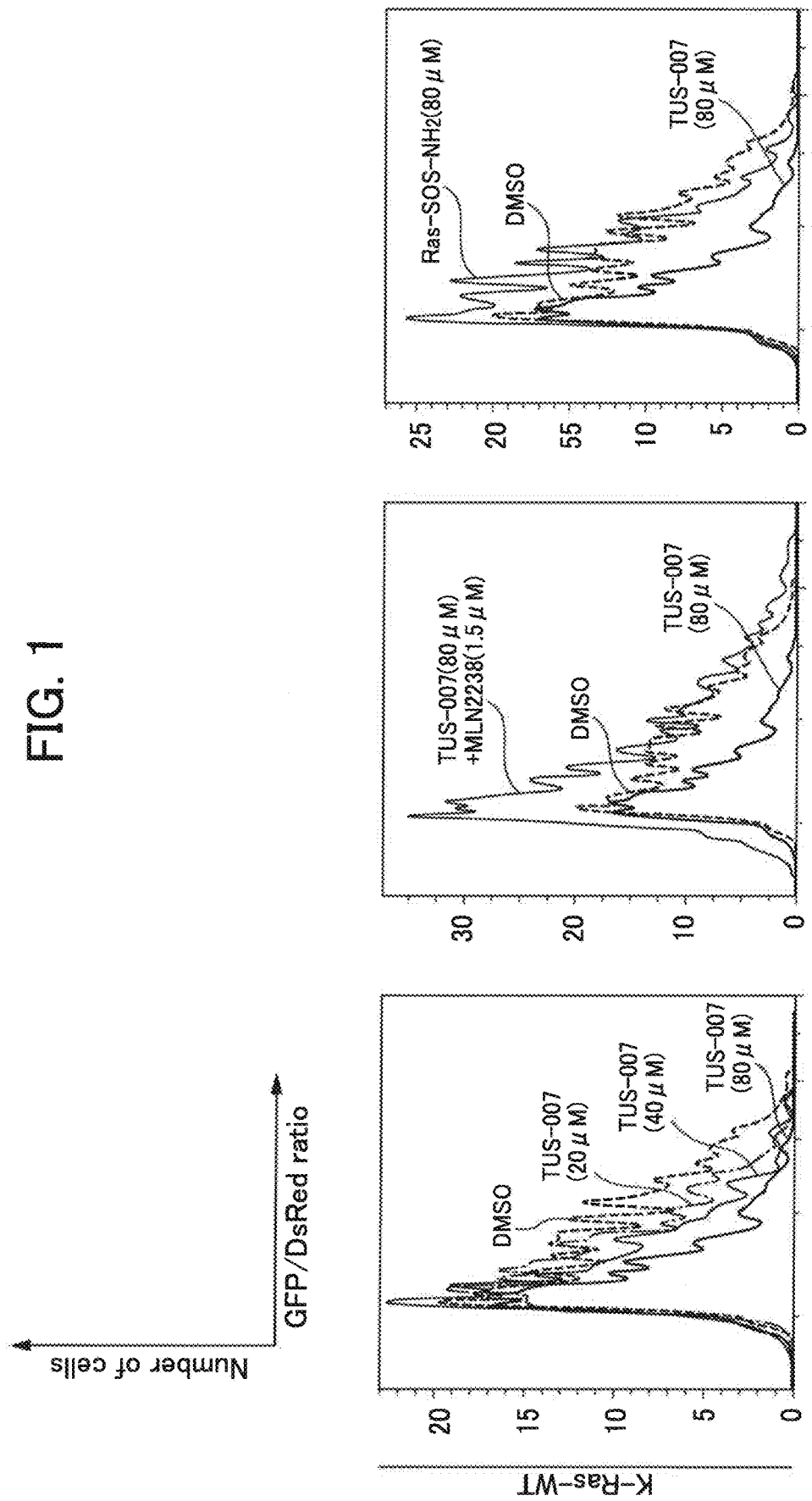
FIG. 1 shows the results of evaluation by FACS (Fluorescence Activated Cell Sorting) analysis of degradation (knockdown) of a wild-type K-Ras protein forcibly expressed in HeLa cells through TUS-007.

Below, the embodiments of the present invention will be described in detail. However, the present invention shall not be limited to the following embodiments.

A range of numerical values specified using "-" as used herein refers to a range including values indicated before and after "-" as the minimum value and the maximum value, respectively. Amino acids as used herein are denoted by the single letter notation (for example, "G" for glycine) or the three-letter notation (for example, "Gly" for glycine) as is well known in the art.

<Ras Protein-Degradation Inducing Molecule>

A Ras protein-degradation inducing molecule of the present disclosure is a conjugate of a Ras protein affinity molecule that has an affinity with a Ras protein and a protein-degradation inducing tag that has an affinity with a protease and does not inhibit degradation of a protein by the protease, and can induce degradation of the Ras protein. The Ras protein-degradation inducing molecule of the present disclosure can lead a Ras protein to degradation (knockdown) by a protease (for example, a proteasome), without ubiquitination of the Ras protein (in other words, in a ubiquitin-independent manner).

It is noted that a polyubiquitin chain such as a tetraubiquitin chain ($Ub_4$) or a ubiquitin-like domain (UbL) is likely to function as a protein-degradation inducing tag. However, when a polyubiquitin chain or a ubiquitin-like domain is used as a protein-degradation inducing tag, the Ras protein is indirectly ubiquitinated via the Ras protein affinity molecule. In the present specification, such an indirect ubiquitination of the Ras protein is also included in the ubiquitination of the Ras protein.

(Ras Protein Affinity Molecule)

The Ras protein affinity molecule constituting the Ras protein-degradation inducing molecule of the present disclosure is a molecule having an affinity with the Ras protein.

The Ras protein has isoforms such as a K-Ras protein, an H-Ras protein, and an N-Ras protein, and may be any isoform. Furthermore, the Ras protein may be a wild-type or a mutant. Examples of the mutant K-Ras protein and N-Ras protein include a G12D mutant (a mutant in which glycine (G) that is an amino acid residue at the 12th position from the N-terminal is changed to aspartic acid (D); the same is true hereinafter), a G12V mutant, a G12S mutant, a G12C mutant, a G13D mutant, a G13V mutant, a G13S mutant, a G13C mutant, an A59T mutant, an A59G mutant, a Q61K mutant, a Q61E mutant, a Q61H mutant, a K117N mutant, an A146T mutant, an A146P mutant, an A146V mutant, and the like. Examples of the mutant H-Ras protein include a T35S mutant, and the like.

The Ras protein regulates cell proliferation and the like by transition between the active form bound to GTP and the inactive form bound to GDP. On the other hand, it is known that in human cancers, the Ras protein is mutated at high frequency, and due to this mutation, the Ras protein is permanently the active form. Thus, the examples of the preferable Ras protein affinity molecule include one having an affinity with a mutant Ras protein that has been mutated to the active form. When the Ras protein affinity molecule has an affinity with the mutant Ras protein that has been mutated to the active form, this mutant Ras protein can be led to degradation (knockdown) by a protease (for example, a proteasome).

As used herein, the phrase "having an affinity with the Ras protein" means, for example, the capability of binding to the Ras protein via a covalent bond, a hydrogen bond, a hydrophobic bond, Van der Waals force, and the like. When the interaction between the other molecules that have been known to interact with the Ras protein (proteins, peptides, antibodies, DNA, RNA, metabolites, low molecular weight compounds, and the like) and the Ras protein is influenced by a certain molecule in a concentration dependent manner, it can be determined that the molecule has an affinity with the Ras protein.

Examples of the Ras protein affinity molecule include low molecular weight compounds, natural products, peptides, antibodies, and the like. It is noted that in the present disclosure, the antibody includes a fragment including a variable site of the antibody, for example, a Fab fragment or a F(ab') fragment of Ig (immunoglobulin), in addition to anIg having two H-chains and two L-chains. Preferably, the Ras protein affinity molecule has a molecular weight within the range of, for example, 50 to 5000 for low molecular weight compounds.

A structure of the Ras protein affinity molecule is not particularly limited as long as it has an affinity with the Ras protein. As the Ras protein affinity molecule, for example, a Ras inhibitor having an affinity with the Ras protein can be used. Furthermore, the Ras protein affinity molecule can also be obtained by screening from candidate molecules.

Examples of the Ras protein affinity molecules are shown in the following Tables 1 to 8. However, Ras protein affinity molecules that can be used for the Ras protein-degradation inducing molecule of the present disclosure are not particularly limited thereto. Existing data bases (Binding DB (bindingdb.org/bind/index.jsp), PCI DB (tanpaku.org/pci/pci_home.html), ProtChemSl (russelllab.org/) and the like) can be consulted for information about Ras protein affinity molecules if needed.

TABLE 1

| No. | Name | Structural formula | Molecular weight | Target | Published paper |
|---|---|---|---|---|---|
| 1 | SCH-53239 | | 535.58 | •Ras/GDP | Bioorg. Med. Chem. 1997, vol 5, pp 125-133. |

TABLE 1-continued

| No. | Name | Structural formula | Molecular weight | Target | Published paper |
|---|---|---|---|---|---|
| 2 | SCH-53870 | | 358.41 | •Ras/GDP | Bioorg. Med. Chem. 1997, vol 5, pp 125-133. |
| 3 | SCH-54292 | | 520.55 | •Ras/GDP | Bioorg. Med. Chem. 1997, vol 5, pp 125-133. |
| 4 | SCH-54341 | | 276.31 | •Ras/GDP | Biochemistry 1998, vol 37, pp 15631-15637. |
| 5 | SCH-56407 | | 482.00 | •Ras/GDP | Biochemistry 1998, vol 37, pp 15631-15637. |
| 6 | Compound 1 | | 540.63 | •Ras/GDP | ChemBioChem 2005, vol 6, pp 1839-1848. |

(Table 2)

TABLE 2

| No. | Name | Structural formula | Molecular weight | Target | Published paper |
|---|---|---|---|---|---|
| 7 | Compound 2 | | 540.63 | Ras/GDP | ChemBioChem 2005, vol 6, pp 1839-1848. |
| 8 | Compound 3 | | 504.58 | Ras/GDP | ChemBioChem 2005, vol 6, pp 1839-1848. |
| 9 | Compound 4 | | 504.58 | Ras/GDP | ChemBioChem 2005, vol 6, pp 1839-1848. |

TABLE 2-continued

| No. | Name | Structural formula | Molecular weight | Target | Published paper |
|---|---|---|---|---|---|
| 10 | DCIE | | 257.16 | Wild-type Ras/GDP Ras-R41S/GDP Ras-G12D/GDP | PNAS 2012, vol 109, pp 5299-5304. |
| 11 | DCAI | | 243.13 | Wild-type Ras/GDP Ras-R41S/GDP Ras-G12D/GDP | PNAS 2012, vol 109, pp 5299-5304. |
| 12 | Compound 1 | | 261.33 | Wild-type K-Ras/GDP Wild-type H-Ras/GDP K-Ras-G12V/GDP K-Ras-G12D/GDP | Angew. Chem. Int.. Ed. 2012, vol 51, pp 6140-6143. |
| 13 | Compound 2 | | 207.29 | Wild-type K-Ras/GDP Wild-type H-Ras/GDP K-Ras-G12V/GDP K-Ras-G12D/GDP | Angew. Chem. Int. Ed. 2012, vol 51, pp 6140-6143. |

TABLE 3

| No. | Name | Structural formula | Molecular weight | Target | Published paper |
|---|---|---|---|---|---|
| 14 | Compound 3 | | 263.31 | Wild-type K-Ras/GDP Wild-type H-Ras/GDP K-Ras-G12V/GDP K-Ras-G12D/GDP | Angew. Chem. Int. Ed. 2012, vol 51, pp 6140-6143. |
| 15 | Compound 4 | | 248.29 | Wild-type K-Ras/GDP Wild-type H-Ras/GDP K-Ras-G12V/GDP K-Ras-G12D/GDP | Angew. Chem. Int. Ed. 2012, vol 51, pp 6140-6143. |

TABLE 3-continued

| No. | Name | Structural formula | Molecular weight | Target | Published paper |
|---|---|---|---|---|---|
| 16 | Compound 5 | | 260.36 | Wild-type K-Ras/GDP Wild-type H-Ras/GDP K-Ras-G12V/GDP K-Ras-G12D/GDP | Angew. Chem. Int. Ed. 2012, vol 51, pp 6140-6143. |
| 17 | Compound 6 | | 267.28 | Wild-type K-Ras/GDP Wild-type H-Ras/GDP K-Ras-G12V/GDP K-Ras-G12D/GDP | Angew. Chem. Int. Ed. 2012, vol 51, pp 6140-6143. |
| 18 | Compound 8 | | 319.27 | Wild-type K-Ras/GDP Wild-type H-Ras/GDP K-Ras-G12V/GDP K-Ras-G12D/GDP | Angew. Chem. Int. Ed. 2012, vol 51, pp 6140-6143. |
| 19 | Compound 9 | | 333.40 | Wild-type K-Ras/GDP Wild-type H-Ras/GDP K-Ras-G12V/GDP K-Ras-G12D/GDP | Angew. Chem. Int. Ed. 2012, vol 51, pp 6140-6143. |
| 20 | Compound 10 | | 333.40 | Wild-type K-Ras/GDP Wild-type H-Ras/GDP K-Ras-G12V/GDP K-Ras-G12D/GDP | Angew. Chem. Int. Ed. 2012, vol 51, pp 6140-6143. |
| 21 | Compound 11 | | 361.45 | Wild-type K-Ras/GDP Wild-type H-Ras/GDP K-Ras-G12V/GDP K-Ras-G12D/GDP | Angew. Chem. Int. Ed. 2012, vol 51, pp 6140-6143. |

TABLE 4

| No. | Name | Structural formula | Molecular weight | Target | Published paper |
|---|---|---|---|---|---|
| 22 | Compound 12 | | 375.48 | Wild-type K-Ras/GDP Wild-type H-Ras/GDP K-Ras-G12V/GDP K-Ras-G12D/GDP | Angew. Chem. Int. Ed. 2012, vol 51, pp 6140-6143. |
| 23 | Compound 13 | | 359.43 | Wild-type K-Ras/GDP Wild-type H-Ras/GDP K-Ras-G12V/GDP K-Ras-G12D/GDP | Angew. Chem. Int. Ed. 2012, vol 51, pp 6140-6143. |
| 24 | Kobe0065 | | 449.79 | H-Ras-G12V H-Ras-T35S K-Ras-G12V | PNAS 2013, vol 110, pp 8182-8187. |
| 25 | Kobe2601 | | 351.31 | H-Ras-G12V H-Ras-T35S K-Ras-G12V | PNAS 2013, vol 110, pp 8182-8187. |
| 26 | Kobe2602 | | 419.31 | H-Ras-G12V H-Ras-T35S K-Ras-G12V | PNAS 2013, vol 110, pp 8182-8187. |
| 27 | Andrographolide | | 348.48 | K-Ras-Q61H K-Ras-G12V | PNAS 2013, vol 110, pp 10201-10206. |

TABLE 4-continued
| No. | Name | Structural formula | Molecular weight | Target | Published paper |
|---|---|---|---|---|---|
| 28 | SJR09 | 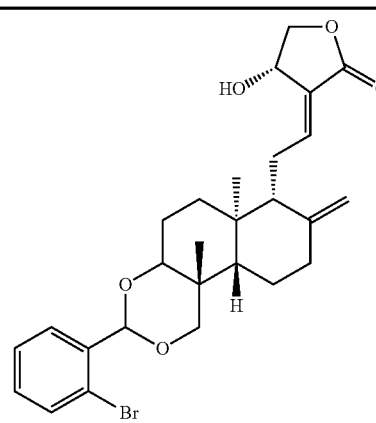 | 517.46 | K-Ras-Q61H K-Ras-G12V | PNAS 2013, vol 110, pp 10201-10206. |
TABLE 5
| No. | Name | Structural formula | Molecular weight | Target | Published paper |
|---|---|---|---|---|---|
| 29 | SJR10 | 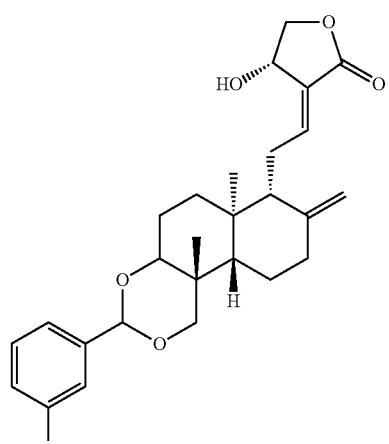 | 517.46 | K-Ras-Q61H K-Ras-G12V | PNAS 2013, vol 110, pp 10201-10206. |
| 30 | SJR23 | 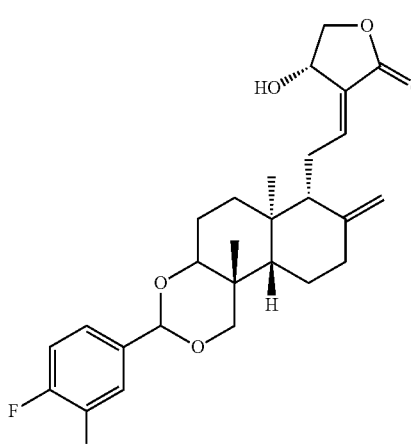 | 491.00 | K-Ras-Q61H K-Ras-G12V | PNAS 2013, vol 110, pp 10201-10206. |

TABLE 5-continued

| No. | Name | Structural formula | Molecular weight | Target | Published paper |
|---|---|---|---|---|---|
| 31 | Bisphenol A | 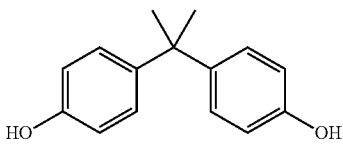 [SMILES: CC(C)(c1ccc(O)cc1)c1ccc(O)cc1] | 228.29 | K-Ras/GDP | J. Med. Chem. 2013, vol 56, pp 9664-9672. |
| 32 | VSA7 | 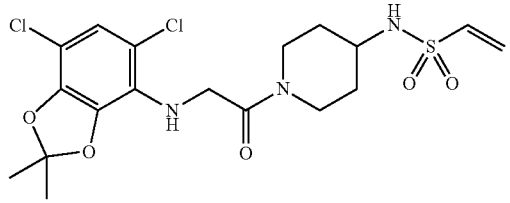 [SMILES: C=CS(=O)(=O)NC1CCN(C(=O)CNc2c(Cl)cc(Cl)c3c2OC(C)(C)O3)CC1] | 464.36 | K-Ras-G12C/GDP | Nature 2013, vol 303, pp 548-551. |
| 33 | VSA8 | 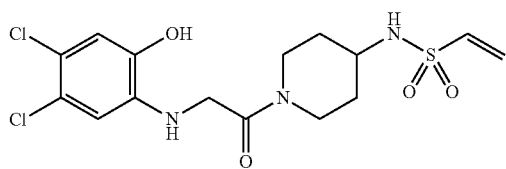 [SMILES: C=CS(=O)(=O)NC1CCN(C(=O)CNc2cc(Cl)c(Cl)cc2O)CC1] | 408.29 | K-Ras-G12C/GDP | Nature 2013, vol 303, pp 548-551. |
| 34 | VSA9 | 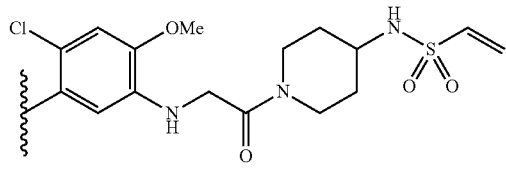 [SMILES: *c1cc(NCC(=O)N2CCC(NS(=O)(=O)C=C)CC2)c(OC)cc1Cl] | 513.78 | K-Ras-G12C/GDP | Nature 2013, vol 303, pp 548-551. |
| 35 | AA10 | 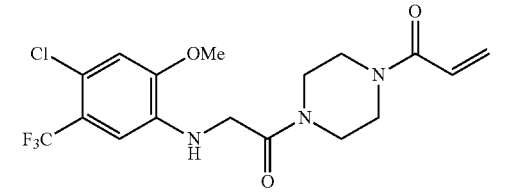 [SMILES: C=CC(=O)N1CCN(C(=O)CNc2cc(C(F)(F)F)c(Cl)cc2OC)CC1] | 405.80 | K-Ras-G12C/GDP | Nature 2013, vol 303, pp 548-551. |

TABLE 6

| No. | Name | Structural formula | Molecular weight | Target | Published paper |
|---|---|---|---|---|---|
| 36 | AA11 | 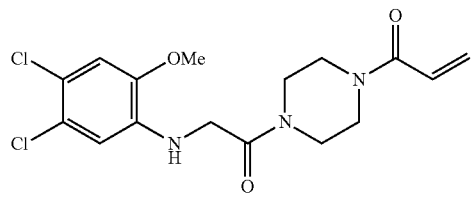 [SMILES: C=CC(=O)N1CCN(C(=O)CNc2cc(Cl)c(Cl)cc2OC)CC1] | 372.25 | K-Ras-G12C/GDP | Nature 2013, vol 303, pp 548-551. |
| 37 | AA12 | 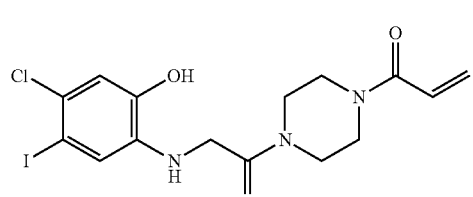 | 449.67 | K-Ras-G12C/GDP | Nature 2013, vol 303, pp 548-551. |

TABLE 6-continued
| No. | Name | Structural formula | Molecular weight | Target | Published paper |
|---|---|---|---|---|---|
| 38 | VSA13 | 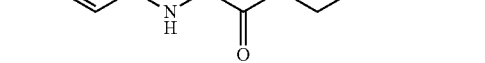 | 392.30 | K-Ras-G12C/GDP | Nature 2013, vol 303, pp 548-551. |
| 39 | VSA14 |  | 393.28 | K-Ras-G12C/GDP | Nature 2013, vol 303, pp 548-551. |
| 40 | VSA15 | 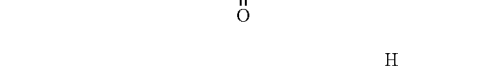 | 450.35 | K-Ras-G12C/GDP | Nature 2013, vol 303, pp 548-551. |
| 41 | AA16 | 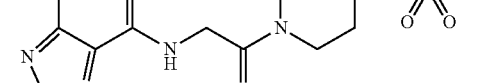 | 343.20 | K-Ras-G12C/GDP | Nature 2013, vol 303, pp 548-551. |
| 42 | SML-8-73-1 | 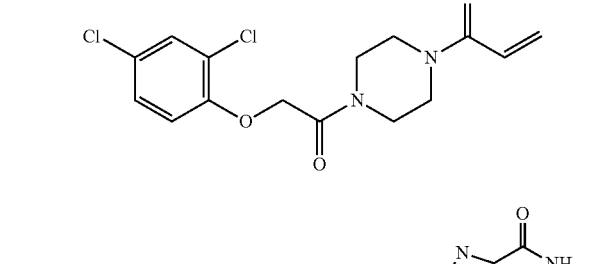 | 562.75 | K-Ras-G12C/GDP | Angew. Chem. Int. Ed. 2014, vol 53, pp 199-204. |
| 43 | SML-10-70-1 | 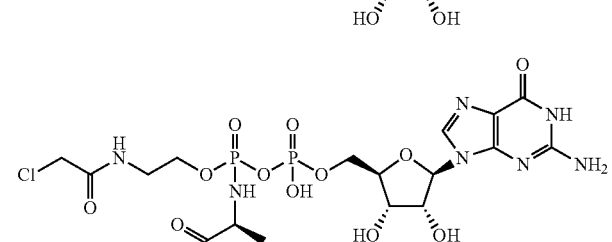 | 764.04 | K-Ras-G12C/GDP | Angew. Chem. Int. Ed. 2014, vol 53, pp 199-204. |
| 44 | ARS853 | 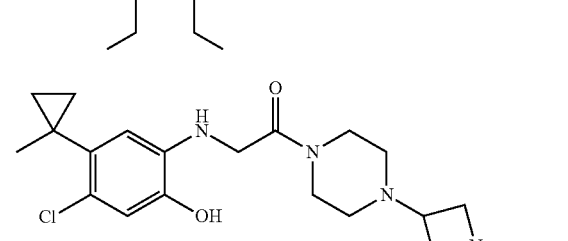 | 432.95 | K-Ras-G12C/GDP | Science 2016, vol 351, pp 604-608. |

TABLE 7

| No. | Name | Structural formula | Molecular weight | Target | Data base |
| --- | --- | --- | --- | --- | --- |
| 45 | BDBM 43263 | | 251.24 | Wild-type Ras | Binding DB (https://www.bindingdb.org/bind/index.jsp) |
| 46 | BDBM 54705 | | 242.27 | Wild-type Ras | Binding DB (https://www.bindingdb.org/bind/index.jsp) |
| 47 | BDBM 54706 | | 216.24 | Wild-type Ras | Binding DB (https://www.bindingdb.org/bind/index.jsp) |
| 48 | BDBM 54678 | | 340.18 | Wild-type Ras | Binding DB (https://www.bindingdb.org/bind/index.jsp) |
| 49 | BDBM 54687 | | 497.57 | Wild-type Ras | Binding DB (https://www.bindingdb.org/bind/index.jsp) |

TABLE 7-continued

| No. | Name | Structural formula | Molecular weight | Target | Data base |
|---|---|---|---|---|---|
| 50 | BDBM 43246 | | 260.24 | Wild-type Ras | Binding DB (https://www.bindingdb.org/bind/index.jsp) |

TABLE 8

| No. | Name | Structural formula | Molecular weight | Target | Data base |
|---|---|---|---|---|---|
| 51 | BDBM 43221 | | 390.47 | Wild-type Ras | Binding DB (https://www.bindingdb.org/bind/index.jsp) |
| 52 | BDBM 43251 | | 295.78 | Wild-type Ras | Binding DB (https://www.bindingdb.org/bind/index.jsp) |
| 53 | Resveratol | | 228.25 | K-Ras H-Ras | PCI DB (http://www.tanpaku.org/pci/pci_home.html) |
| 54 | Curucmin | | 368.38 | K-Ras | PCI DB (http://www.tanpaku.org/pci/pci_home.html) |

TABLE 8-continued

| No. | Name | Structural formula | Molecular weight | Target | Data base |
|---|---|---|---|---|---|
| 55 | AC10A9UT | | 325.34 | H-Ras | ProtChemSI (http://pcidb.russelllab.org/) |

(Protein-degradation inducing tag)

The protein-degradation inducing tag constituting the Ras protein-degradation inducing molecule according to the present disclosure is a molecule having an affinity with a protease and that does not inhibit degradation of a protein by the protease. Below, the above protein-degradation inducing tag may also be referred to as a CiKD (Chemical interaction and KnockDown) tag or a CANDDY (Chemical AffiNities and Degradation Dynamics) tag.

There is no particular limitation for the protease, and any molecule having a protease activity can be used. For example, it may be a protease complex such as a proteasome, or may be a protease other than the proteasome. Alternatively, it may be a portion of a proteasome as long as the portion has a protease activity.

Examples of the proteasome include 26S proteasome, an immunoproteasome, and a thymus proteasome.

26S proteasome is composed of 20S proteasome and two units of 19S proteasome, the two units of 19S proteasome being attached to the 20S proteasome. 20S proteasome has a cylindrical structure in which an α-ring consisting of 7 subunits of α1 to α7 and a β-ring consisting of 7 subunits of β1 to β7 are stacked in order of αββα, and β1, β2, and β5 show catalytic activities of a caspase-like activity, a trypsin-like activity, and a chymotrypsin-like activity, respectively.

In the immunoproteasome, the catalytic subunits β1, β2, and β5 are replaced with β1i, β2i, and β5i, respectively (Science, 1994, 265, 1234-1237).

In the thymus proteasome, β5t which is expressed specifically in cortical thymic epithelial cells (cTEC) is incorporated along with β1i and β2i (Science, 2007, 316, 1349-1353).

Examples of a protease other than the proteasome include β-secretase, γ-secretase, aminopeptidase, angiotensin-converting enzyme, bromelain, calpine I, calpine II, carboxypeptidase A, carboxypeptidase B, carboxypeptidase P, carboxypeptidase Y, caspase 1, caspase 2, caspase 3, caspase 5, caspase 6, caspase 7, caspase 8, caspase 9, caspase 13, cathepsin B, cathepsin C, cathepsin D, cathepsin G, cathepsin L, chymotrypsin, clostripain, collagenase, complement C1r, complement C1s, complement factor B, complement factor D, dipeptidyl peptidase I, dipeptidyl peptidase II, dipeptidyl peptidase IV, dispase, elastase, endoproteinase Arg-C, endoproteinase Glu-C, endoproteinase Lys-C, ficin, granzyme B, kallikrein, leucine aminopeptidase, matrix metalloprotease, metalloprotease, papain, pepsin, plasmin, procaspase 3, pronase E, proteinase K, renin, thermolysin, thrombin, trypsin, cytosol alanyl aminopeptidase, enkephalinase, neprilysin, and the like.

As used herein, the phrase "having an affinity with a protease" means the capability of binding to a protease, for example, via a covalent bond, a hydrogen bond, a hydrophobic bond, Van der Waals force, and the like. When the thermal stability of a protease changes in the presence of a certain molecule, the molecule can be determined as having an affinity with that protease.

As used herein, the phrase "without inhibiting degradation of a protein by a protease" means that, for example, the protein-degradation inducing tag does not bind to the degradation active site of the protease via a covalent bonding. When a protein is degraded by a protease in the presence of a certain molecule, and the degradation of the protein is inhibited in the presence of a protease inhibitor, the molecule can be considered not to inhibit the degradation of the protein by the protease.

Examples of the protein-degradation inducing tag include low molecular weight compounds, natural products, peptides, antibodies, and the like. The protein-degradation inducing tag preferably has a molecular weight within the range of, for example, 50 to 200000. When the protein-degradation inducing tag is a low molecular weight compound, the molecular weight of the protein-degradation inducing tag is preferably within the range of, for example, 50 to 5000.

There is no particular limitation for the structure of the protein-degradation inducing tag as long as the protein-degradation inducing tag has an affinity with a protease without inhibiting degradation of a protein by the protease. The protein-degradation inducing tag can be obtained by, for example, screening from the candidate molecules. Furthermore, the protein-degradation inducing tag can be produced by inactivating the protease inhibitory activity (for example, proteasome inhibitoryactivity) of a protease inhibitor (for example, a proteasome inhibitor).

In a certain embodiment, for example, the protein-degradation inducing tag may have a structure represented by the following formula (I). It is demonstrated that the compound represented by the following formula (I) has an affinity with a protease, and does not inhibit the degradation of protein by the protease (see, for example, the below-mentioned Reference Examples 1 to 4).

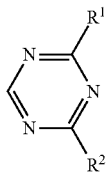

(I)

In the formula (I), $R^1$ and $R^2$ each independently represent a hydrocarbon group having 1 to 20 carbon atoms, an alkoxy group having 1 to 20 carbon atoms, an aryloxy group having 6 to 20 carbon atoms, a hydroxy group, a carboxy group, an amino group, or a halogeno group.

Examples of the hydrocarbon group include an alkyl group, an alkenyl group, an aryl group, combinations thereof, and the like. Specific examples include an alkyl group having 1 to 20 carbon atoms such as a methyl group and an ethyl group; an alkenyl group having 2 to 20 carbon atoms such as a vinyl group and an allyl group; an aryl group having 6 to 20 carbon atoms such as a phenyl group and a naphthyl group; an arylalkyl group having 7 to 20 carbon atoms such as a benzyl group and a phenethyl group; an alkylaryl group having 7 to 20 carbon atoms such as a tolyl group and a xylyl group; and the like. Examples of the halogeno group include a fluoro group, a chloro group, a bromo group, and the like.

In another embodiment, the protein-degradation inducing tag may have a structure in which the proteasome inhibitory activity of a proteasome inhibitor is inactivated. More specifically, at least one inhibitory activity selected from a caspase-like activity, a trypsin-like activity, and a chymotrypsin-like activity can be mentioned as the proteasome inhibitory activity.

The term "structure in which a proteasome inhibitory activity is inactivated" as used herein encompasses a structure in which a proteasome inhibitory activity is attenuated in addition to a structure in which a proteasome inhibitory activity is completely eliminated. In a certain embodiment, the protein-degradation inducing tag has a 50% inhibition concentration ($IC_{50}$) against at least one selected from a caspase-like activity, a trypsin-like activity, and a chymotrypsin-like activity which is 2 times or more of the 50% inhibition concentration ($IC_{50}$) of the original proteasome inhibitor.

As the proteasome inhibitor, any compound having a proteasome inhibitory activity can be used. A proteasome inhibitor is a compound which has an affinity with a proteasome (a protease complex), and inhibits degradation of a protein by a proteasome. Therefore, a protein-degradation inducing tag may be obtained by replacing the active site of a proteasome inhibitor with another structural moiety to inactivate the proteasome inhibitory activity. Proteasome inhibitors are being studied as anticancer agents, and there are many compounds that have been approved as pharmaceutical products, or are under clinical trials. Moreover, many of proteasome inhibitors have relatively small molecular weights and low hydrophobicity, and are less problematic in terms of cell membrane permeability, cytotoxicity, and the like. For these reasons, synthesizing a protein-degradation inducing tag based on a proteasome inhibitor is quite reasonable and efficient.

Examples of the proteasome inhibitor are shown in the following Tables 9 and 10. The proteasome inhibitors shown in Tables 9 and 10 are each a 20S proteasome inhibitor having an affinity with the active center part of 20S proteasome. Furthermore, the proteasome inhibitors shown in Tables 9 and 10 naturally have affinity with 26S proteasome. However, a proteasome inhibitor which can be used for producing a protein-degradation inducing tag shall not be limited to these examples.

TABLE 9

| No. | Generic name/ Product name | Structural formula (Circles indicate active sites) | Molecular weight |
|---|---|---|---|
| 1 | Bortezomib | 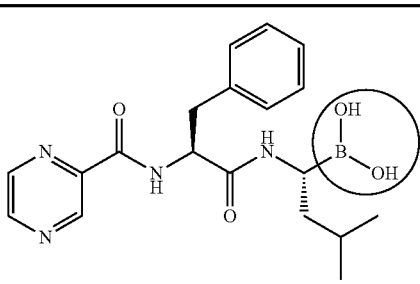 | 384.24 |
| 2 | ALLN (MG-101, Calpain inhibitor I) | 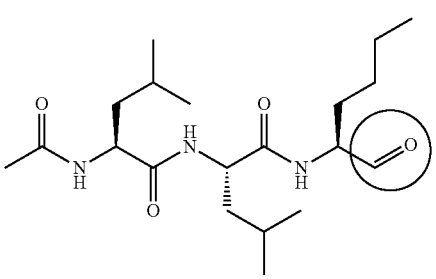 | 383.53 |

TABLE 9-continued
| No. | Generic name/ Product name | Structural formula (Circles indicate active sites) | Molecular weight |
|---|---|---|---|
| 3 | MLN9708 (Ixazomib) | 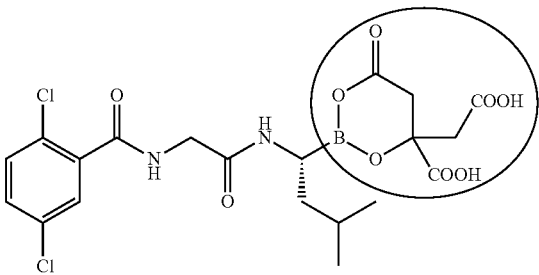 [SMILES: CC(C)C[C@H](NC(=O)CNC(=O)c1cc(Cl)ccc1Cl)B1OC(=O)CC(CC(=O)O)(C(=O)O)O1] | 517.12 |
| 4 | MLN2238 | 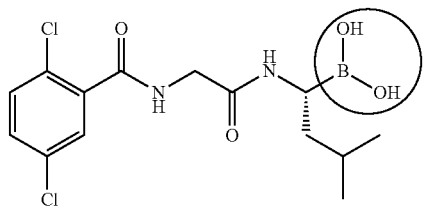 [SMILES: CC(C)C[C@H](NC(=O)CNC(=O)c1cc(Cl)ccc1Cl)B(O)O] | 361.03 |
| 5 | CEP-18770 | 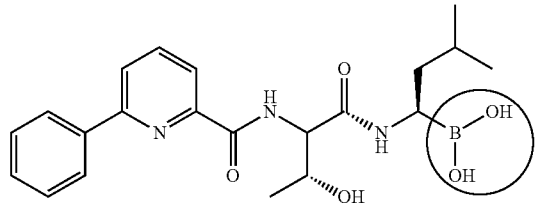 | 413.28 |
| 6 | ONO-7058 (Oprozomib) | 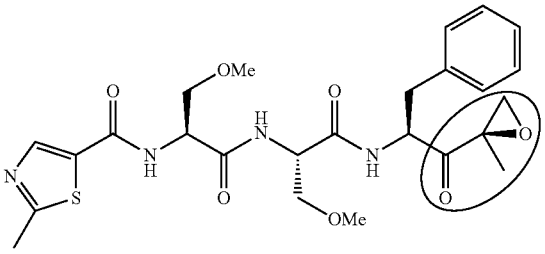 [SMILES: COC[C@H](NC(=O)c1cnc(C)s1)C(=O)N[C@@H](COC)C(=O)N[C@@H](Cc1ccccc1)C(=O)[C@@]1(C)CO1] | 532.61 |
| 7 | MG-132 | 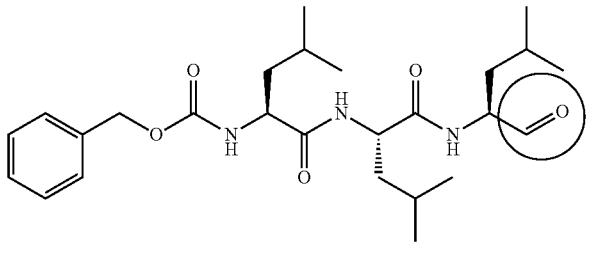 | 475.63 |

TABLE 10

| Generic name/ No. Product name | Structural formula (Circles indicate active sites) | Molecular weight |
|---|---|---|
| 8 Carfilzomib | | 719.92 |
| 9 BSc-2118 | | 533.66 |
| 10 PSI | | 604.75 |
| 11 Epoxomicin | | 554.73 |
| 12 ONX-0914 | | 580.68 |

TABLE 10-continued

| Generic name/ No. Product name | Structural formula (Circles indicate active sites) | Molecular weight |
| --- | --- | --- |
| 13 $^{125}$I-NIP-L$_3$VS | | 720.64 |
| 14 NPI-0052 (Marizomib) | | 313.78 |

For example, bortezomib as a boronic acid-based proteasome inhibitor is known to inhibit a proteasome activity when the boronyl group as an active site covalently binds to the degradation active site of 20S proteasome as shown in the following scheme (Kisselev, A. F. et al., Chemistry & Biology, 2012, 19, 99-115).

Further, MLN9708 and MLN2238, which are boronic acid-based proteasome inhibitors, are known to inhibit a proteasome activity when the boronic acid ester moiety or the boronyl group as an active site covalently binds to the degradation active site of 20S proteasome as shown in the following scheme (Kisselev, A. F. et al., Chemistry & Biology, 2012, 19, 99-115).

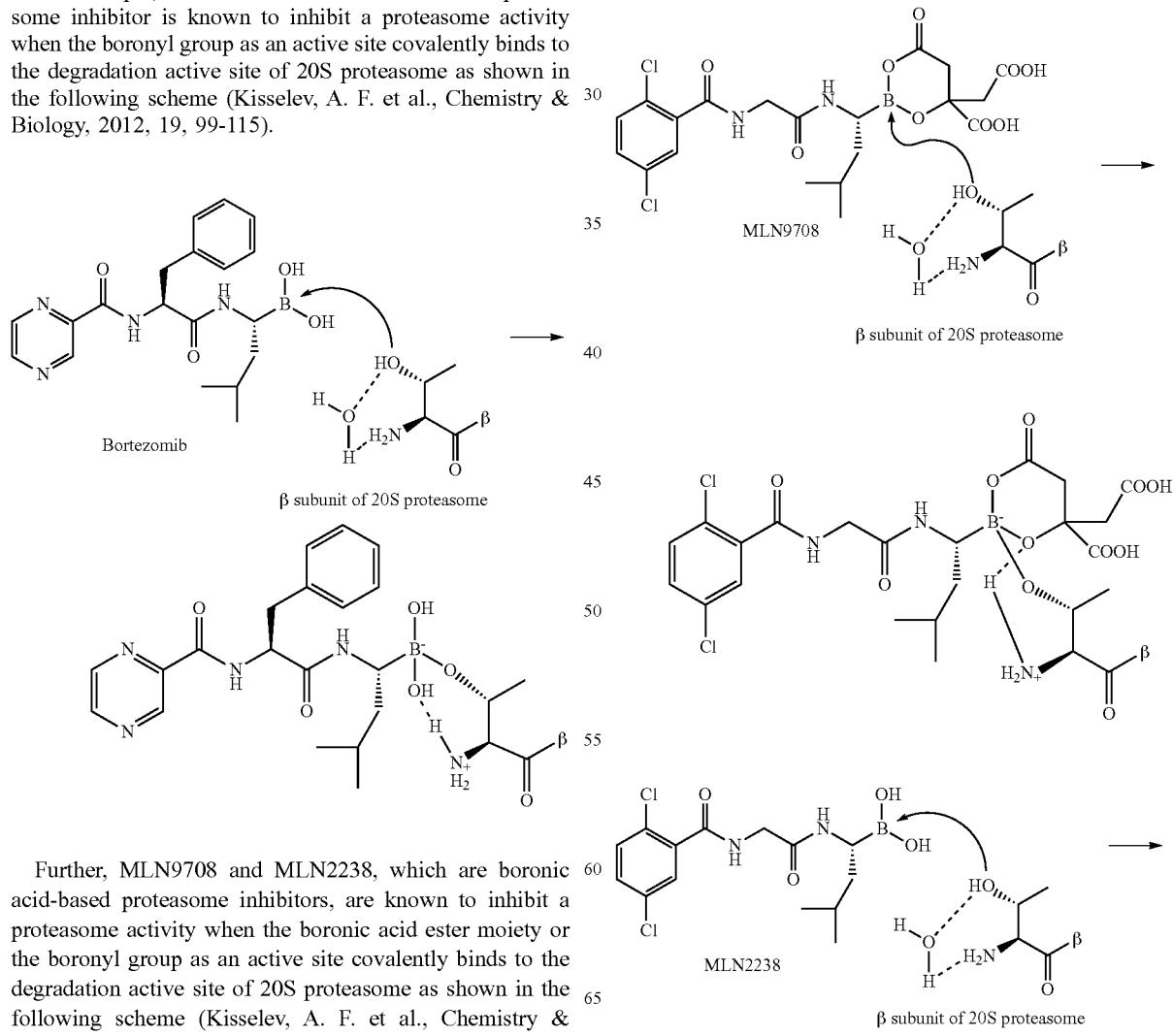

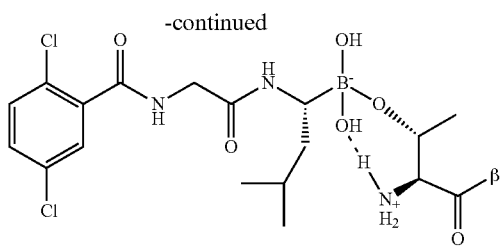

Therefore, a protein-degradation inducing tag may be obtained by replacing the boronyl group or the boronic acid ester moiety as the active sites of bortezomib, MLN9708, and MLN2238 with another structural moiety (a carboxy group, an alkyl group, an aryl group, an amino group, a hydroxy group, and the like) to inactivate the proteasome inhibitory activity.

It is noted that even for other boronic acid-based proteasome inhibitors such as CEP-18770, a protein-degradation inducing tag can be obtained by replacing the active site with another structural moiety (a carboxy group, an alkyl group, an aryl group, an amino group, a hydroxy group, and the like).

Further, ALLN, which is an aldehyde-based proteasome inhibitor, is known to inhibit a proteasome activity when the formyl group as an active site covalently binds to the degradation activity site of 20S proteasome as shown in the following scheme (Kisselev, A. F. et al., Chemistry & Biology, 2012, 19, 99-115).

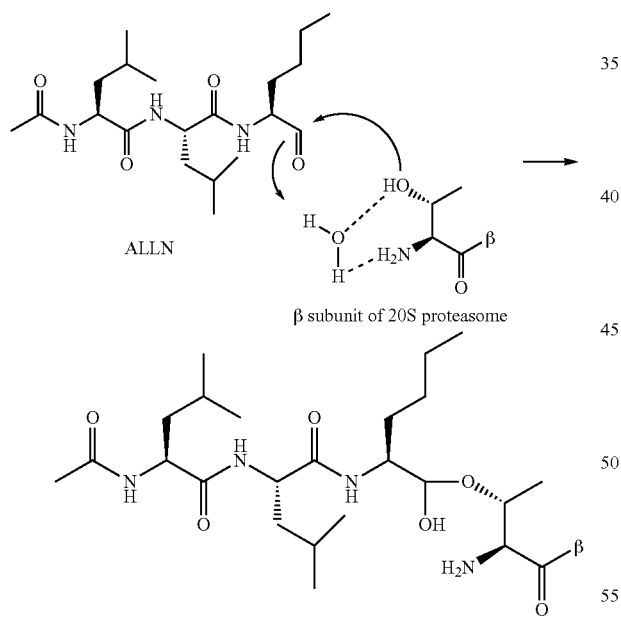

Therefore, a protein-degradation inducing tag can be obtained by replacing the formyl group as the active site of ALLN with another structural moiety (a carboxy group, an alkyl group, an aryl group, an amino group, a hydroxy group, and the like) to inactivate the proteasome inhibitory activity.

It is noted that even for other aldehyde-based proteasome inhibitors such as MG-132, BSc-2118, and PSI, a protein-degradation inducing tag can be obtained by replacing the formyl group as an active site with another structural moiety (a carboxy group, an alkyl group, an aryl group, an amino group, a hydroxy group, and the like).

Examples of the protein-degradation inducing tag having a structure in which the proteasome inhibitory activity of a proteasome inhibitor is inactivated are shown in the following Tables 11 and 12. Examples of the monovalent group represented by R in the tables include a carboxy group, an alkyl group having 1 to 20 carbon atoms, an aryl group having 6 to 20 atoms, an amino group, a hydroxy group, and the like.

TABLE 11

| No. | Structural formula |
|---|---|
| 1 | (In the formula, R represents a monovalent group except for —B(OH)₂.) |
| 2 | (In the formula, R represents a monovalent group except for —CHO.) |
| 3 | (In the formula, R represents a monovalent group except for 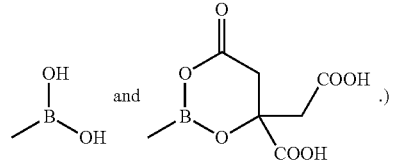 ) |

TABLE 11-continued

| No. | Structural formula |
|---|---|
| 4 | 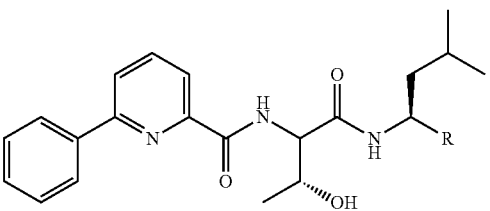 (In the formula, R represents a monovalent group except for boronic acid.) |
| 5 | 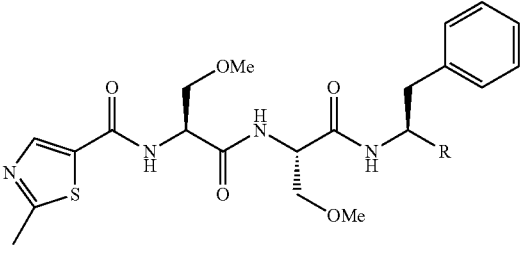 (In the formula, R represents a monovalent group except for epoxyketone.) |
| 6 | 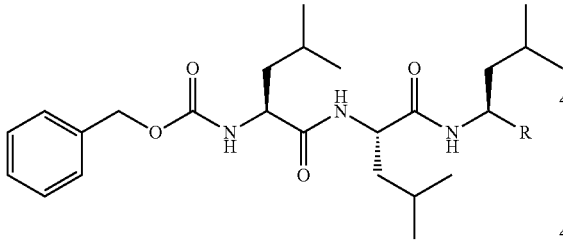 (In the formula, R represents a monovalent group except for —CHO.) |
| 7 | 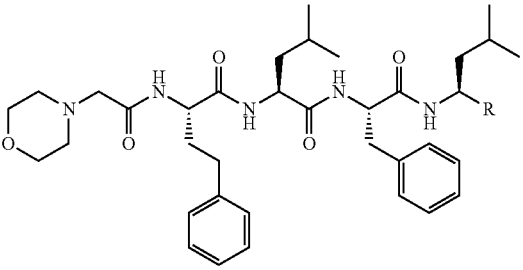 (In the formula, R represents a monovalent group except for epoxyketone.) |

TABLE 12

| No. | Structural formula |
|---|---|
| 8 | 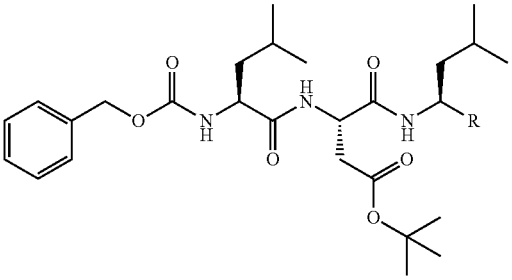 (In the formula, R represents a monovalent group except for —CHO.) |
| 9 | 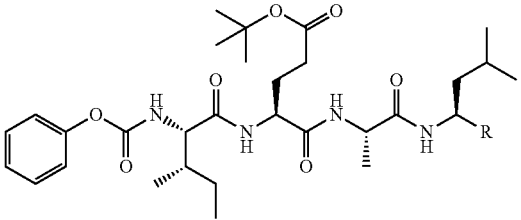 (In the formula, R represents a monovalent group except for —CHO.) |
| 10 | 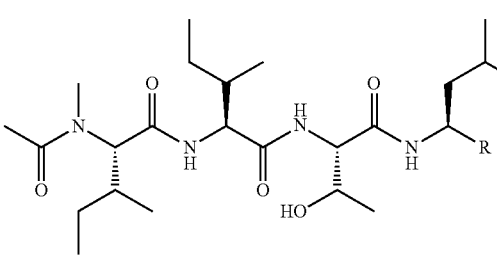 (In the formula, R represents a monovalent group except for epoxyketone.) |

TABLE 12-continued

| No. | Structural formula |
|---|---|
| 11 | 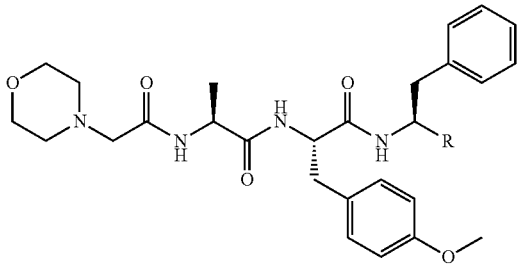<br>(In the formula, R represents a monovalent group except for 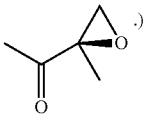.) |
| 12 | 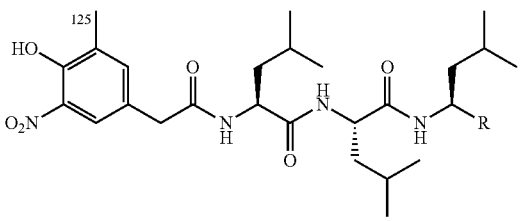<br>(In the formula, R represents a monovalent group except for 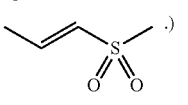.) |
| 13 | 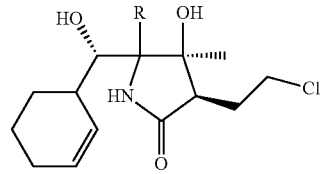<br>(In the formula, R represents a monovalent group.) |
| 14 | 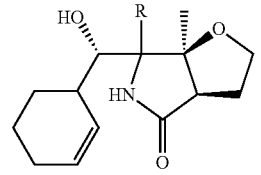<br>(In the formula, R represents a monovalent group.) |

Other examples of the proteasome inhibitor are shown in the following Tables 13 to 18. Even for these proteasome inhibitors, a protein-degradation inducing tag can be obtained by inactivating the proteasome inhibitory activity in a similar way as described above.

TABLE 13

| | 20S proteasome inhibitor | | |
|---|---|---|---|
| No. | Generic name/ Product name | Structural formula | Molecular weight |
| 15 | Aspirin | 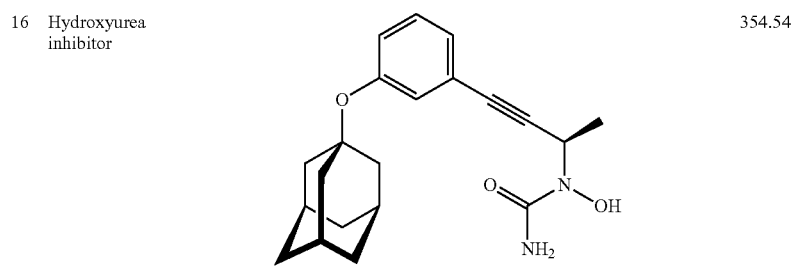 | 180.15 |
| 16 | Hydroxyurea inhibitor | | 354.54 |

TABLE 13-continued 20S proteasome inhibitor

| No. | Generic name/ Product name | Structural formula | Molecular weight |
|---|---|---|---|
| 17 | PI-1840 | | 394.47 |
| 18 | PI-083 | | 439.87 |
| 19 | Cerastol | | 450.61 |

TABLE 14

20S proteasome inhibitor (Continued)

| No. | Generic name/ Product name | Structural formula | Molecular weight |
|---|---|---|---|
| 20 | CVT-659 | | 571.66 |

TABLE 14-continued
| | | 20S proteasome inhibitor (Continued) | |
|---|---|---|---|
| No. | Generic name/ Product name | Structural formula | Molecular weight |
| 21 | Capped dipeptide 2 | 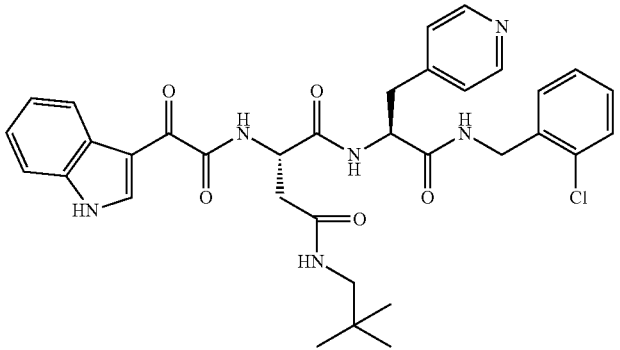 [SMILES: CC(C)(C)CNC(=O)C[C@H](NC(=O)C(=O)c1c[nH]c2ccccc12)C(=O)N[C@@H](Cc1ccncc1)C(=O)NCc1ccccc1Cl] | 645.15 |
| 22 | TMC95A | 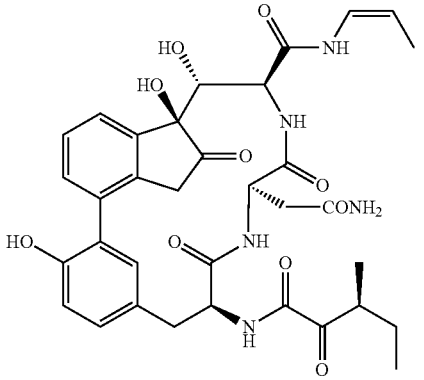 [SMILES: C/C=C\NC(=O)[C@H]1NC(=O)[C@@H](CC(N)=O)NC(=O)[C@@H](NC(=O)C(=O)[C@@H](C)CC)Cc2ccc(O)c(c2)-c2cccc3c2CC(=O)[C@@]3(O)[C@@H]1O] | 677.71 |
| 23 | Capped dipeptide 1 | 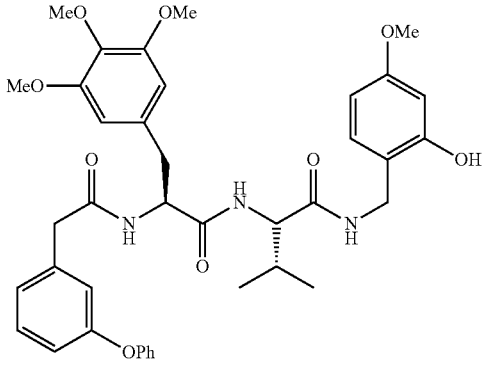 | 699.80 |

TABLE 15

| | | 20S proteasome inhibitor (Continued) | |
|---|---|---|---|
| No. | Generic name/ Product name | Structural formula | Molecular weight |
| 24 | Ritonavir | | 720.94 |
| 25 | Scytonemide A | | 744.89 |
| 26 | Argyrin A | | 824.91 |

TABLE 15-continued 20S proteasome inhibitor (Continued)

| No. | Generic name/Product name | Structural formula | Molecular weight |
|---|---|---|---|
| 27 | Benzylstatine peptide 1 | 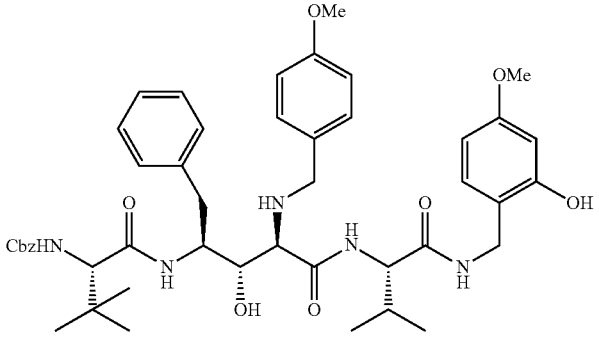 [SMILES: COc1ccc(CN[C@@H](C(=O)N[C@H](C(=O)NCc2ccc(OC)cc2O)C(C)C)[C@H](O)[C@H](Cc2ccccc2)NC(=O)[C@@H](NC(=O)OCc2ccccc2)C(C)(C)C)cc1] | 826.00 |

TABLE 16

19S proteasome inhibitor

| No. | Generic name/Product name | Structural formula | Molecular weight |
|---|---|---|---|
| 1 | RIP-4 (Rpt4) inhibitor) | 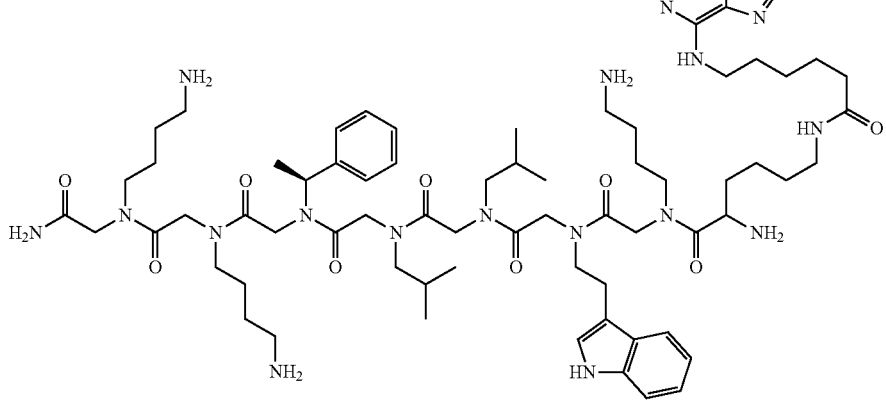 | 1348.76 |

TABLE 17

Inhibitor for a constituent factor other than 20S/19S

| No. | Generic name/Product name | Structural formula | Molecular weight | Others |
|---|---|---|---|---|
| 1 | JBIR-22 | 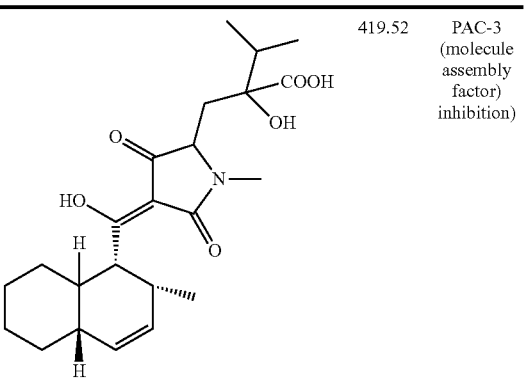 | 419.52 | PAC-3 (molecule assembly factor) inhibition) |

TABLE 18

20S immunoproteasome inhibitor

| No. | Generic name/ Product name | Structural formula | Molecular weight | Others |
|---|---|---|---|---|
| 1 | PR-957 | | 580.68 | β5i is inhibited |
| 2 | IPSI-001 | | 362.47 | β2i is inhibited |
| 3 | LMP2-sp-ek | | 484.75 | β2i is inhibited |

In another embodiment, the protein-degradation inducing tag may have a structure in which the protease inhibitory activity of a protease inhibitor (except for the proteasome inhibitors described above) is inactivated.

The term "structure in which a protease inhibitory activity is inactivated" as used herein encompasses a structure in which the protease inhibitory activity is attenuated in addition to a structure in which the protease inhibitory activity is completely eliminated. In a certain embodiment, the protein-degradation inducing tag has a 50% inhibition concentration ($IC_{50}$) against a protease as an inhibition target of a protease inhibitor which is 2 times or more of the 50% inhibition concentration ($IC_{50}$) of the original protease inhibitor.

As a protease inhibitor, any compound having a protease inhibitory activity can be used. The protease inhibitor is a compound having an affinity with a protease and inhibiting degradation of a protein by the protease. Therefore, a protein-degradation inducing tag can be obtained by replacing the active site of a protease inhibitor with another structural moiety to inactivate the protease inhibitory activity.

Examples of the protease inhibitor are shown in the following Tables 19 to 86. Protein degradation inducing tags can be obtained by replacing the active sites of these protease inhibitors with other structural moieties to inactivate the protease inhibitory activities. However, a protease inhibitor which can be used for producing protein-degradation inducing tags shall not be limited to these examples. Existing data bases ("MEROPS-the peptidase database" (merops.sangerac.uk/index.shtml) and the like) can be consulted for information about proteases and protease inhibitors if needed.

TABLE 19

β-secretase inhibitor

| No. | Name | Structural formula | Molecular weight | Protease to be inhibited |
|---|---|---|---|---|
| 1 | OM99-2 | | 892.99 | |

TABLE 20

γ-secretase inhibitor

| No. | Name | Structural formula | Molecular weight | Protease to be inhibited |
|---|---|---|---|---|
| 1 | γ-Secretase inhibitor | | 705.83 | |
| 2 | L-685,458 | | 672.85 | |

TABLE 21

Aminopeptidase inhibitor

| No. | Name | Structural formula | Molecular weight | Protease to be inhibited |
|---|---|---|---|---|
| 1 | Cysteamine | | 113.61 | |
| 2 | Bestatin | | 344.83 | Aminopeptidase B Leucine aminopeptidase |

TABLE 22

Angiotensin converting enzyme inhibitor

| No. | Name | Structural formula | Molecular weight | Protease to be inhibited |
|---|---|---|---|---|
| 1 | Captopril | 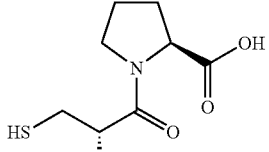 | 217.29 | Formation of angiotensin II is inhibited |
| 2 | Fenoldopam monohydrobromide | 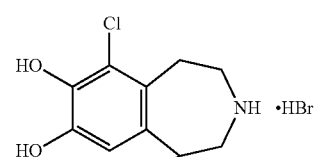 | 386.67 | |
| 3 | Angiotensin Converting Enzyme Inhibitor | 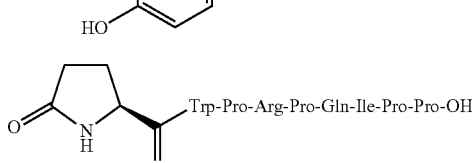 Trp-Pro-Arg-Pro-Gln-Ile-Pro-Pro-OH | 1101.26 | |

TABLE 23

Bromelain inhibitor

| No. | Name | Structural formula | Molecular weight | Protease to be inhibited |
|---|---|---|---|---|
| 1 | E-64 | 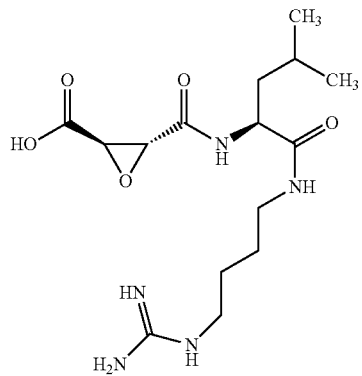 [SMILES: CC(C)C[C@H](NC(=O)[C@@H]1O[C@H]1C(=O)O)C(=O)NCCCCNC(=N)N] | 357.41 | Cathepsin B<br>Ficin<br>Papain<br>Bromelain |
| 2 | N-Ethylmaleimide | 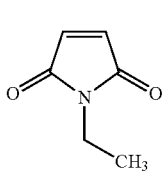 | 125.13 | Calpine<br>Ficin |

TABLE 23-continued

Bromelain inhibitor

| No. | Name | Structural formula | Molecular weight | Protease to be inhibited |
|---|---|---|---|---|
| 3 | N-p-Tosyl-L-phenilalanine chloromethyl ketone | | 351.85 | Papain Chymotrypsin Ficin Bromelain |
| 4 | Sodium iodoacetate | | 207.93 | Carboxypeptidase P Bromelain Ficin Cathepsin |

TABLE 24

Calpain inhibitor

| No. | Name | Structural formula | Molecular weight | Protease to be inhibited |
|---|---|---|---|---|
| 1 | E-64c | | 314.38 | |
| 2 | E-64d | | 342.43 | |
| 3 | Z-Leu-Leu-Leu-fluoromethyl ketone | | 507.64 | |
| 4 | N-Ethylmaleimide | | 125.13 | Ficin Calpine |

TABLE 24-continued

Calpain inhibitor

| No. | Name | Structural formula | Molecular weight | Protease to be inhibited |
|---|---|---|---|---|
| 5 | Antipain dihydrochloride from microbial source | 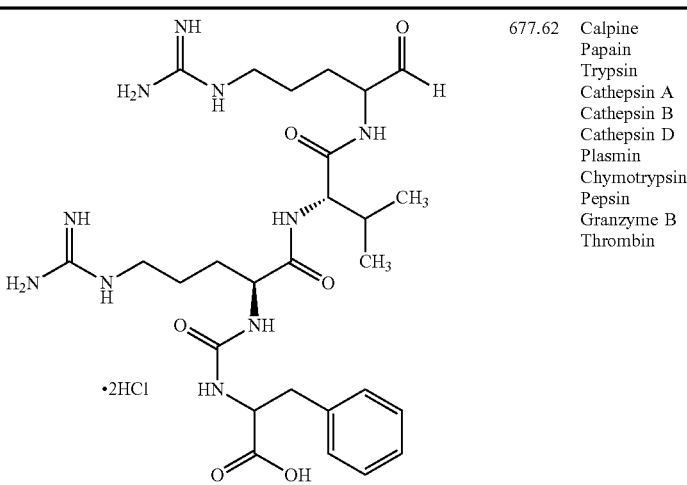 | 677.62 | Calpine<br>Papain<br>Trypsin<br>Cathepsin A<br>Cathepsin B<br>Cathepsin D<br>Plasmin<br>Chymotrypsin<br>Pepsin<br>Granzyme B<br>Thrombin |
| 6 | 4-Chloromercuri-benzoic acid | 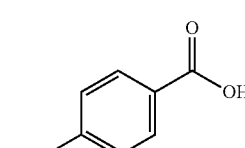 | 357.16 | Calpine<br>Carboxypeptidase<br>Clostripain |
| 7 | Leupeptin | 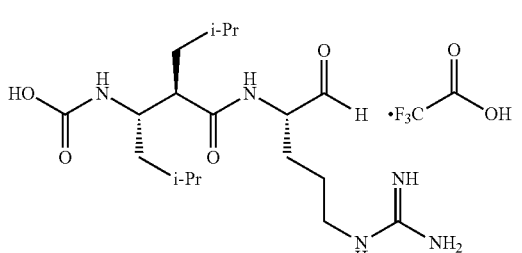 | 426.55 | Plasmin<br>Trypsin<br>Papain<br>Calpine<br>Cathepsin B<br>Thrombin<br>Kallikrein<br>Endoproteinase<br>Chymotrypsin<br>Proteasome (β2) |

TABLE 25

Calpain I inhibitor

| No. | Name | Structural formula | Molecular weight | Protease to be inhibited |
|---|---|---|---|---|
| 1 | Calpain Inhibitor I (ALLN, Ac-LLnL-CHO, MG-101) | 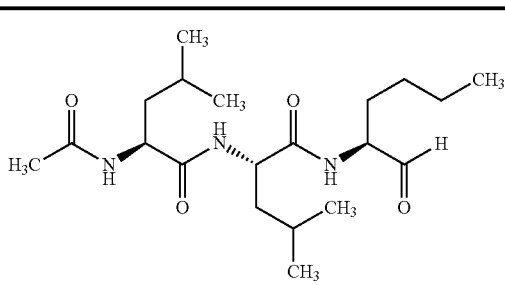 | 383.53 | Cathepsin B<br>Cathepsin L<br>Calpine<br>Proteasome |

TABLE 25-continued

Calpain I inhibitor

| No. | Name | Structural formula | Molecular weight | Protease to be inhibited |
|---|---|---|---|---|
| 2 | Calpain Inhibitor II | 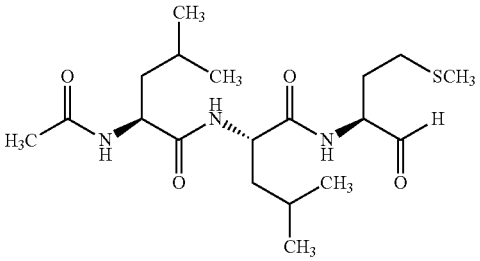 [SMILES: CSCC[C@@H](C=O)NC(=O)[C@H](CC(C)C)NC(=O)[C@H](CC(C)C)NC(C)=O] | 401.56 | Cathepsin B Calpine Proteasome |

TABLE 26

Calpain II inhibitor

| No. | Name | Structural formula | Molecular weight | Protease to be inhibited |
|---|---|---|---|---|
| 1 | E-64c | 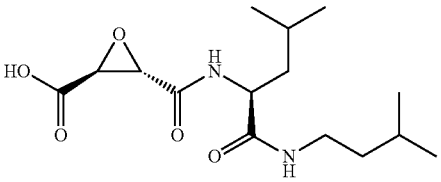 [SMILES: CC(C)CCNC(=O)[C@H](CC(C)C)NC(=O)[C@H]1O[C@@H]1C(=O)O] | 314.38 | |
| 2 | Calpain Inhibitor I (ALLN, Ac-LLnL-CHO, MG-101) | 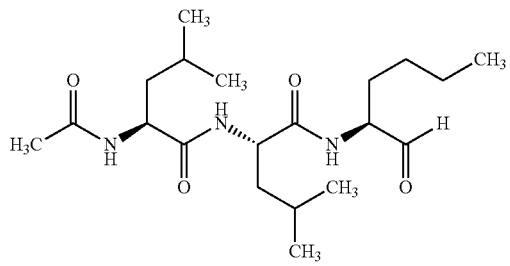 [SMILES: CCCC[C@@H](C=O)NC(=O)[C@H](CC(C)C)NC(=O)[C@H](CC(C)C)NC(C)=O] | 383.53 | Cathepsin B Cathepsin L Calpine Proteasome |
| 3 | Calpain Inhibitor II | 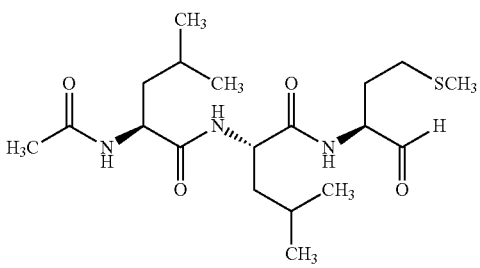 [SMILES: CSCC[C@@H](C=O)NC(=O)[C@H](CC(C)C)NC(=O)[C@H](CC(C)C)NC(C)=O] | 401.56 | Cathepsin B Calpine Proteasome |
| 4 | N-Ethylmaleimide | 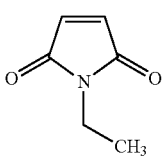 | 125.13 | Ficin Calpine |

TABLE 26-continued

| | | Calpain II inhibitor | | |
|---|---|---|---|---|
| No. | Name | Structural formula | Molecular weight | Protease to be inhibited |
| 5 | Antipain dihydrochloride from microbial source | 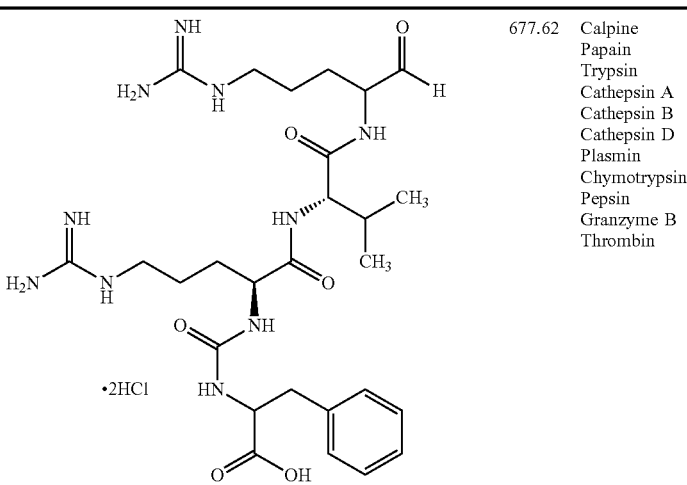 | 677.62 | Calpine<br>Papain<br>Trypsin<br>Cathepsin A<br>Cathepsin B<br>Cathepsin D<br>Plasmin<br>Chymotrypsin<br>Pepsin<br>Granzyme B<br>Thrombin |
| 6 | 4-Chloromercuri-benzoic acid | 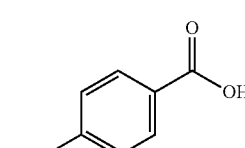 | 357.16 | Calpine<br>Carboxypeptidase<br>Clostripain |
| 7 | Leupeptin | 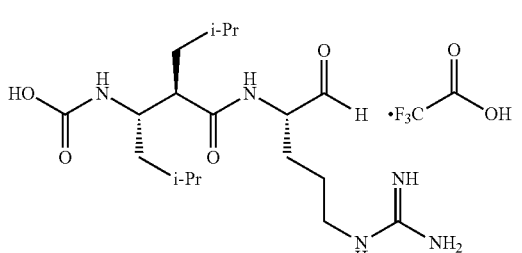 | 426.55 | Plasmin<br>Trypsin<br>Papain<br>Calpine<br>Cathepsin B<br>Thrombin<br>Kallikrein<br>Endoproteinase<br>Chymotrypsin<br>Proteasome (β2) |

TABLE 27

| | | Carboxypeptidase A/B inhibitor | | |
|---|---|---|---|---|
| No. | Name | Structural formula | Molecular weight | Protease to be inhibited |
| 1 | Ethylene glycol-bis(2-aminoethyl ether)-N,N,N',N'-tetraacetic acid | 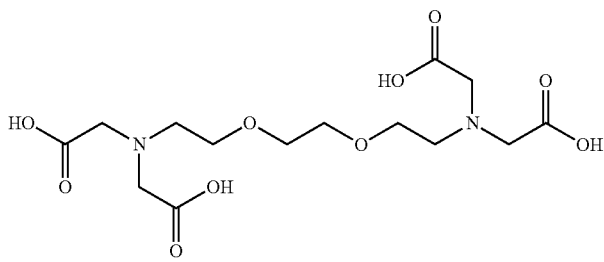 [SMILES: O=C(O)CN(CCOCCOCCN(CC(=O)O)CC(=O)O)CC(=O)O] | 380.35 | Carboxypeptidase A<br>Carboxypeptidase B |

TABLE 27-continued

Carboxypeptidase A/B inhibitor

| No. | Name | Structural formula | Molecular weight | Protease to be inhibited |
|---|---|---|---|---|
| 2 | EDTA disodium salt | (structure shown) ·2H$_2$O; R = H or Na (2:2) | 372.24 | Carboxypeptidase A<br>Carboxypeptidase B<br>Dispase<br>Collagenase |
| 3 | Pentetic acid (DETAPAC, DTPA) | (structure shown) | 393.35 | Carboxypeptidase A<br>Carboxypeptidase B |
| 4 | 1,10-Phenanthroline monohydrate | (structure shown) ·H$_2$O | 198.22 | Carboxypeptidase A<br>Carboxypeptidase B<br>Dispase<br>Leucine aminopeptidase<br>Thermolysin |

TABLE 28

Carboxypeptidase P inhibitor

| No. | Name | Structural formula | Molecular weight | Protease to be inhibited |
|---|---|---|---|---|
| 1 | Diisopropyl-fluorophosphate | (structure shown) | 184.15 | Carboxypeptidase<br>Chymotrypsin<br>Complement<br>Elastase<br>Endoproteinase<br>Kallikrein<br>Plasmin<br>Thrombin<br>Pronase<br>Proteinase |
| 2 | 4-Chloromercuribenzoic acid | (structure shown) | 357.16 | Calpine<br>Carboxypeptidase<br>Clostripain |
| 3 | Diethyl pyrocarbonate (DEP) | (structure shown) | 162.14 | |

TABLE 28-continued

| | | Carboxypeptidase P inhibitor | | |
|---|---|---|---|---|
| No. | Name | Structural formula | Molecular weight | Protease to be inhibited |
| 4 | Sodium iodoacetate | 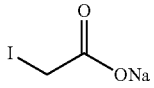 | 207.93 | Carboxypeptidase P<br>Bromelain<br>Ficin<br>Cathepsin |

TABLE 29

| | | Carboxypeptidase Y inhibitor | | |
|---|---|---|---|---|
| No. | Name | Structural formula | Molecular weight | Protease to be inhibited |
| 1 | Diisopropyl-fluorophos-phate | 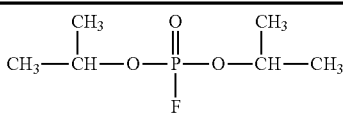 | 184.15 | Carboxypeptidase<br>Chymotrypsin<br>Complement<br>Elastase<br>Endoproteinase<br>Kallikrein<br>Plasmin<br>Thrombin<br>Pronase<br>Proteinase |
| 2 | Phenylmethane-sulfonyl fluoride | 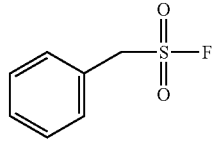 [SMILES: O=S(=O)(F)Cc1ccccc1] | 174.19 | Thrombin<br>Elastase<br>Plasmin<br>Proteinase |

TABLE 30

| | | Cathepsin B inhibitor | | |
|---|---|---|---|---|
| No. | Name | Structural formula | Molecular weight | Protease to be inhibited |
| 1 | CA-074 | 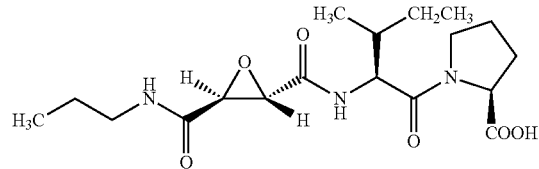 [SMILES: CCCNC(=O)[C@H]1O[C@@H]1C(=O)N[C@H](C(=O)N1CCC[C@H]1C(=O)O)C(C)CC] | 383.44 | |
| 2 | CA-074 methyl ester | 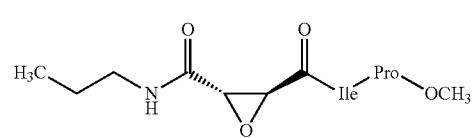 | 397.47 | |

TABLE 30-continued

Cathepsin B inhibitor

| No. | Name | Structural formula | Molecular weight | Protease to be inhibited |
|---|---|---|---|---|
| 3 | E-64 | | 357.41 | Cathepsin B<br>Ficin<br>Papain<br>Bromelain |
| 4 | Z-Phe-Phe-fluoromethyl ketone (Z-FF-FMK) | | 462.51 | |
| 5 | Antipain dihydrochloride from microbial source | | 677.62 | Calpine<br>Papain<br>Trypsin<br>Cathepsin A<br>Cathepsin B<br>Cathepsin D<br>Plasmin<br>Chymotrypsin<br>Pepsin |

TABLE 31

Cathepsin B inhibitor (Continued)

| No. | Name | Structural formula | Molecular weight | Protease to be inhibited |
|---|---|---|---|---|
| 6 | Calpain Inhibitor I (ALLN, Ac-LLnL-CHO, MG-101) | | 383.53 | Cathepsin B<br>Cathepsin L<br>Calpine<br>Proteasome |

TABLE 31-continued

Cathepsin B inhibitor (Continued)

| No. | Name | Structural formula | Molecular weight | Protease to be inhibited |
|---|---|---|---|---|
| 7 | Calpain Inhiitor II | 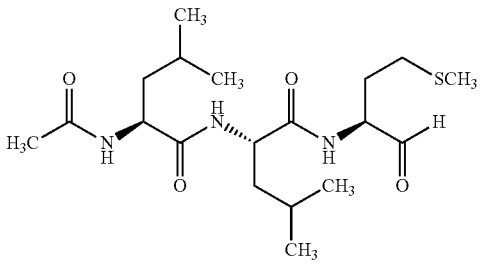 [SMILES: CSCC[C@@H](C=O)NC(=O)[C@H](CC(C)C)NC(=O)[C@H](CC(C)C)NC(C)=O] | 401.56 | Cathepsin B Calpine Proteasome |
| 8 | Chymostatin | 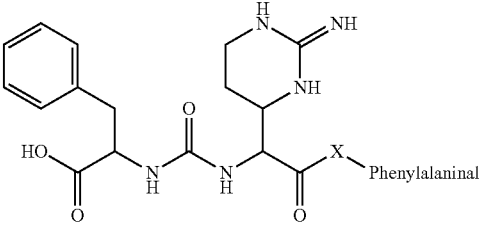<br>Chymostatin A  X = Leu<br>Chymostatin B  X = Val<br>Chymostatin C  X = Ile | A: MW = 607.7<br>B: MW = 593.7<br>C: MW = 607.7 | A: Chymotrypsin Papain<br>B: Chymotrypsin-like serine proteinase<br>C: Cathepsin A, B, C, B, H, L |
| 9 | Leupeptin | 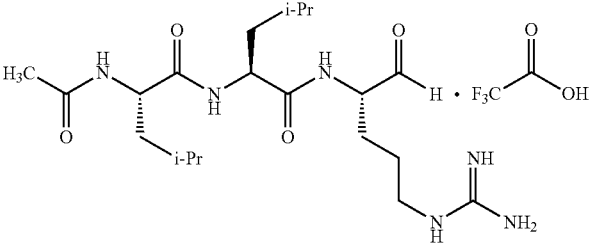 | 426.55 | Plasmin Trypsin Papain Calpine Cathepsin B Thrombin Kallikrein Endoproteinase Chymotrypsin Proteasome (β2) |

TABLE 32

Cathepsin C inhibitor

| No. | Name | Structural formula | Molecular weight | Protease to be inhibited |
|---|---|---|---|---|
| 1 | Sodium iodoacetate | 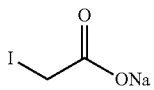 | 207.93 | Carboxypeptidase P Bromelain Ficin Cathepsin |

TABLE 33

Cathepsin D inhibitor

| No. | Name | Structural formula | Molecular weight | Protease to be inhibited |
|---|---|---|---|---|
| 1 | Antipain dihydrochoride from microbial source | 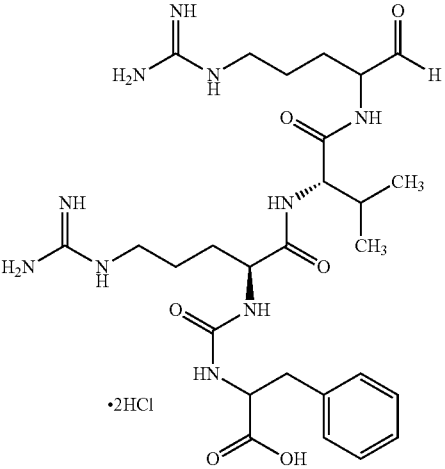 [SMILES: CC(C)[C@H](NC(=O)[C@H](CCCNC(=N)N)NC(=O)NC(Cc1ccccc1)C(=O)O)C(=O)NC(C=O)CCCNC(=N)N] | 677.62 | Calpine Papain Trypsin Cathepsin A Cathepsin B Cathepsin D Plasmin Chymotrypsin Pepsin Granzyme B Thrombin |
| 2 | Chymostatin | 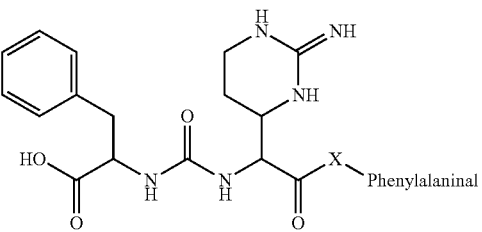  Chymostatin A  X = Leu  Chymostatin B  X = Val  Chymostatin C  X = Ile | A: MW = 607.7  B: MW = 593.7  C: MW = 607.7 | Chymotrypsin Papain Chymotrypsin-like serine proteinase Cathepsin A, B, C, B, H, L Proteasome ($\beta$5) |
| 3 | Pepstatin A | 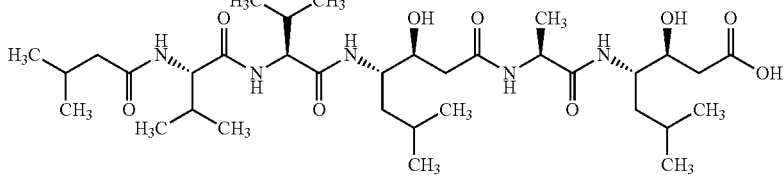 | 685.89 | Pepsin Cathepsin |

TABLE 34

Cathepsin L inhibitor

| No. | Name | Structural formula | Molecular weight | Protease to be inhibited |
|---|---|---|---|---|
| 1 | Z-Phe-Phe-fluoromethyl ketone (Z-FF-FMK) | 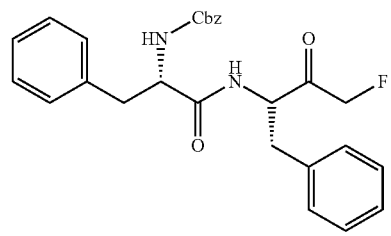 | 462.51 | |

TABLE 34-continued

Cathepsin L inhibitor

| No. | Name | Structural formula | Molecular weight | Protease to be inhibited |
|---|---|---|---|---|
| 2 | Calpain Inhibitor I (ALLN, Ac-LLnL-CHO, MG-101) | [structure] | 383.53 | Cathepsin B Cathepsin L Calpine Proteasome |

TABLE 35

Chymotrypsin inhibitor

| No. | Name | Structural formula | Molecular weight | Protease to be inhibited |
|---|---|---|---|---|
| 1 | Diisopropyl-fluorophos-phate | [structure] | 184.15 | Carboxypeptidase Chymotrypsin Complement Elastase Endoproteinase Kallikrein Plasmin Thrombin Pronase Proteinase |
| 2 | 4-(2-Aminoethyl)benzene-sulfonyl fluoride hydrochloride (AEBSF) | [structure] | 239.69 | Plasmin Trypsin Chymotrypsin |
| 3 | 6-Aminocapro-ic acid | [structure] | 131.17 | |
| 4 | Chymostatin | [structure] Chymostatin A X = Leu Chymostatin B X = Val Chymostatin C X = Ile | A: MW = 607.7 B: MW = 593.7 C: MW = 607.7 | Chymotrypsin Papain Chymotrypsin-like serine proteinase Cathepsin A, B, C, B, H, L Proteasome (β5) |

TABLE 36

Chymotrypsin inhibitor (Continued)

| No. | Name | Structural formula | Molecular weight | Protease to be inhibited |
|---|---|---|---|---|
| 1 | N-p-Tosyl-L-phenylalanine chloromethyl ketone | | 351.85 | Papain<br>Chymotrypsin<br>Ficin<br>Bromelain |
| 2 | Bromoenol lactone | | 317.18 | |
| 3 | Gabexate mesylate | | 417.48 | |
| 4 | Leupeptin | | 426.55 | Plasmin<br>Trypsin<br>Papain<br>Calpine<br>Cathepsin B<br>Thrombin<br>Kallikrein<br>Endoproteinase<br>Chymotrypsin<br>Proteasome (β2) |

TABLE 37

Clostripain inhibitor

| No. | Name | Structural formula | Molecular weight | Protease to be inhibited |
|---|---|---|---|---|
| 1 | 4-Chloromercuribenzoic acid | | 357.16 | Calpine<br>Carboxypeptidase<br>Clostripain |

TABLE 37-continued

Clostripain inhibitor

| No. | Name | Structural formula | Molecular weight | Protease to be inhibited |
|---|---|---|---|---|
| 2 | Nα-Tosyl-L-lysine chloromethyl ketone hydrochloride | | 369.31 | |

TABLE 38

Collagenase inhibitor

| No. | Name | Structural formula | Molecular weight | Protease to be inhibited |
|---|---|---|---|---|
| 1 | EDTA disodium salt | R = H or Na (2:2), ·2H$_2$O | 372.24 | Carboxypeptidase A<br>Carboxypeptidase B<br>Dispase<br>Collagenase |
| 2 | Dichloromethylene diphosphonic acid disodium salt (DMDP) | | 288.86 | |

TABLE 39

Complement C1r/C1s inhibitor

| No. | Name | Structural formula | Molecular weight | Protease to be inhibited |
|---|---|---|---|---|
| 1 | Diisopropyl-fluoro-phosphate | | 184.15 | Carboxypeptidase<br>Chymotrypsin<br>Complement<br>Elastase<br>Endoproteinase<br>Kallikrein<br>Plasmin<br>Thrombin<br>Pronase<br>Proteinase |

TABLE 40

Complement factor D/B inhibitor

| No. | Name | Structural formula | Molecular weight | Protease to be inhibited |
|---|---|---|---|---|
| 1 | Diisopropyl-fluoro-phosphate | 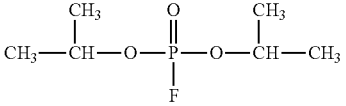 | 184.15 | Carboxypeptidase Chymotrypsin Complement Elastase Endoproteinase Kallikrein Plasmin Thrombin Pronase Proteinase |

TABLE 41

Dipeptidyl peptidase II inhibitor

| No. | Name | Structural formula | Molecular weight | Protease to be inhibited |
|---|---|---|---|---|
| 1 | Puromycin | 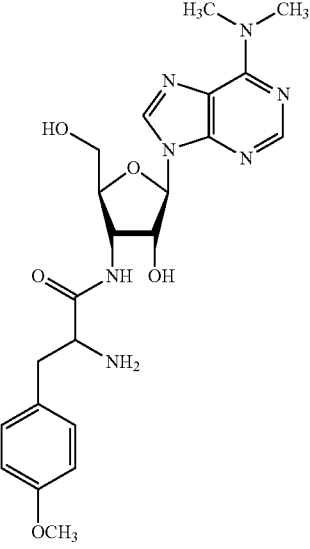 | 471.51 | Dipeptidyl peptidase II Cytosol alanyl aminopeptidase |

TABLE 42

Dipeptidyl peptidase III inhibitor

| No. | Name | Structural formula | Molecular weight | Protease to be inhibited |
|---|---|---|---|---|
| 1 | Opiorphin | 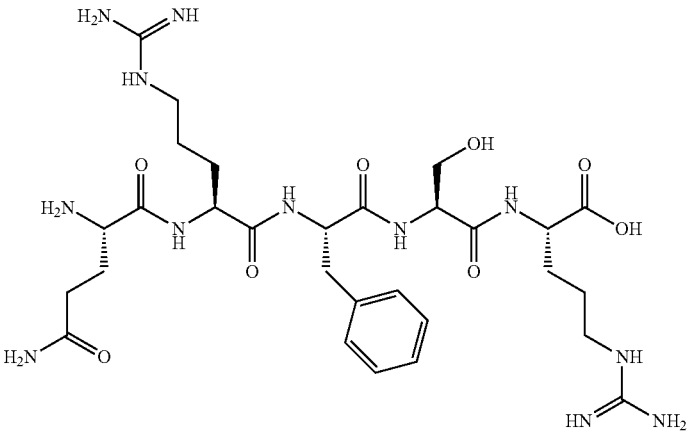 | 692.77 | Enkephalinase Neprilysin Dipeptidyl peptidase III Cytosol alanyl aminopeptidase |

TABLE 43

Dipeptidyl peptidase IV inhibitor

| No. | Name | Structural formula | Molecular weight | Protease to be inhibited |
|---|---|---|---|---|
| 1 | Ile-Pro-Ile | $CH_3CH_2CH(CH_3)-CH(NH_2)-C(=O)-N\text{(pyrrolidine)}-C(=O)-NH-CH(CH_3)-CH(CH_2CH_3)-C(=O)-OH$ | 341.45 | Dipeptidyl peptidase IV |

TABLE 44

Dispase inhibitor

| No. | Name | Structural formula | Molecular weight | Protease to be inhibited |
|---|---|---|---|---|
| 1 | EDTA disodium salt | (EDTA structure) •2H$_2$O, R = H or Na (2:2) | 372.24 | Carboxypeptidase A<br>Carboxypeptidase B<br>Dispase<br>Collagenase |
| 2 | 1,10-Phenanthroline monohydrate | (1,10-phenanthroline) •H$_2$O | 198.22 | Carboxypeptidase A<br>Carboxypeptidase B<br>Dispase<br>Leucin aminopeptidase<br>Thermolysin |

TABLE 45

Elastase (granulocyte) inhibitor

| No. | Name | Structural formula | Molecular weight | Protease to be inhibited |
|---|---|---|---|---|
| 1 | N-(Methoxy-succinyl)-Ala-Ala-Pro-Val-chloromethyl ketone | H$_3$CO-C(=O)-CH$_2$CH$_2$-C(=O)-Ala-Ala-Pro-Val-CH$_2$Cl | 502.99 | |

TABLE 46

Elastase (leukocyte) inhibitor

| No. | Name | Structural formula | Molecular weight | Protease to be inhibited |
|---|---|---|---|---|
| 1 | Diisopropyl-fluoro-phosphate | (CH₃)₂CH—O—P(=O)(F)—O—CH(CH₃)₂ | 184.15 | Carboxypeptidase<br>Chymotrypsin<br>Complement<br>Elastase<br>Endoproteinase<br>Kallikrein<br>Plasmin<br>Thrombin<br>Pronase<br>Proteinase |
| 2 | 3,4-Dichloro-isocoumarin | 3,4-dichloroisocoumarin structure | 215.03 | Thrombin<br>Papain<br>Plasmin |
| 3 | Phenylmethanesulfonyl fluoride | benzyl-SO₂-F | 174.19 | Thrombin<br>Elastase<br>Plasmin<br>Proteinase |

TABLE 47

Elastase (pancreas) inhibitor

| No. | Name | Structural formula | Molecular weight | Protease to be inhibited |
|---|---|---|---|---|
| 1 | Diisorpropyl-fluoro-phosphate | (CH₃)₂CH—O—P(=O)(F)—O—CH(CH₃)₂ | 184.15 | Carboxypeptidase<br>Chymotrypsin<br>Complement<br>Elastase<br>Endoproteinase<br>Kallikrein<br>Plasmin<br>Thrombin<br>Pronase<br>Proteinase |
| 2 | 3,4-Dichloro-isocoumarin | 3,4-dichloroisocoumarin structure | 215.03 | Thrombin<br>Papain<br>Plasmin |

TABLE 48

Endoproteinase Arg-C inhibitor

| No. | Name | Structural formula | Molecular weight | Protease to be inhibited |
|---|---|---|---|---|
| 1 | Diisopropyl-fluorophosphate | 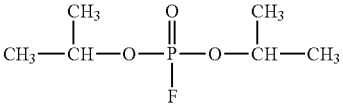 | 184.15 | Carboxypeptidase Chymotrypsin Complement Elastase Endoproteinase Kallikrein Plasmin Thrombin Pronase Proteinase |
| 2 | 3,4-Dichloro-isocoumarin | 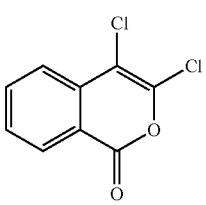 [SMILES: O=c1oc(Cl)c(Cl)c2ccccc12] | 215.03 | Thrombin Papain Plasmin |

TABLE 49

Endoproteinase Glu-C inhibitor

| No. | Name | Structural formula | Molecular weight | Protease to be inhibited |
|---|---|---|---|---|
| 1 | Diisopropyl-fluoro-phosphate | 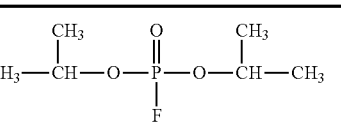 | 184.15 | Carboxypeptidase Chymotrypsin Complement Elastase Endoproteinase Kallikrein Plasmin Thrombin Pronase Proteinase |

TABLE 50

Endoproteinase Lys-C inhibitor

| No. | Name | Structural formula | Molecular weight | Protease to be inhibited |
|---|---|---|---|---|
| 1 | Diisopropyl-fluoro-phosphate | 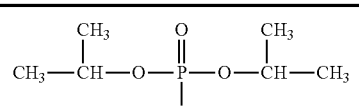 | 184.15 | Carboxypeptidase Chymotrypsin Complement Elastase Endoproteinase Kallikrein Plasmin Thrombin Pronase Proteinase |
| 2 | 3,4-Dichloro-isocoumarin | 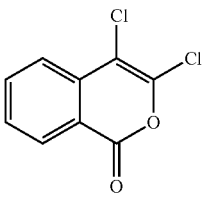 [SMILES: O=c1oc(Cl)c(Cl)c2ccccc12] | 215.03 | Thrombin Papain Plasmin |

TABLE 50-continued

Endoproteinase Lys-C inhibitor

| No. | Name | Structural formula | Molecular weight | Protease to be inhibited |
|---|---|---|---|---|
| 3 | Leupeptin | 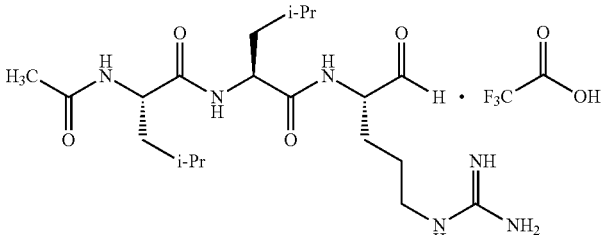 | 426.55 | Plasmin<br>Trypsin<br>Papain<br>Calpine<br>Cathepsin B<br>Thrombin<br>Kallikrein<br>Endoproteinase<br>Chymotrypsin<br>Proteasome (β2) |

TABLE 51

Ficin inhibitor

| No. | Name | Structural formula | Molecular weight | Protease to be inhibited |
|---|---|---|---|---|
| 1 | E-64 | 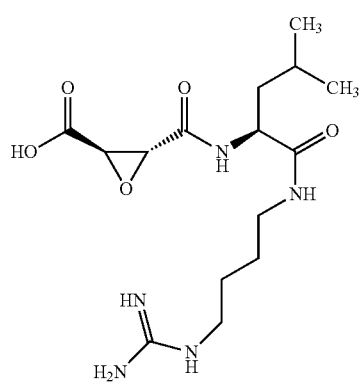 [SMILES: CC(C)C[C@H](NC(=O)[C@@H]1O[C@H]1C(=O)O)C(=O)NCCCCNC(=N)N] | 357.41 | Cathepsin B<br>Ficin<br>Papain<br>Bromelain |
| 2 | N-Ethyl-maleimide | 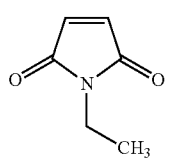 | 125.13 | Calpine<br>Ficin |
| 3 | N-p-Tosyl-L-phenil-alanine chloromethyl ketone | 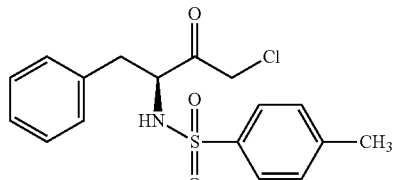 | 351.85 | Papain<br>Chymotrypsin<br>Ficin<br>Bromelain |
| 4 | Sodium iodoacetate | 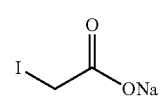 | 207.93 | Carboxypeptidase P<br>Bromelain<br>Ficin<br>Cathepsin |

TABLE 51-continued

| | | Ficin inhibitor | | |
|---|---|---|---|---|
| No. | Name | Structural formula | Molecular weight | Protease to be inhibited |
| 5 | Nα-Tosyl-L-lysine chloromethyl ketone hydrochloride | 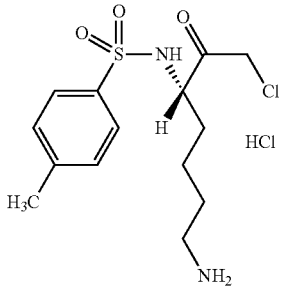 [SMILES: Cc1ccc(S(=O)(=O)N[C@@H](CCCCN)C(=O)CCl)cc1 ; Cl] | 369.31 | |

TABLE 52

| | | Granzyme B inhibitor | | |
|---|---|---|---|---|
| No. | Name | Structural formula | Molecular weight | Protease to be inhibited |
| 1 | Antipain dihydrochloride from microbial source | 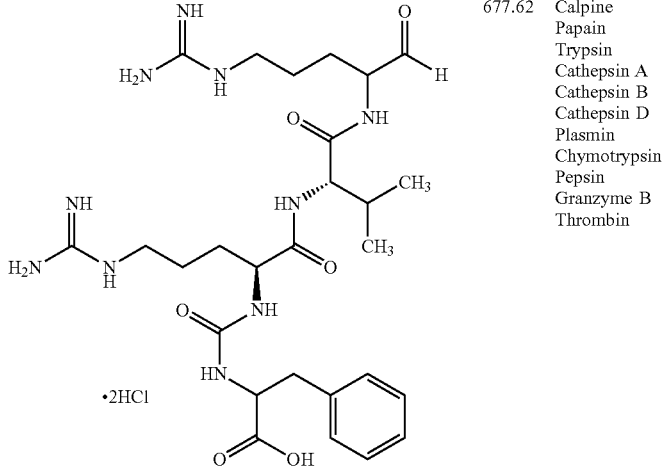 | 677.62 | Calpine<br>Papain<br>Trypsin<br>Cathepsin A<br>Cathepsin B<br>Cathepsin D<br>Plasmin<br>Chymotrypsin<br>Pepsin<br>Granzyme B<br>Thrombin |
| 2 | 3,4-Dichloroisocoumarin | 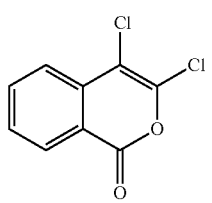 [SMILES: O=c1oc(Cl)c(Cl)c2ccccc12] | 215.03 | Thrombin<br>Papain<br>Plasmin |

TABLE 53

Kallikrein (tissue) inhibitor

| No. | Name | Structural formula | Molecular weight | Protease to be inhibited |
|---|---|---|---|---|
| 1 | Diisopropyl-fluoro-phosphate | (structure: (CH₃)₂CH—O—P(=O)(F)—O—CH(CH₃)₂) | 184.15 | Carboxypeptidase Chymotrypsin Complement Elastase Endoproteinase Kallikrein Plasmin Thrombin Pronase Proteinase |
| 2 | 3,4-Dichloro-isocoumarin | (structure: 3,4-dichloroisocoumarin) | 215.03 | Thrombin Papain Plasmin |
| 3 | Leupeptin | (structure: Ac-Leu-Leu-Arg-al · TFA) | 426.55 | Plasmin Trypsin Papain Calpine Cathepsin B Thrombin Kallikrein Endoproteinase Chymotrypsin Proteasome (β2) |

TABLE 54

Kallikrein (plasma) inhibitor

| No. | Name | Structural formula | Molecular weight | Protease to be inhibited |
|---|---|---|---|---|
| 1 | Gabexate mesylate | (structure: ethyl 4-((6-guanidinohexanoyl)oxy)benzoate · methanesulfonate) | 417.48 | |

TABLE 55

Leucine aminopeptidase inhibitor

| No. | Name | Structural formula | Molecular weight | Protease to be inhibited |
|---|---|---|---|---|
| 1 | Actinonin | | 385.5 | |
| 2 | Bestatin hydrochloride | HCl | 344.83 | Aminopeptidase B |

TABLE 56

Leucine aminopeptidase (cytosol) inhibitor

| No. | Name | Structural formula | Molecular weight | Protease to be inhibited |
|---|---|---|---|---|
| 1 | Actinonin | | 385.5 | |
| 2 | Amastatin hydrochloride hydrate | HCl ·H$_2$O | 511.01 (anhydrous basis) | |

TABLE 56-continued

Leucine aminopeptidase (cytosol) inhibitor

| No. | Name | Structural formula | Molecular weight | Protease to be inhibited |
|---|---|---|---|---|
| 3 | Ethylene glycol-bis(2-aminoethyl ether)-N,N,N',N'-tetraacetic acid | | 380.35 | |
| 4 | Ethylenediaminetetra acetic acid disodium salt dihydrate | ·2H₂O  R = H or Na (2:2) | 372.24 | |

TABLE 57

Leucine aminopeptidase (cytosol) inhibitor (Continued)

| No. | Name | Structural formula | Molecular weight | Protease to be inhibited |
|---|---|---|---|---|
| 5 | Diethylene triamine-pentaacetic acid | | 393.35 | |
| 6 | 3,4-Dichloro-isocoumarin | | 215.03 | Thrombin Papain Plasmin |
| 7 | 1,10-Phenanthroline monohydrate | ·H₂O | 198.22 | Carboxypeptidase A Carboxypeptidase B Dispase Leucine aminopeptidase Thermolysin |

TABLE 57-continued

Leucine aminopeptidase (cytosol) inhibitor (Continued)

| No. | Name | Structural formula | Molecular weight | Protease to be inhibited |
|-----|------|--------------------|------------------|--------------------------|
| 8 | Bestatin hydrochloride | (structure shown) HCl | 344.83 | AminopeptidaseB |

TABLE 58

Leucine aminopeptidase (microsome) inhibitor

| No. | Name | Structural formula | Molecular weight | Protease to be inhibited |
|-----|------|--------------------|------------------|--------------------------|
| 1 | Actinonin | (structure shown) | 385.5 | |
| 2 | Amastatin hydrochloride hydrate | (structure shown) HCl · $H_2O$ | 511.01 (anhydrous basis) | |
| 3 | Bestatin hydrochloride | (structure shown) HCl | 344.83 | Aminopeptidase B |

TABLE 59

Matrix aminopeptidase inhibitor

| No. | Name | Structural formula | Molecular weight | Protease to be inhibited |
|---|---|---|---|---|
| 1 | GM6001 | | 388.46 | |

TABLE 60

Metalloprotease inhibitor

| No. | Name | Structural formula | Molecular weight | Protease to be inhibited |
|---|---|---|---|---|
| 1 | Epiamastatin hydrochloride | | 474.55 | |

TABLE 61

Papain inhibitor

| No. | Name | Structural formula | Molecular weight | Protease to be inhibited |
|---|---|---|---|---|
| 1 | E-64 | | 357.41 | |

TABLE 61-continued

| | Papain inhibitor | | |
|---|---|---|---|
| No. Name | Structural formula | Molecular weight | Protease to be inhibited |
| 2 Gly-Gly-Tyr-Arg | (structure) | 451.48 | |
| 3 Antipain dihydro-chloride from microbial source | (structure) ·2HCl | 677.62 | Calpine<br>Papain<br>Trypsin<br>Cathepsin A<br>Cathepsin B<br>Cathepsin D<br>Plasmin<br>Chymotrypsin<br>Pepsin<br>Granzyme B<br>Thrombin |
| 4 Ebselen | (structure) | 274.18 | |

TABLE 62

Papain inhibitor (Continued)

| No. | Name | Structural formula | Molecular weight | Protease to be inhibited |
|---|---|---|---|---|
| 5 | Chymostatin | 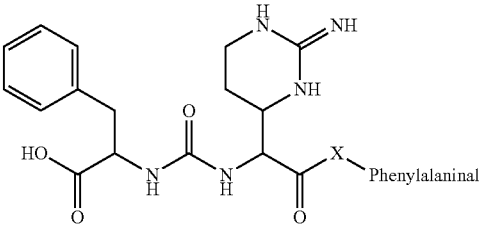 Chymostatin A X = Leu<br>Chymostatin B X = Val<br>Chymostatin C X = Ile | A: MW = 607.7<br>B: MW = 593.7<br>C: MW = 607.7 | Chymotrypsin<br>Papain<br>Chymotrypsin-like serine proteinase<br>Cathepsin A, B, C, B, H, L<br>Proteasome (β5) |
| 6 | Cystamine dihydrochloride | 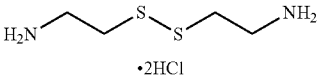 | 225.2 | |
| 7 | 3,4-Dichloroisocoumarin | 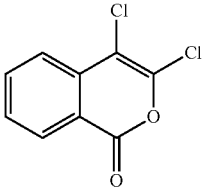 [SMILES: O=c1oc(Cl)c(Cl)c2ccccc12] | 215.03 | Thrombin<br>Papain<br>Plasmin |
| 8 | N-p-Tosyl-L-phenilalanine chloromethyl ketone | 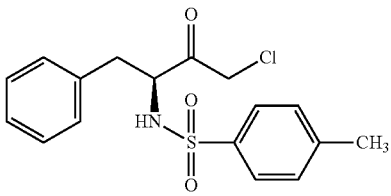 [SMILES: Cc1ccc(S(=O)(=O)N[C@@H](Cc2ccccc2)C(=O)CCl)cc1] | 351.85 | Papain<br>Chymotrypsin<br>Ficin<br>Bromelain |
| 9 | Leupeptin | 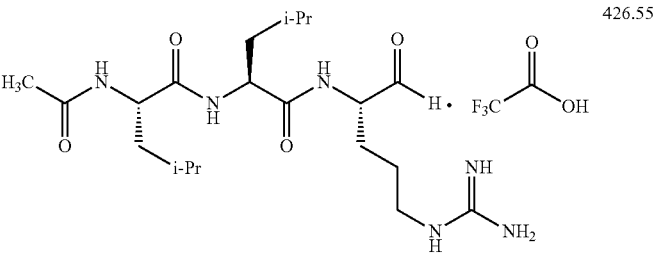 | 426.55 | Plasmin<br>Trypsin<br>Papain<br>Calpine<br>Cathepsin B<br>Thrombin<br>Kallikrein<br>Endoproteinase<br>Chymotrypsin<br>Proteasome (β2) |

TABLE 63

Pepsin inhibitor

| No. | Name | Structural formula | Molecular weight | Protease to be inhibited |
|---|---|---|---|---|
| 1 | Pepstatin A | | 685.89 | Cathepsin D |

TABLE 64

Plasmin inhibitor

| No. | Name | Structural formula | Molecular weight | Protease to be inhibited |
|---|---|---|---|---|
| 1 | Diisopropylfluorophosphate | | 184.15 | Carboxypeptidase Chymotrypsin Complement Elastase Endoproteinase Kallikrein Plasmin Thrombin Pronase Proteinase |
| 2 | Elastatinal | | 512.56 | |
| 3 | 4-(2-Aminoethyl)benzenesulfonyl fluoride hydrochloride (AEBSF) | | 239.69 | Plasmin Trypsin Chymotrypsin |
| 4 | 6-Aminocaproic acid | | 131.17 | |

TABLE 64-continued

Plasmin inhibitor

| No. | Name | Structural formula | Molecular weight | Protease to be inhibited |
|---|---|---|---|---|
| 5 | Antipain dihydrochloride from microbial source | 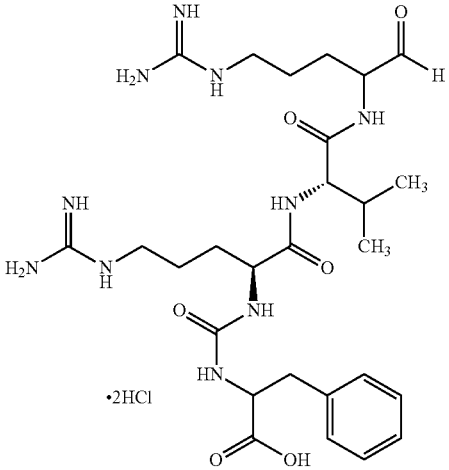 [SMILES: CC(C)[C@H](NC(=O)[C@H](CCCNC(=N)N)NC(=O)NC(Cc1ccccc1)C(=O)O)C(=O)NC(C=O)CCCNC(=N)N] | 677.62 | Calpine<br>Papain<br>Trypsin<br>Cathepsin A<br>Cathepsin B<br>Cathepsin D<br>Plasmin<br>Chymotrypsin<br>Pepsin<br>Granzyme B<br>Thrombin |

TABLE 65

Plasmin inhibitor (Continued)

| No. | Name | Structural formula | Molecular weight | Protease to be inhibited |
|---|---|---|---|---|
| 6 | 3,4-Dichloroisocoumarin | | 215.03 | Thrombin<br>Papain<br>Plasmin |
| 7 | Phenylmethanesulfonyl fluoride | | 174.19 | Thrombin<br>Elastase<br>Plasmin<br>Proteinase |
| 8 | Gabexate mesylate | | 417.48 | |

TABLE 65-continued

Plasmin inhibitor (Continued)

| No. | Name | Structural formula | Molecular weight | Protease to be inhibited |
|---|---|---|---|---|
| 9 | Leupeptin | 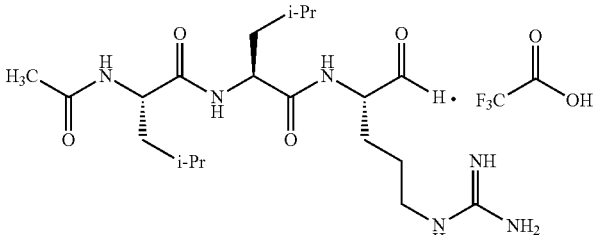 | 426.55 | Plasmin<br>Trypsin<br>Papain<br>Calpine<br>Cathepsin B<br>Thrombin<br>Kallikrein<br>Endoproteinase<br>Chymotrypsin<br>Proteasome (β2) |

TABLE 66

Thrombin inhibitor

| No. | Name | Structural formula | Molecular weight | Protease to be inhibited |
|---|---|---|---|---|
| 1 | Diisopropyl-fluorophos-phate | 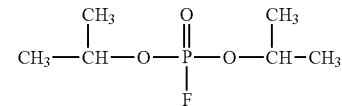 | 184.15 | Carboxypeptidase<br>Chymotrypsin<br>Complement<br>Elastase<br>Endoproteinase<br>Kallikrein<br>Plasmin<br>Thrombin<br>Pronase<br>Proteinase |
| 2 | Nα-Tosyl-L-lysine chloromethyl ketone hydrochloride | 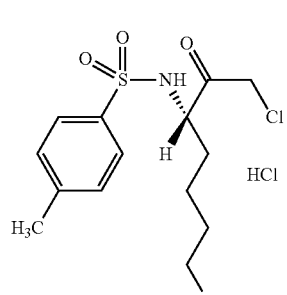 | 369.31 | |
| 3 | 4-(2-Aminoethyl)benzenesulfonyl fluoride hydrochloride (AEBSF) | 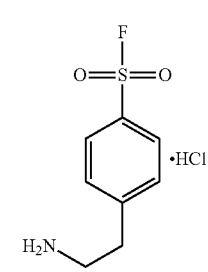 | 239.69 | |

TABLE 66-continued

Thrombin inhibitor

| No. | Name | Structural formula | Molecular weight | Protease to be inhibited |
|---|---|---|---|---|
| 4 | Antipain dihydrochloride from microbial source | 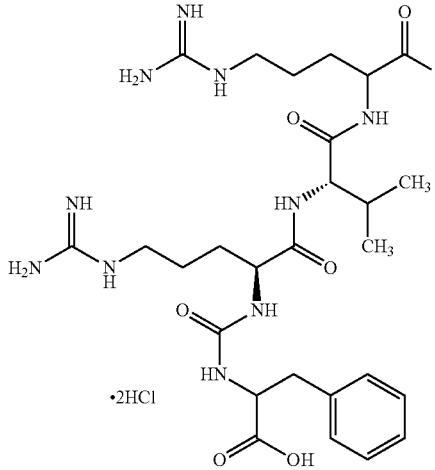 | 677.62 | Calpine<br>Papain<br>Trypsin<br>Cathepsin A<br>Cathepsin B<br>Cathepsin D<br>Plasmin<br>Chymotrypsin<br>Pepsin |

TABLE 67

Thrombin inhibitor (Continued)

| No. | Name | Structural formula | Molecular weight | Protease to be inhibited |
|---|---|---|---|---|
| 5 | 3,4-Dichloroisocoumarin | 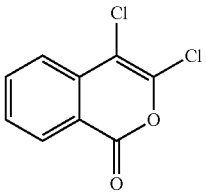 [SMILES: O=c1oc(Cl)c(Cl)c2ccccc12] | 215.03 | Thrombin<br>Papain<br>Plasmin |
| 6 | Phenylmethanesulfonyl fluoride | 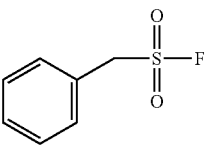 [SMILES: O=S(=O)(F)Cc1ccccc1] | 174.19 | Thrombin<br>Elastase<br>Plasmin<br>Proteinase |
| 7 | Gabexate mesylate | 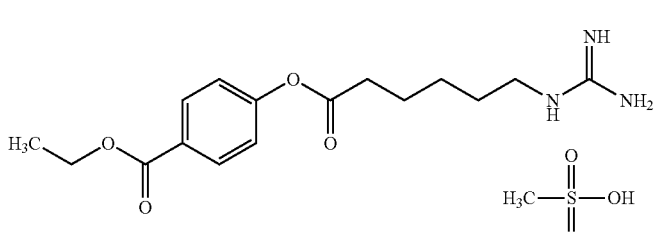 | 417.48 | |

TABLE 67-continued

Thrombin inhibitor (Continued)

| No. | Name | Structural formula | Molecular weight | Protease to be inhibited |
|---|---|---|---|---|
| 8 | Leupeptin | | 426.55 | Plasmin<br>Trypsin<br>Papain<br>Calpine<br>Cathepsin B<br>Thrombin<br>Kallikrein<br>Endoproteinase<br>Chymotrypsin<br>Proteasome (β2) |

TABLE 68

Thermolysin inhibitor

| No. | Name | Structural formula | Molecular weight | Protease to be inhibited |
|---|---|---|---|---|
| 1 | Ethylene glycol-bis (2-aminoethyl ether)-N,N,N',N'-tetraacetic acid | | 380.35 | |
| 2 | Ethylenediaminetetraacetic acid disodium salt dihydrate | R = H or Na (2:2), ·2H$_2$O | 372.24 | Carboxypeptidase A<br>Carboxypeptidase B<br>Dispase<br>Collagenase |
| 3 | Diethylene triaminepentaacetic acid | | 393.35 | |
| 4 | 1,10 Phenanthroline monohydrate | ·H$_2$O | 198.22 | Carboxypeptidase A<br>Carboxypeptidase B<br>Dispase<br>Leucine aminopeptidase<br>Thermolysin |

TABLE 68-continued

Thermolysin inhibitor

| No. | Name | Structural formula | Molecular weight | Protease to be inhibited |
|---|---|---|---|---|
| 5 | Phosphor-amidon disodium salt | | 587.47 | |

TABLE 69

Trypsin inhibitor

| No. | Name | Structural formula | Molecular weight | Protease to be inhibited |
|---|---|---|---|---|
| 1 | 4-(2-Aminoethyl)benzene-sulfonyl fluoride hydro-chloride | | 239.69 | Plasmin<br>Trypsin<br>Chymotrypsin |
| 2 | Antipain dihydro-chloride from microbial source | | 677.62 | Calpine<br>Papain<br>Trypsin<br>Cathepsin A<br>Cathepsin B<br>Cathepsin D<br>Plasmin<br>Chymotrypsin<br>Pepsin<br>Granzyme B<br>Thrombin |

TABLE 69-continued

Trypsin inhibitor

| No. | Name | Structural formula | Molecular weight | Protease to be inhibited |
|---|---|---|---|---|
| 3 | Boldine | (structure shown) | 327.37 | |

TABLE 70

Pronase E inhibitor

| No. | Name | Structural formula | Molecular weight | Protease to be inhibited |
|---|---|---|---|---|
| 1 | EDTA disodium salt | (structure shown) R = H or Na (2:2) | 372.24 | Carboxypeptidase A<br>Carboxypeptidase B<br>Dispase<br>Collagenase |
| 2 | Diisopropyl-fluorophosphate | (structure shown) | 184.15 | Carboxypeptidase<br>Chymotrypsin<br>Complement<br>Elastase<br>Endoproteinase<br>Kallikrein<br>Plasmin<br>Thrombin<br>Pronase<br>Proteinase |

TABLE 71

Procaspase 3 inhibitor

| No. | Name | Structural formula | Molecular weight | Protease to be inhibited |
|---|---|---|---|---|
| 1 | N-Acetyl-Glu-Ser-Met-Asp-al (Ac-ESMD-CHO) | (structure shown) | 506.53 | |

TABLE 71-continued

Procaspase 3 inhibitor

| No. | Name | Structural formula | Molecular weight | Protease to be inhibited |
|---|---|---|---|---|
| 2 | N-Acetyl-Ile-Glu-Thr-Asp-al (Ac-IETD-CHO) | | 502.52 | |

TABLE 72

Proteinase K inhibitor

| No. | Name | Structural formula | Molecular weight | Protease to be inhibited |
|---|---|---|---|---|
| 1 | Phenylmethanesulfonyl fluoride | | 174.19 | Thrombin<br>Elastase<br>Plasmin<br>Proteinase |
| 2 | Diisopropylfluorophosphate | | 184.15 | Carboxypeptidase<br>Chymotrypsin<br>Complement<br>Elastase<br>Endoproteinase<br>Kallikrein<br>Plasmin<br>Thrombin<br>Pronase<br>Proteinase |

TABLE 73

Renin inhibitor

| No. | Name | Structural formula | Molecular weight | Protease to be inhibited |
|---|---|---|---|---|
| 1 | Pepstatin A | | 685.89 | Cathepsin D |

TABLE 74

Caspase inhibitor

| No. | Name | Structural formula | Molecular weight | Protease to be inhibited |
|---|---|---|---|---|
| 1 | BOC-Asp(OMe)-fluoromethyl ketone (Boc-D-FMK) | 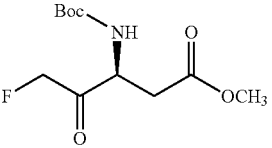 [SMILES: COC(=O)C[C@H](NC(=O)OC(C)(C)C)C(=O)CF] | 263.26 | |
| 2 | Z-Ala-Glu(OMe)-Val-Asp(OMe)-fluoromethyl ketone (Z-AEVD-FMK) | 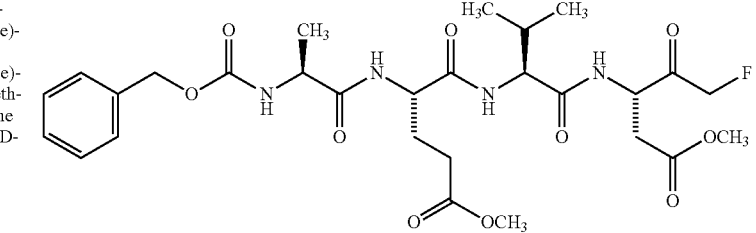 | 610.63 | |

TABLE 75

Caspase 1 inhibitor

| No. | Name | Structural formula | Molecular weight | Protease to be inhibited |
|---|---|---|---|---|
| 1 | N-Acetyl-Trp-Glu-His-Asp-al (AC-WEHD-CHO) | 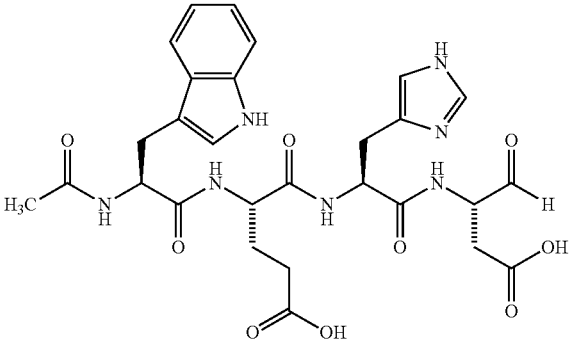 [SMILES: CC(=O)N[C@@H](Cc1c[nH]c2ccccc12)C(=O)N[C@@H](CCC(=O)O)C(=O)N[C@@H](Cc1c[nH]cn1)C(=O)N[C@H](C=O)CC(=O)O] | 611.6 | |

TABLE 76

Caspase 2 inhibitor

| No. | Name | Structural formula | Molecular weight | Protease to be inhibited |
|---|---|---|---|---|
| 1 | N-Acetyl-Val-Asp-Val-Ala-Asp-CHO (Ac-VDVAD-CHO) | 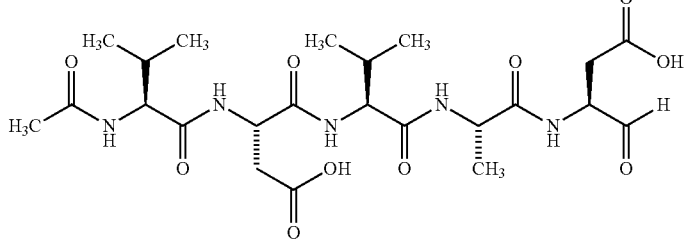 | 543.52 | |

TABLE 76-continued

Caspase 2 inhibitor

| No. | Name | Structural formula | Molecular weight | Protease to be inhibited |
|-----|------|--------------------|------------------|--------------------------|
| 2 | Z-Val-Asp(O—Me)-Val-Ala-Asp(O—Me) fluoromethyl ketone (Z-VDVAD-FMK) | | 695.73 | |

TABLE 77

Caspase 3 inhibitor

| No. | Name | Structural formula | Molecular weight | Protease to be inhibited |
|-----|------|--------------------|------------------|--------------------------|
| 1 | N-Acetyl-Glu-Ser-Met-Asp-al (Ac-ESMD-CHO) | | 506.53 | |
| 2 | Z-Asp(OMe)-Gln-Met-Asp(OMe) fluoromethyl ketone | | 685.72 | |
| 3 | N-Acetyl-Asp-Glu-Val-Asp-al (Ac-DEVD-CHO) | | 502.47 | |

TABLE 77-continued

Caspase 3 inhibitor

| No. | Name | Structural formula | Molecular weight | Protease to be inhibited |
|---|---|---|---|---|
| 4 | N-Acetyl-Ile-Glu-Thr-Asp-al (Ac-IETD-CHO) | | 502.52 | |

TABLE 78

Caspase 5 inhibitor

| No. | Name | Structural formula | Molecular weight | Protease to be inhibited |
|---|---|---|---|---|
| 1 | N-Acetyl-Trp-Glu-His-Asp-al (Ac-WEHD-CHO) | | 611.6 | |

TABLE 79

Caspase 6 inhibitor

| No. | Name | Structural formula | Molecular weight | Protease to be inhibited |
|---|---|---|---|---|
| 1 | N-Acetyl-Val Glu-Ile-Asp-al | | 500.54 | |

TABLE 79-continued

Caspase 6 inhibitor

| No. | Name | Structural formula | Molecular weight | Protease to be inhibited |
|---|---|---|---|---|
| 2 | Z-Asp(OMe)-Gln-Met-Asp(OMe) fluoromethyl ketone | | 685.72 | |
| 3 | Z-Val-Glu(O—Me)-Ile-Asp(O—Me) fluoromethyl ketone | | 652.71 | |

TABLE 80

Caspase 7 inhibitor

| No. | Name | Structural formula | Molecular weight | Protease to be inhibited |
|---|---|---|---|---|
| 1 | Z-Asp(O—Me)-Glu(O—Me)-Val-Asp(O—Me) fluoromethyl ketone (Z-DEVD-FMK) | | 668.66 | |

TABLE 81

Caspase 8 inhibitor

| No. | Name | Structural formula | Molecular weight | Protease to be inhibited |
|---|---|---|---|---|
| 1 | Z-Ile-Glu(O—Me)-Thr-Asp(O—Me) fluoromethyl ketone (Z-IETD-FMK) | | 654.68 | |

TABLE 81-continued

Caspase 8 inhibitor

| No. | Name | Structural formula | Molecular weight | Protease to be inhibited |
|-----|------|--------------------|------------------|--------------------------|
| 2 | Z-Leu-Glu(OMe)-Thr-Asp(OMe)-fluoromethyl ketone (Z-LETD-FMK) | | 655.69 | |
| 3 | N-Acetyl-Ile-Glu-Thr-Asp-al (Ac-IETD-CHO) | | 502.52 | |

TABLE 82

Caspase 9 inhibitor

| No. | Name | Structural formula | Molecular weight | Protease to be inhibited |
|-----|------|--------------------|------------------|--------------------------|
| 1 | Z-Leu-Glu(O—Me)-His-Asp(O—Me) fluoromethyl ketone (Z-LE(OMe)HD(OMe)-FMK, Z-LEHD-FMK) | | 690.72 | |

TABLE 83

Caspase 13 inhibitor

| No. | Name | Structural formula | Molecular weight | Protease to be inhibited |
|-----|------|--------------------|------------------|--------------------------|
| 1 | Z-Leu-Glu(OMe)-Glu(OMe)-Asp(OMe)-fluoromethyl ketone (Z-LEED-FMK) | | 696.72 | |

TABLE 84

Cytosol alanyl aminopeptidase inhibitor

| No. | Name | Structural formula | Molecular weight | Protease to be inhibited |
|-----|------|--------------------|------------------|--------------------------|
| 1 | Puromycin | | 471.51 | Dipeptidyl peptidase II<br>Cytosol alanyl aminopeptidase |
| 2 | Opiorphin | | 692.77 | Enkephalinase<br>Neprilysin<br>Dipeptidyl peptidase III<br>Cytosol alanyl aminopeptidase |

TABLE 85

Enkephalinase inhibitor

| No. | Name | Structural formula | Molecular weight | Protease to be inhibited |
|---|---|---|---|---|
| 1 | Opiorphin | (structure) | 692.77 | Enkephalinase Neprilysin Dipeptidyl peptidase III Cytosol alanyl aminopeptidase |

TABLE 86

Neprilysin inhibitor

| No. | Name | Structural formula | Molecular weight | Protease to be inhibited |
|---|---|---|---|---|
| 1 | Opiorphin | (structure) | 692.77 | Enkephalinase Neprilysin Dipeptidyl peptidase III Cytosol alanyl aminopeptidase |

It is noted that in the above descriptions, proteasome inhibitors and protease inhibitors other than the proteasome inhibitors are separately discussed for convenience, but a compound is also known which can inhibit the activities of both a proteasome and a protease other than proteasomes. Therefore, a protein-degradation inducing tag having an affinity with both a proteasome and a protease other than proteasomes can be obtained when such a compound is used.

Examples of the compound which can inhibit the activities of both a proteasome and a protease other than proteasomes are shown in the following table 87. However, the compound which can inhibit the activities of both a proteasome and a protease other than proteasomes shall not be limited to these examples.

TABLE 87

| No. | Name | Structural formula | Molecular weight | Protease to be inhibited |
|-----|------|-------------------|------------------|--------------------------|
| 1 | Calpain Inhibitor I (ALLN, Ac-LLnL-CHO, MG-101) | | 383.53 | Proteasome Cathepsin B Cathepsin L Calpine |
| 2 | Calpain Inhibitor II | | 401.56 | Proteasome Cathepsin B Calpine |
| 3 | Leupeptin | | 426.55 | Plasmin Trypsin Papain Calpine Cathepsin B Thrombin Kallikrein Endoproteinase Chymotrypsin Proteasome ($\beta$2) |
| 4 | Chymostatin | Chymostatin A X = Leu<br>Chymostatin B X = Val<br>Chymostatin C X = Ile | A: MW = 607.7<br>B: MW = 593.7<br>C: MW = 607.7 | Proteasome ($\beta$5) Chymotrypsin Papain Chymotrypsin-like serine proteinase Cathepsin A, B, C, B, H, L |
| 5 | clasto-Lactacystin-$\beta$-lactone | | 213.23 | tripeptidyl peptidase II chlamydial protease-like activity factor |

In another embodiment, a proteasome activator can be used as a protein-degradation inducing tag. A proteasome activator is a compound having an affinity with a proteasome (a protease complex) without inhibiting degradation of a protein by the proteasome, and can be used as a protein-degradation inducing tag.

Examples of the proteasome activator are shown in the following Tables 88 to 90. However, the proteasome activator which can be used for producing a protein-degradation inducing tag shall not be limited to these examples.

TABLE 88

20S proteasome activator

| No. | Generic name/ Product name | Structural formula | Molecular weight |
|---|---|---|---|
| 1 | Oleuropein | 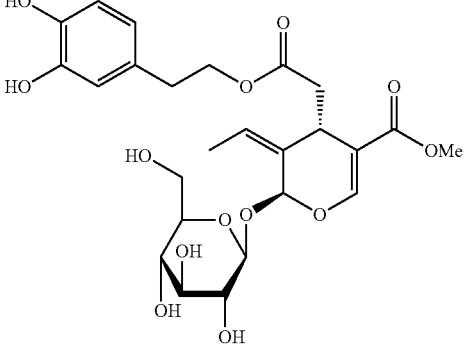 | 540.51 |
| 2 | Betulinic acid | 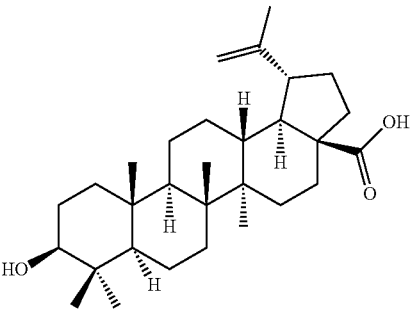 | 456.70 |

TABLE 89

19S/11S (PA28) proteasome activator

| No. | Generic name/ Product name | Structural formula | Molecular weight |
|---|---|---|---|
| 1 | IU1 (Usp 14 inhibitor) | 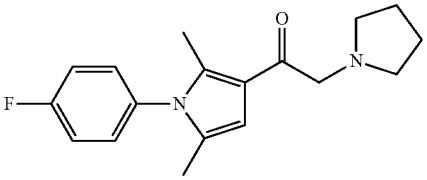 [SMILES: Cc1cc(C(=O)CN2CCCC2)c(C)n1-c1ccc(F)cc1] | 300.38 |
| 2 | b-AP-15 (Usp 14 and Uch-L5 inhibitor) | 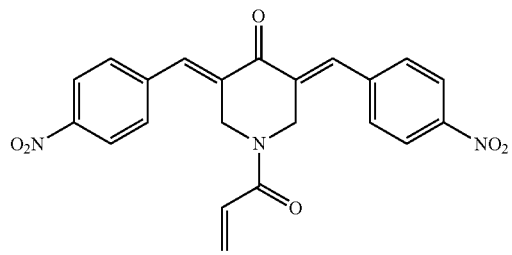 [SMILES: C=CC(=O)N1C/C(=C\c2ccc([N+](=O)[O-])cc2)C(=O)/C(=C/c2ccc([N+](=O)[O-])cc2)C1] | 419.39 |

TABLE 89-continued
19S/11S (PA28) proteasome activator
| No. | Generic name/ Product name | Structural formula | Molecular weight |
|---|---|---|---|
| 3 | 17-AAG | 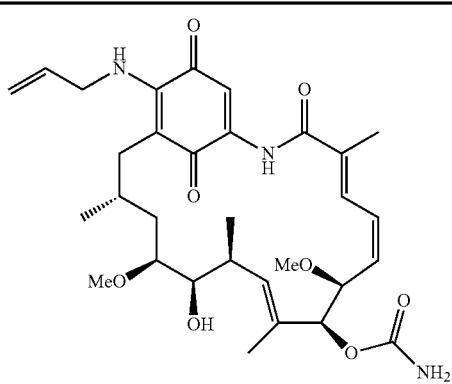 | 585.7 |
| 4 | PU3 | 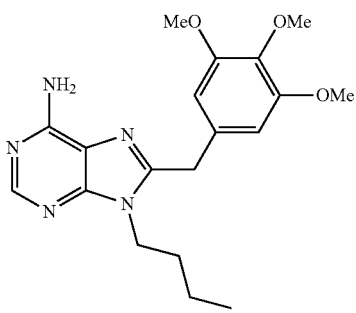 [SMILES: CCCCn1c(Cc2cc(OC)c(OC)c(OC)c2)nc2c(N)ncnc21] | 371.44 |
| 5 | PU-H71 | 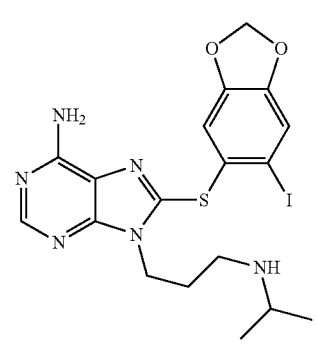 [SMILES: CC(C)NCCCn1c(Sc2cc3c(cc2I)OCO3)nc2c(N)ncnc21] | 512.37 |
| 6 | NVP-AUY922 | 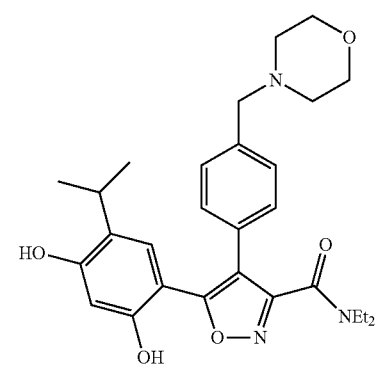 | 493.60 |

TABLE 90

19S/11S (PA28) proteasome activator (Continued)

| No. | Generic name/ Product name | Structural formula | Molecular weight |
|---|---|---|---|
| 7 | SNX-5422 | | 521.54 |
| 8 | HBX 19,818 | | 407.94 |
| 9 | LS1 | | 518.53 |
| 10 | LDN91946 | | 314.32 |
| 11 | P005091 | | 348.21 |
| 12 | P0040429 | | 484.38 |

Among the protein-degradation inducing tags as mentioned above, in particular, the protein-degradation inducing tag having an affinity with a 26S proteasome is preferable. The intracellular proteasome is generally present in a state of the 26S proteasome in which two 19S proteasomes are bonded to a 20S proteasome. Therefore, use of the protein-degradation inducing tag having an affinity with the 26S proteasome can lead the intracellular Ras protein to degradation more efficiently.

(Form of Conjugate of Ras Protein Affinity Molecule and Protein-Degradation Inducing Tag)

There is no particular limitation for the form of a conjugate of the Ras protein affinity molecule and the protein-degradation inducing tag as long as the affinity of the Ras protein affinity molecule with the Ras protein, and the affinity of the protein-degradation inducing tag with the protease are maintained. It is noted that when both the Ras protein affinity molecule and the protein-degradation inducing tag are proteins, the both proteins can be fused to each other to synthesize a fusion protein, but such fusion proteins are not included in the "conjugate".

The Ras protein-degradation inducing molecule may have, for example, a structure in which at least one Ras protein affinity molecule is linked to at least one protein-degradation inducing tag. The Ras protein-degradation inducing molecule may have a structure in which one Ras protein affinity molecule is linked to one protein-degradation inducing tag, or may have a structure in which one Ras protein affinity molecule is linked to a plurality of protein-degradation inducing tags, or may have a structure in which a plurality of Ras protein affinity molecules are linked to one protein-degradation inducing tag, or may have a structure in which a plurality of Ras protein affinity molecules are linked to a plurality of protein-degradation inducing tags. In a certain embodiment, the Ras protein-degradation inducing molecule has a structure in which one Ras protein affinity molecule is linked to one protein-degradation inducing tag.

A position in the Ras protein affinity molecule at which the protein-degradation inducing tag is linked to the Ras protein affinity molecule is not particularly limited as long as the affinity with the Ras protein is maintained. Meanwhile, a position in the protein-degradation inducing tag at which the Ras protein affinity molecule is linked to the protein-degradation inducing tag is not particularly limited as long as the affinity with the protease is maintained. For example, when the protein-degradation inducing tag has, as described above, a structure in which the active site of a protease inhibitor (for example, a proteasome inhibitor) is replaced with another structural moiety, the protein-degradation inducing tag can be linked to the Ras protein affinity molecule at this replaced another structural moiety. Specifically, when the active site of the protease inhibitor is replaced with a carboxy group, the protein-degradation inducing tag can be linked to the Ras protein affinity molecule via a carboxy group.

It is noted that the Ras protein affinity molecule and the protein-degradation inducing tag may have a structure in which they can be linked to each other. When it is difficult to directly link the Ras protein affinity molecule to the protein-degradation inducing tag, it is considered that a structure capable of linking them to each other is introduced into at least one of the Ras protein affinity molecule and the protein-degradation inducing tag. For example, as the Ras protein affinity molecule, a well-known molecule having an affinity with the Ras protein can be used, but it is assumed to be difficult to directly link this well-known molecule to the protein-degradation inducing tag. In such a case, a structure which can be linked to the protein-degradation inducing tag may be introduced into the well-known molecule, and used as the Ras protein affinity molecule.

<Pharmaceutical Composition>

The pharmaceutical composition of the present disclosure includes the Ras protein-degradation inducing molecule of the present disclosure. As described above, the Ras protein-degradation inducing molecule of the present disclosure can lead a Ras protein to degradation (knockdown) by a protease (for example, a proteasome), without ubiquitination of the Ras protein (in other words, in a ubiquitin-independent manner). Therefore, the pharmaceutical composition including Ras protein-degradation inducing molecule according to the present disclosure can be used for preventing or treating Ras protein-mediated diseases or conditions. The present disclosure can also provide a method for preventing or treating Ras protein-mediated diseases or conditions. The method includes administering the pharmaceutical composition including the Ras protein-degradation inducing molecule.

The Ras protein-mediated diseases or conditions are not particularly limited as long as the preventive effect or therapeutic effect can be expected by the Ras protein degradation. Examples of the Ras protein-mediated diseases or conditions are shown in Table 91. However, the Ras protein-mediated diseases or conditions shall not be limited to these examples.

TABLE 91

| | Disease or condition | References |
|---|---|---|
| Cancer | Pancreatic cancer | *British Journal of Cancer* vol.111, pp.817-822 (2014) |
| | Colorectal cancer | *The New England Journal of Medicine* vol. 359, pp.1757-1765 (2008) |
| | Lung cancer | *Annals of the American Thoracic Society* vol.6, pp.201-205 (2009) |
| | Gastric cancer | *Oncogene* vol.22, pp.6942-6945 (2003) |
| | Breast cancer | *Breast cancer Research and Treatment* vol.62, pp.51-62 (2000) |
| | Kidney cancer | *Cancer Research* vol.48, pp.5251-5255 (1988) |
| | Juvenile myelomonocytic leukemia (JMML) | *Blood* vol.125, pp.2753-2758 (2015) |
| | Thyroid tumor | *Official Journal of the Japan Association of Endocrine Surgeons and the Japanese Society of Thyroid Surgery* vol.31, pp.125-129 (2014) |
| | Melanoma | *Cancer Research* vol.66, pp.9483-9491 (2006) |
| | | *Trends in Molecular Medicine* vol.43, pp.38-45 (2011) |

TABLE 91-continued

| Disease or condition | | References |
|---|---|---|
| | Biliary tract cancer | *Journal of Clinical Oncology* vol.28, pp.3531-3540 (2010) |
| | Head and neck cancer | *Journal of the National Cancer Institute* vol.106, dju215 (2014) |
| | Esophageal cancer | *Annals of Surgical Oncology* vol.20, pp.S485-S491 (2013) |
| | Liver cancer | *Journal of Hepatology* vol.51, pp.725-733 (2010) |
| | Ovarian cancer | *BMC Cancer* vol.9 (111) (2009) |
| | Uterine cancer | *Gynecologic Oncology* vol.63, pp.238-246 (1996) |
| | Prostate cancer | *Journal of Cellular Biochemistry* vol.91, pp.13-25 (2004) |
| | Bladder cancer | *PloS ONE* vol.5, e13821 (2010) |
| Immune disease | Autoimmune disease | *Journal of Clinical Immunology* vol.35, pp.454-458 (2015) |
| | Rheumatoid arthritis | *The Open Rheumatoid Journal* vol.6, pp.259-272 (2012) |
| | RAS-related autoimmune lymphoproliferative disorders | *PNAS* vol.104, pp.8953-8958 (2007) *Blood* vol.117, pp.2887-2890 (2011) |
| Infection | Influenza | *Cancer Research* vol.61, pp.8188-8193 (2001) *PloS ONE* vol.6, e16324 (2011) *Seikagaku: The Journal of the Japanese Biochemical Society* vol.87, Issue 1 |
| | EBV infection | *Oncogene* vol.23, pp.8619-8628 (2004) |
| | HIV infection | *Journal of Biological Chemstry* vol.275, pp.16513-16517 (2000) |
| Neurologic disease | Alzheimer's disease | *Biochimica et Biophysica Acta* vol.1802, pp.396-405 (2010) *Neurobiology of Disease* vol.43, pp.38-45 (2011) |
| | Parkinson's disease | *Biochimica et Biophysica Acta* vol.1802, pp.396-405 (2010) |
| | ALS | *Biochimica et Biophysica Acta* vol.1802, pp.396-405 (2010) |
| RAS/MAPK syndrome | Noonan syndrome | *Human Molecular Genetics* vol.15, pp.R220-R226 (2006) |
| | Costello syndrome | *Genetics in Medicine* vol.14, pp.285-292 (2012) |
| | CFC syndrome | *Human Mutation* vol.29, pp.992-1006 (2008) |
| Other diseases or conditions | Cirrhosis/chronic hepatitis | *Gastroenterologia Japonica* vol.24, pp.270-276 (1989) |
| | Memory impairment | *Nature Communications* vol.7, 12926 (2016) |

In a certain embodiment, the pharmaceutical composition of the present disclosure is used for preventing or treating a cancer. Conventionally, EGFR (epidermal growth factor receptor) inhibitors such as erlotinib and cetuximab are used as anticancer agents. However, it is known that when the Ras protein is a mutant, the response rate is low. Since the pharmaceutical composition of the present disclosure can lead the Ras protein to degradation even when the Ras protein is a mutant, the pharmaceutical composition can be used for treating a cancer that exhibits resistance to the EGFR inhibitor.

The pharmaceutical composition may include a component other than the Ras protein-degradation inducing molecule. For example, the pharmaceutical composition may include an organic or inorganic carrier which is conventionally used as a formulation material. The above carrier is formulated as an excipient, a lubricant, a binder, a disintegrating agent, and the like, in a solid preparation, and as a solvent, a solubilizing agent, a suspending agent, an isotonizing agent, a buffer agent, and the like, in a liquid preparation. Further, the pharmaceutical composition may include a formulation additive such as an antiseptic agent, an antioxidative agent, a coloring agent, a sweetening agent, and the like.

There is no particular limitation for the dosage form of the pharmaceutical composition. Examples of the dosage form of the pharmaceutical composition include oral preparations such as tablet, capsule, granule, powder, trochiscus, syrup, emulsion, suspension, and film preparations; parenteral preparations such injectable preparations, infusion preparations, external preparations, suppositories, pellets, transnasal preparations, pulmonary preparations (inhalation), and eye drops; and the like.

The dose of the pharmaceutical composition is appropriately determined depending on the subject, route of administration, target disease, symptoms, and the like.

EXAMPLES

Below, the present invention will be described specifically with reference to Examples, but the present invention shall not be limited to these Examples. In the following Examples and Reference Examples, room temperature indicates temperatures in a range of 20° C. to 30° C.

Abbreviations of compounds used in the following Examples and Reference Examples are as follows.
H-Gly-OtBu.HCl: L-Glycine t-butyl ester hydrochloride
DMF: N,N-Dimethylformamide
DIPEA: N,N-Diisopropylethylamine
PyBOP: 1H-Benzotriazol-1-yloxy-tri(pyrrolidino)phosphonium hexafluorophosphate
TFA: Trifluoroacetic acid
H-Leu-OtBu.HCl: L-Leucine t-butyl ester hydrochloride
HATU: O-(7-Azabenzotriazol-1-yl)-N,N,N',N'-tetramethyluronium hexafluorophosphate
ec: *Escherichia coli*
DHFR: Dihydrofolate reductase
RF: Restriction-free
HA: Hemagglutinin
GFP: Green fluorescent protein
DsRed: Discosoma sp. red fluorescent protein
D-MEM: Dulbecco's modified eagle's medium
DMSO: Dimethyl sulfoxide
PBS: Phosphate buffered saline
EDTA: Ethylenediamine tetraacetic acid
FBS: Fetal bovine serum
SDS: Sodium dodecyl sulfate
PAGE: Polyacrylamide gel ectrophoresis
BPB: Bromophenol blue
PVDF: Polyvinylidene difluoride
TBS: Tris buffered saline
GAPDH: Glyceraldehyde 3-phosphate dehydrogenase FITC: Fluorescein isothiocyanate
PMSF: Phenylmethylsulfonyl fluoride
DTT: Dithiothreitol
TMP: Trimethoprim
DMT-MM: 4-(4,6-Dimethoxy-1,3,5-triazin-2-yl)-4-methyl-morpholinium chloride n-hydrate
AMC: 7-Amino-4-methylcoumarin Example 1

In Example 1, a Ras protein affinity molecule and a protein-degradation inducing tag were linked to each other to synthesize TUS-007 as a Ras protein-degradation inducing molecule.

Ras-SOS-$NH_2$ represented by the following formula was used as the Ras protein affinity molecule. Ras-SOS-$NH_2$ is a compound obtained by reacting an amino group of Ras-SOS represented by the following formula with $H_2N-(CH_2)_6-COOH$.

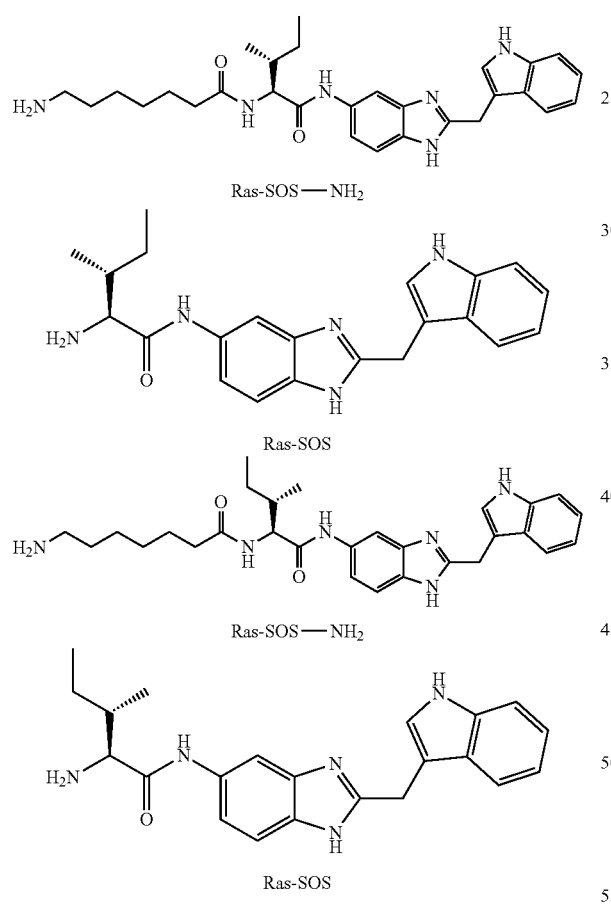

Ras-SOS is Compound 12 described in the document by Sun, Q. et al. (Sun, Q. et al., Angew. Chem. Int. Ed., 2012, 51, 6140-6143) (see No. 22 in Table 4). When a SOS protein is bound to the Ras protein, GDP bound to the Ras protein is replaced with GTP, and the Ras protein is activated. It is known that Ras-SOS is bound to the Ras protein to inhibit the interaction between the Ras protein and the SOS protein, thus inhibiting the activation of the Ras protein. Furthermore, it is known that Ras-SOS is bound to not only a wild-type K-Ras protein but also a G12D mutant and a G12V mutant K-Ras protein.

It is noted that Ras-SOS and Ras-SOS-$MH_2$ were synthesized according to the method described in the document by Sun, Q. et. al.

Furthermore, as the protein-degradation inducing tag, a compound (CANDDY_MLN) in which active sites of MLN9708 and MLN2238 as the proteasome inhibitors (a boronic acid ester moiety or a boronyl group) were replaced with a carboxy group was used.

The method of synthesizing TUS-007 is described in detail as follows.

(Synthesis of CANDDYMLN)

CANDDY MLN was synthesized according to the following synthesis scheme.

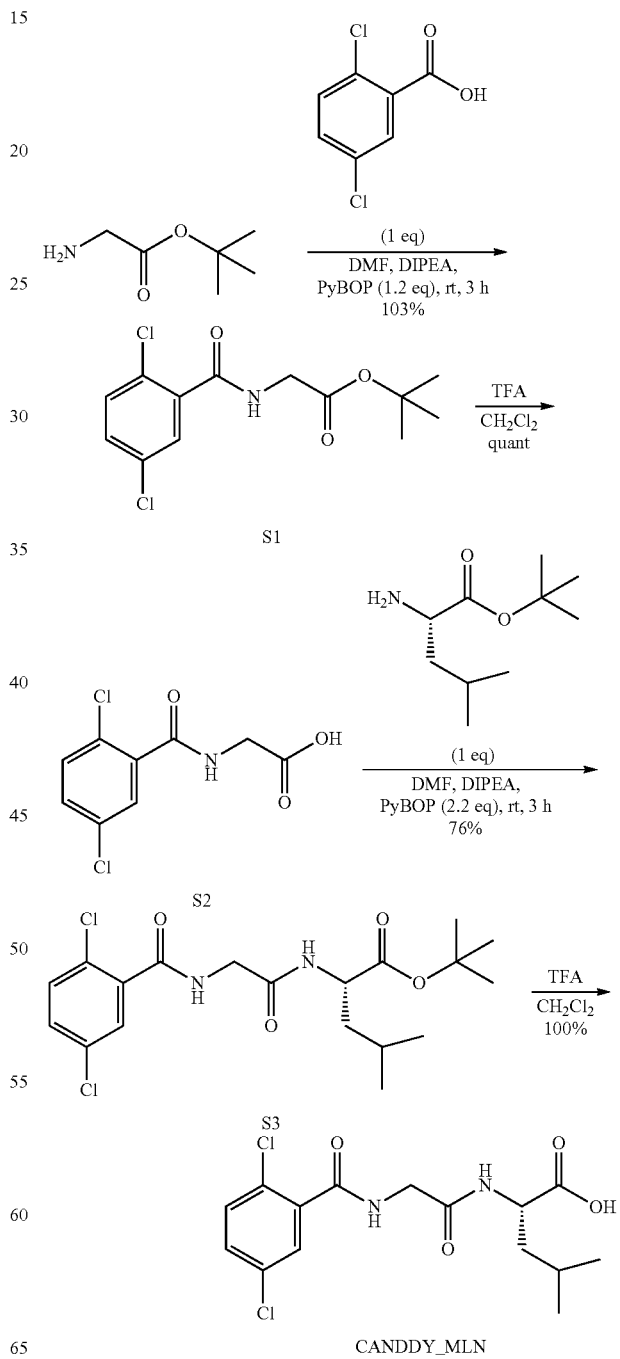

First, H-Gly-OtBuHCl (286.8 mg, 1.69 mmol, 1 eq) was charged into a side-arm eggplant flask, and purged with nitrogen. Under nitrogen gas stream, 10 mL of dehydrate DMF and 5 mL of DIPEA were added, and stirred at room temperature. In 1 mL of dehydrate DMF and 1 mL of DIPEA, 2,5-dichlorobenzoic acid (309.3 mg, 1.62 mmol, 1 eq) was dissolved, which was then added to the reaction solution, and the resultant solution was stirred at room temperature for 20 minutes. PyBOP (1.02 g, 1.96 mmol, 1.2 eq) was dissolved in 1 mL of dehydrate DMF, then added to the reaction solution, and stirred at room temperature for 3 hours. The reaction solution was diluted with water and aqueous sodium hydrogen carbonate, and extracted twice with ethyl acetate/hexane (=4/1). After being dried over anhydrous sodium sulfate, the solvent was evaporated under reduced pressure. Separation and purification treatment was performed by silica gel chromatography (hexane/chloroform=1/1 to 0/1, gradient) to obtain a compound S1 (531.0 mg, 1.75 mmol, 103%).

Next, the compound S1 (212.4 mg, 0.70 mmol) was charged into an eggplant flask, and 5 mL of dichloromethane was then added. This was stirred at room temperature for 5 minutes, then 5 mL of TFA was added thereto, and the resultant solution was stirred at room temperature for one hour. After evaporating the solvent under reduced pressure, vacuum drying was performed to obtain a compound S2 (190.7 mg, quant.).

Next, the compound S2 (190.7 mg, 0.77 mmol, 1 eq) and H-Leu-OtBu.HCl (175.8 mg, 0.79 mmol, 1 eq) were charged into a side-arm eggplant flask, and purged with nitrogen. Under nitrogen gas stream, 5 mL of dehydrate DMF and 5 mL of DIPEA were added, and stirred at room temperature for 20 minutes. PyBOP (886.7 mg, 1.70 mmol, 2.2 eq) was dissolved in 1.5 mL of dehydrate DMF, then the resultant solution was added to the reaction solution and stirred at room temperature for 3 hours. The reaction solution was diluted with water and aqueous sodium hydrogen carbonate, and extracted twice with ethyl acetate/hexane (=4/1). After being dried over anhydrous sodium sulfate, the solvent was evaporated under reduced pressure. Separation and purification treatment was performed by silica gel chromatography (hexane/chloroform=1/1 to 0/1, gradient) to obtain a compound S3 (244.2 mg, 0.58 mmol, 76%).

Next, the compound S3 (240.8 mg, 0.58 mmol) was charged into an eggplant flask, and 5 mL of dichloromethane was added. This was stirred at room temperature for 5 minutes, and then 5 mL of TFA was added, and stirred at room temperature for 1 hour. After evaporating the solvent under reduced pressure, vacuum drying was performed to obtain CANDDY_MLN (214.7 mg, 0.59 mmol, 100%).

(Synthesis of TUS-007)

TUS-007 was synthesized according to the following synthesis scheme.

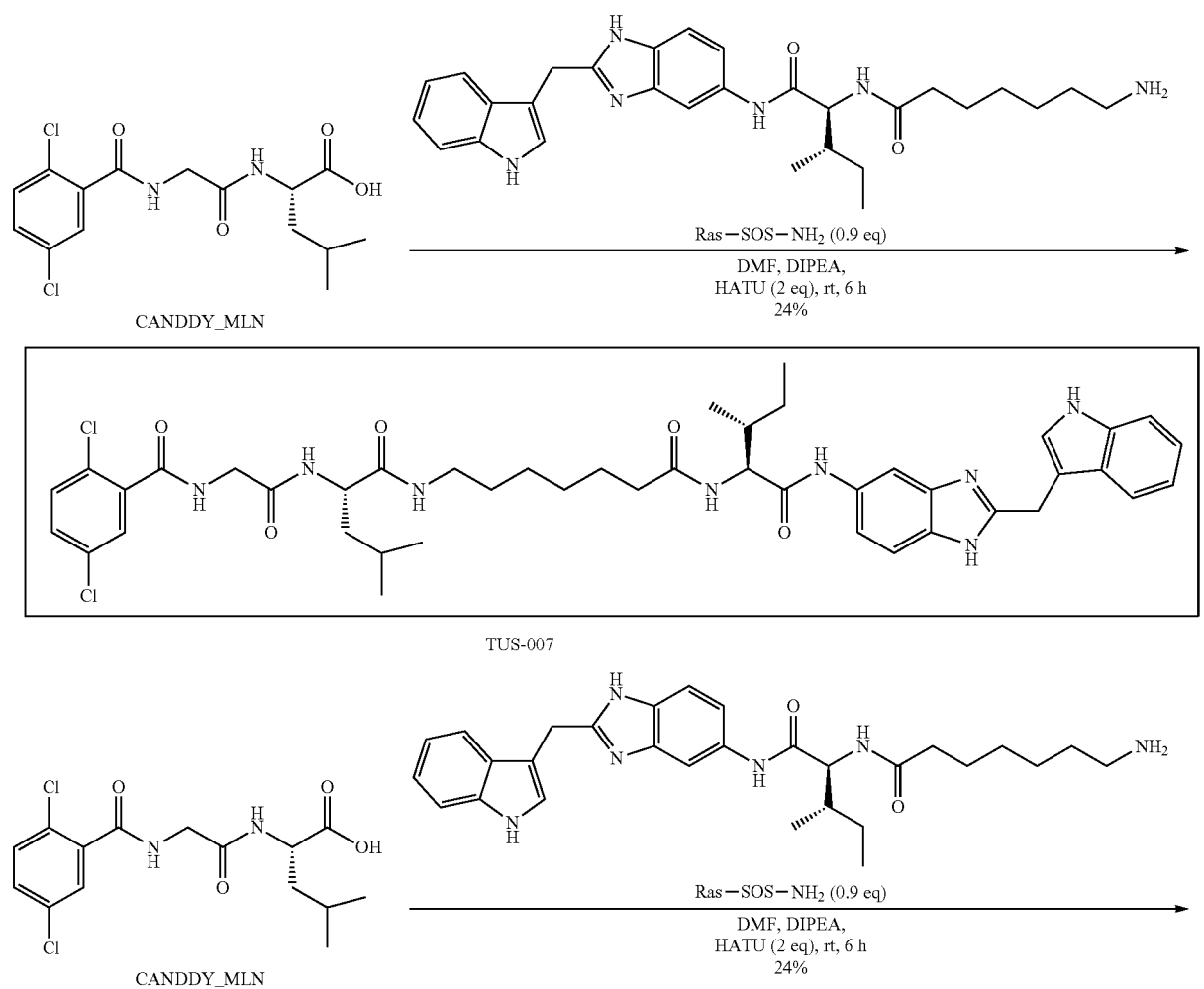

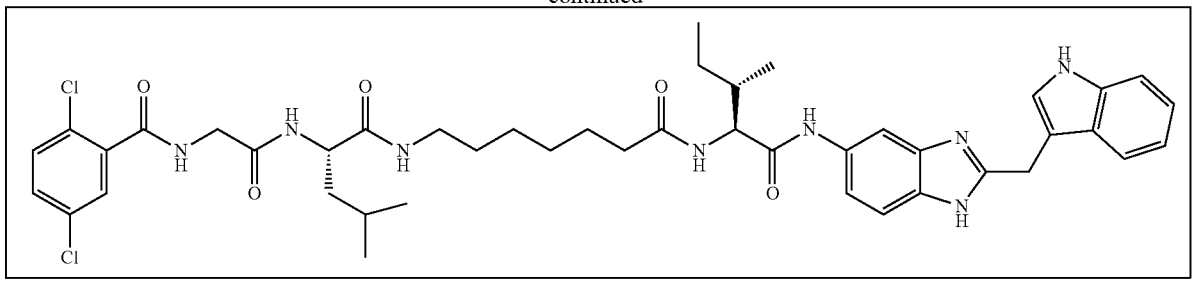

TUS-007

CANDDY_MLN (52.4 mg, 0.15 mmol, 1 eq) and separately synthesized Ras-SOS-NH$_2$ (62.4 mg, 0.12 mmol, 0.9 eq) were charged into an eggplant flask, and 4 mL of dehydrate DMF was then added. After the resultant solution was stirred at room temperature for 5 minutes, 4 mL of DIPEA was then added to neutralize the solution. After the resultant solution was stirred at room temperature for 5 minutes, HATU (114.1 mg, 0.30 mmol, 2 eq) was directly added to a reaction solution, and the reaction solution was stirred at room temperature for 6 hours. Under cooling, a saturated sodium hydrogen carbonate aqueous solution was added, an organic layer was separated, and then a water layer was extracted with ethyl acetate. Organic layers were collected, and dried over anhydrous sodium sulfate. After the solvent was evaporated under reduced pressure, a separation refining process using silica gel chromatography (chloroform/methanol=20/1 to 4/1, gradient) was performed to obtain TUS-007 (25.2 mg, 0.03 mmol, 24%, isolated yield). The obtained TUS-007 was further purified by preparative thin layer chromatography (chloroform/methanol=10/1). The physical property data of TUS-007 are shown as follows. HRMS-FAB (m/z): [M+H]$^+$ calcd for $C_{44}H_{55}Cl_2N_8O_5$, 845.3672; found, 845.3674.

Example 2

In Example 2, degradation (knockdown) of a wild-type K-Ras protein forcibly expressed in HeLa cells (human cervical cancer cells) through TUS-007 was evaluated by FACS analysis.

(Preparation of Plasmid)

A plasmid expressing a wild-type K-Ras protein (K-Ras-WT) was prepared using a plasmid (pMIR-DsRed-IRES-ecDHFR-HA-GFP) expressing an ecDHFR protein by RF cloning. The full-length cDNA clone (Accession No. AK292510) of a human K-ras gene was purchased from Independent Administrative Institution, the National Institute of Technology and Evaluation. PCR amplification was performed using KOD-Plus-Neo (TOYOBO CO., LTD) as a PCR enzyme. Forward primers and reverse primers used for RF cloning are shown in Table 92.

TABLE 92

| Primer name | Sequence (5'→3') | SEQ ID No. |
|---|---|---|
| RFC_IRES-HsKras-HA_Fw | CACGATGATAATATGGCCACAACCATGACTGAATATAAACTTGTGGTAG | 1 |

TABLE 92-continued

| Primer name | Sequence (5'→3') | SEQ ID No. |
|---|---|---|
| RFC_IRES-HsKras-HA_Rv | GAACGTCGTACGGGTAATCGATCATAATTACACACTTTGTCTTTGAC | 2 |

(Introduction of Plasmid into HeLa Cells and Cell Seeding)

The plasmid was introduced into HeLa cells to transiently overexpress a wild-type K-Ras protein (specifically, a fusion protein of a wild-type K-Ras protein and GFP via a HA tag) or a DsRed protein for comparison in the cells.

ScreenFect™ A (Wako Pure Chemical Industries, Ltd.) as a transfection reagent was used to introduce the plasmid into HeLa cells by a routine procedure. The HeLa cells into which the plasmid had been introduced were seeded in a 24-well plate at a cell density of 4×10$^4$ cells/well, and then cultured under conditions of 37° C. and 5 vol % CO$_2$ for 40 hours.

(Addition of TUS-007 to HeLa Cells)

Culture was performed for 40 hours after introduction of the plasmid, and then TUS-007 was added to HeLa cells as follows. As a medium, a serum-free medium (37° C.) in which 1 mass % L-glutamine solution (Sigma-Aldrich) was added to D-MEM (high D-glucose, phenol red, sodium pyruvate (Wako Pure Chemical Industries, Ltd.)) was used. It is noted that the L-glutamine solution was added immediately before use. A DMSO solution containing TUS-007 was mixed with the medium so that the concentration of DMSO was 1 vol %, and added to each well at 500 μL/well, and cultured under conditions of 37° C. and 5 vol % CO$_2$. Furthermore, in addition to an experiment group in which a DMSO solution containing TUS-007 had been added, an experiment group in which a DMSO solution containing both TUS-007 and MLN2238, or Ras-SOS-NH$_2$ had been added was prepared. It is noted that DMSO was used as a control.

(Evaluation of Degradation (Knockdown) of Wild-Type K-Ras Protein Through TUS-007 (FACS Analysis))

The medium was removed 24 hours after addition of TUS-007, and then PBS was added to wash the cells. After removing PBS, trypsin (0.25 w/v % Trypsin-1 mmol/L EDTA•4 Na solution with phenol red) (Wako Pure Chemical Industries, Ltd.) at 37° C. was added to each well at 200 μL/well, and cultured under conditions of 37° C. and 5 vol % CO$_2$ for 1 minute. After culturing, a medium where 10 mass % FBS and 1 mass % PenStrep (100 U/mL sodium penicillin G and 100 μg/mL streptomycin sulfate) (Wako Pure Chemical Industries, Ltd.) were added to D-MEM (low D-glucose, L-glutamine, phenol red) (Wako Pure Chemical Industries, Ltd.) was added to each well at 300 µL/well, and suspended, and then a cell solution was collected in a 15 mL tube.

The cell solution collected was centrifuged (at 1000 rpm×5 minutes, 4° C.), and the supernatant was removed, and then suspended in 2 ml of PBS (37° C.). The cell solution after suspension was centrifuged (at 1000 rpm×5 minutes, 4° C.), and the supernatant was removed, and then 500 µL of an FACS buffer (1 mass % FBS/PBS) at 4° C. was added, and allowed to stand on ice.

A BD FACSCanto™ II (BD Biosciences) was used for flow cytometry, and the expression levels of GFP and the DsRed protein in the cells were quantified. The cell solution was passed through a mesh with a pore size of 32 µm, and transferred to an FACS tube immediately before FACS analysis. The GFP/DsRed ratio per cell was computed using an analysis software FlowJo™ (TOMY Digital Biology Co., Ltd.), and degradation (knockdown) of the wild-type K-Ras protein by TUS-007 was determined from a shift in a graph.

The results of the FACS analysis are shown in FIG. 1. As shown in FIG. 1, when TUS-007 was added, the graph is shifted toward the left in a concentration-dependent manner, demonstrating that degradation of the wild-type K-Ras protein was induced by TUS-007. On the other hand, when Ras-SOS-NH$_2$ was added, the graph is overlapped to that of the control (DMSO), demonstrating that the wild-type K-Ras protein was not degraded. From this result, it is found that the degradation of the wild-type K-Ras protein is induced by linking CANDDY_MLN as a protein-degradation inducing tag to Ras-SOS-NH$_2$. Furthermore, when both TUS-007 and MLN2238 were added, degradation of the wild-type K-Ras protein was inhibited as compared with the case where TUS-007 was added. This result supports that TUS-007 leads the wild-type K-Ras protein to the degradation by a proteasome.

Example 3

In Example 3, degradation (knockdown) of a forcibly expressed wild-type K-Ras protein in HeLa cells through TUS-007 was evaluated by Western blot analysis.
(Preparation of Plasmid)

A plasmid expressing the wild-type K-Ras protein (K-Ras-WT) was prepared, as in Example 2.
(Introduction of Plasmid into HeLa Cells and Cell Seeding)

As in Example 2, the plasmid was introduced into HeLa cells to transiently overexpress the wild-type K-Ras protein (specifically, a fusion protein of the wild-type K-Ras protein and GFP through a HA tag) or a DsRed protein for comparison in the cells. HeLa cells into which the plasmid had been introduced were seeded in a 24-well plate at a cell density of 4×10$^4$ cells/well, and then cultured under conditions of 37° C. and 5 vol % CO$_2$ for 40 hours.
(Addition of TUS-007 to HeLa Cells)

Culture was performed for 40 hours after introduction of the plasmid, and then TUS-007 was added to HeLa cells as follows. As a medium, a serum-free medium (37° C.) in which 1 mass % L-glutamine solution (Sigma-Aldrich) was added to D-MEM (high D-glucose, phenol red, sodium pyruvate (Wako Pure Chemical Industries, Ltd.)) was used. It is noted that the L-glutamine solution was added immediately before use. A DMSO solution containing TUS-007 was mixed with the medium so that the concentration of DMSO was 1 vol %, and added to each well at 500 µL/well, and cultured under conditions of 37° C. and 5 vol % CO$_2$. Furthermore, in addition to an experiment group in which a DMSO solution containing TUS-007 had been added, an experiment group in which a DMSO solution containing both TUS-007 and MLN2238, MLN2238 or Ras-SOS-NH$_2$ had been added was prepared. It is noted that DMSO was used as a control.
(Evaluation of Degradation (Knockdown) of Wild-Type K-Ras Protein Through TUS-007 (Western Blot Analysis))

The medium was removed 24 hours after addition of TUS-007, and then PBS was added to wash the cells. After removing PBS, a mixed solution of a cell lysis buffer (CelLytic™ M, Sigma) and a protease inhibitor (cOmplete™ Mini, EDTA-free, Roche) was added to each well at 27 µL/well. After being allowed to stand at 4° C. for 15 minutes, cells were detached with a pipette tip on ice. A cell solution was collected in a 1.5 mL tube, and flash frozen in liquid nitrogen, and then thawed on ice. After repeating this freeze-thaw cycle for three times, the solution was centrifuged (at 13800 rpm×20 minutes, 4° C.), and the supernatant (cell extract) was collected.

The cell extract collected was subjected to Western blot analysis. An SDS-PAGE gel was prepared using TGX™ FastCast™ Acrylamide Kit, 12% (Bio-Rad). Electrophoresis samples were prepared in a 6×SDS-PAGE sample buffer (62.5 mM Tris-HCl pH 6.8, 2% SDS, 5% 2-mercaptoethanol, 10% glycerol, 0.25% BPB), and placed on a heat block at 95° C. for 4 minutes. Electrophoresis was performed at 150 V for 50 minutes (electrophoresis buffer; 195 mM glycine, 25 mM Tris).

After electrophoresis, proteins were transferred to a PVDF membrane (Immobion™-P, Millipore) under conditions of 100 V and 120 minutes using a tank-type blotting device and a transfer buffer (25 mM Tris-HCl, 195 mM glycine, 0.01% SDS, 15% methanol). The membrane after transfer was shaken and blocked at room temperature for 30 minutes in 5% skim milk/high-salt TBS-T (100 mM Tris-HCl, 500 mM NaCl, 0.2% Tween-20, pH 7.6). After blocking, the membrane was rinsed with high-salt TBS-T, and an antibody reaction was performed in 1% skim milk/high-salt TBS-T. As the antibody, anti-HA-peroxidase, high-affinity (3F10) Rat monoclonal antibody (25 U/mL) (Roche) diluted 1000 times was used. The membrane was shaken at room temperature for one hour, and then washed with high-salt TBS-T for 5 minutes. It is noted that washing was performed three times. Further, the membrane was washed with high-salt TBS (100 mM Tris-HCl, 500 mM NaCl, pH 7.6) for 5 minutes. Subsequently, the membrane was treated with a chemiluminescence reagent Immobilon™ Western (Millipore), and then chemiluminescence was detected using a lumino image analyzer LAS-3000 (FUJIFILM Corporation).

Next, a reaction for detecting GAPDH as a control was performed using the same membrane. The membrane was washed with TBS-T (100 mM Tris-HCl, 150 mM NaCl, 0.1% Tween-20, pH 7.6), and shaken and blocked in 5% skim milk/TBS-T at room temperature for 30 minutes. After blocking, a primary antibody reaction was performed in 5% skim milk/TBS-T. As the primary antibody, anti-GAPDH antibody (6C5, SantaCruz, diluted 20000 times) was used. The membrane was shaken at room temperature for 60 minutes, and then washed with TBS-T for 5 minutes. It is noted that washing was performed three times. After the primary antibody reaction, a secondary antibody reaction was performed in 2% skim milk/TBS-T. As the secondary antibody, an anti-mouse IgG (H+L) antibody (A90-116P-33, Bethyl) diluted 20000 times was used. The membrane was shaken at room temperature for 30 minutes, and then washed with TBS-T for 5 minutes. It is noted that washing was performed three times. Further, the membrane was washed with TBS (100 mM Tris-HCl, 150 mM NaCl, pH 7.6) for 5 minutes. Subsequently, the membrane was treated with a chemiluminescence reagent Immobilon™ Western (Millipore), and then chemiluminescence was detected using a lumino image analyzer LAS-3000 (FUJIFILM Corporation). Detected bands were quantified with an image processing software ImageJ (NIH).

Figure 2:
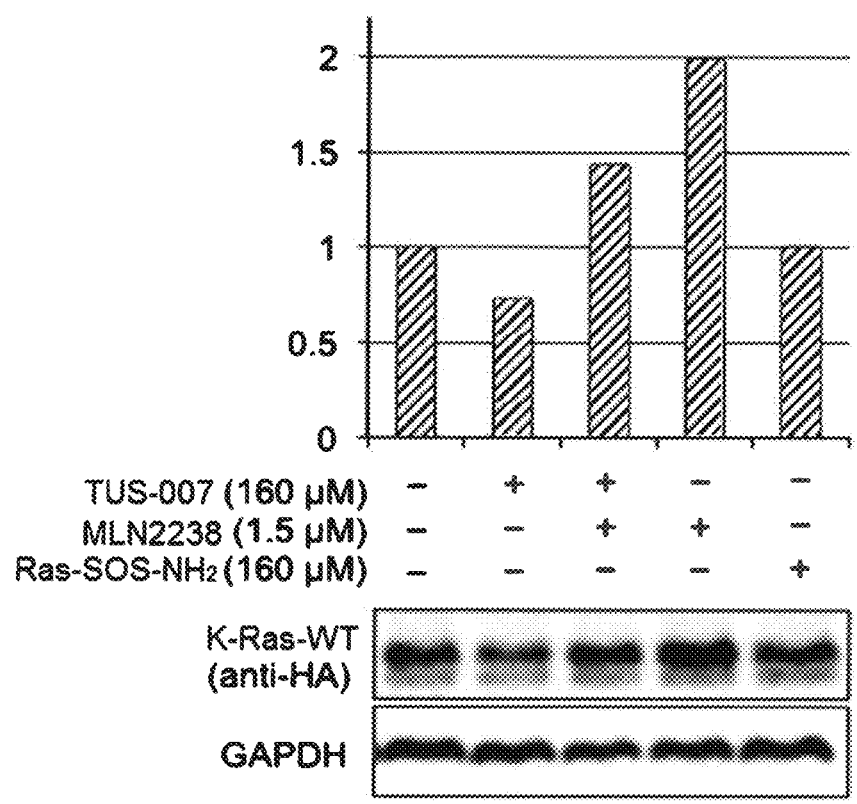
FIG. 2 shows the results of evaluation by Western blot analysis of degradation (knockdown) of a wild-type K-Ras protein forcibly expressed in HeLa cells through TUS-007.

The results of the Western blot analysis are shown in FIG. 2. The graph in FIG. 2 shows the quantification result of the wild-type K-Ras protein detected by the Western blot analysis as a relative value when the value of the control (DMSO) was defined as 1. As shown in FIG. 2, when TUS-007 was added, the amount of the wild-type K-Ras protein was reduced, but when Ras-SOS-NH$_2$ was added, the amount of the wild-type K-Ras protein was not reduced. From this result, it is found that the wild-type K-Ras protein degradation was induced by linking CANDDY_MLN as a protein-degradation inducing tag to Ras-SOS-NH$_2$. Furthermore, when both TUS-007 and MLN2238 were added, the amount of the wild-type K-Ras protein was increased as compared with the amount of the control (DMSO). This result supports that TUS-007 leads the wild-type K-Ras protein to the degradation by a proteasome.

Example 4

In Example 4, degradation (knockdown) of a G12D mutant and a G12V mutant K-Ras protein forcibly expressed in HeLa cells through TUS-007 was evaluated by FACS analysis.
(Preparation of Plasmid)
A plasmid expressing a G12D mutant K-Ras protein (K-Ras-G12D) or a G12V mutant K-Ras protein (K-Ras-G12V) were prepared in the same manner as in Example 2 except that mutation was introduced using a primer. Forward primers and reverse primers used for introducing mutation are shown in Table 93.

TABLE 93

| Primer name | Sequence (5'→3') | SEQ ID No. |
|---|---|---|
| AK292510_G12D_Fw_2 | GGAGCTGATGGCGTAGGCAAGAGTGC | 3 |
| AK292510_G12D_Rv_2 | TACGCCATCAGCTCCAACTACCACAAG | 4 |
| AK292510_G12V_Fw_2 | GGAGCTGTTGGCGTAGGCAAGAGTGC | 5 |
| AK292510_G12V_Rv_2 | TACGCCAACAGCTCCAACTACCACAAG | 6 |

(Introduction of Plasmid into HeLa Cells and Cell Seeding)
The plasmid was introduced into HeLa cells as in Example 2 to transiently overexpress a G12D mutant K-Ras protein or a G12V mutant K-Ras protein in a cell or a DsRed protein for comparison in the cells. HeLa cells into which the plasmid had been introduced were seeded in a 24-well plate at a cell density of 4×10$^4$ cells/well, and then cultured under conditions of 37° C. and 5 vol % CO$_2$ for 40 hours.
(Addition of TUS-007 to HeLa Cells)
TUS-007 was added to HeLa cells as in Example 2. Furthermore, in addition to an experiment group in which a DMSO solution containing TUS-007 had been added, an experiment group in which a DMSO solution containing both TUS-007 and MLN2238, or Ras-SOS-NH$_2$ had been added was prepared. DMSO was used as a control.

(Evaluation of Degradation (Knockdown) of G12D Mutant and G12V Mutant K-Ras Protein Through TUS-007 (FACS Analysis))

Degradation of a G12D mutant and a G12V mutant K-Ras protein through TUS-007 was evaluated by FACS analysis as in Example 2.

Figure 3:
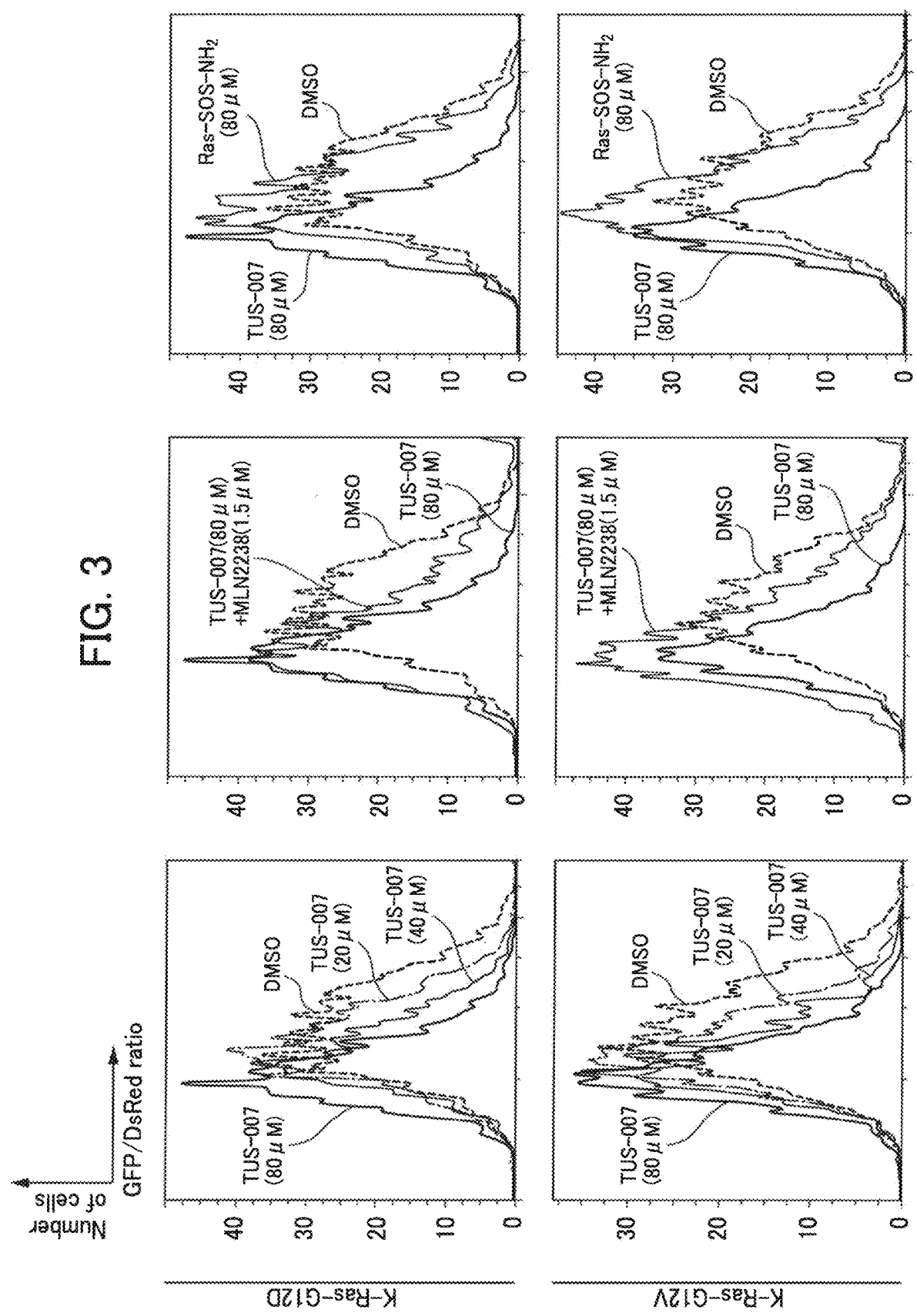
FIG. 3 shows the results of evaluation by FACS analysis of degradation (knockdown) of G12D mutant and G12V mutant K-Ras proteins forcibly expressed in HeLa cells through TUS-007.

The results of the FACS analysis are shown in FIG. 3. As shown in FIG. 3, when TUS-007 was added, the graph is shifted toward the left in a concentration-dependent manner, demonstrating that degradation of the G12D mutant and the G12V mutant K-Ras protein was induced by TUS-007. On the other hand, when Ras-SOS-NH$_2$ was added, the graph is overlapped to that of the control (DMSO), demonstrating that the G12D mutant and G12V mutant K-Ras protein were not degraded. This result shows that by linking CANDDY_MLN as a protein-degradation inducing tag to Ras-SOS-NH$_2$, G12D mutant and G12V mutant K-Ras protein degradation was induced. Furthermore, when both TUS-007 and MLN2238 were added, as compared with the case where TUS-007 was added, G12D mutant and G12V mutant K-Ras protein degradation was inhibited. This result supports that TUS-007 leads the G12D mutant and G12V mutant K-Ras proteins to the degradation by a proteasome.

It is noted that from the results of FIGS. 1 and 3, TUS-007 was excellent in inducing the degradation of the G12D mutant K-Ras protein among the wild-type K-Ras protein, the G12D mutant K-Ras protein, and the G12V mutant K-Ras protein.

Example 5

In Example 5, degradation (knockdown) of the G12D mutant K-Ras protein forcibly expressed in HeLa cells through TUS-007 was evaluated by Western blot analysis.
(Preparation of Plasmid)
A plasmid expressing the G12D mutant K-Ras protein (K-Ras-G12D) was prepared, as in Example 4.
(Introduction of Plasmid into HeLa Cells and Cell Seeding)
As in Example 4, the plasmid was introduced into HeLa cells to transiently overexpress a G12D mutant K-Ras protein or a DsRed protein for comparison in the cells. HeLa cells into which the plasmid had been introduced were seeded in a 24-well plate at a cell density of 4×10$^4$ cells/well, and then cultured under conditions of 37° C. and 5 vol % CO$_2$ for 40 hours.
(Addition of TUS-007 to HeLa Cells)
TUS-007 was added to HeLa cells as in Example 4. Furthermore, in addition to an experiment group in which a DMSO solution containing TUS-007 had been added, an experiment group in which a DMSO solution containing Ras-SOS-NH$_2$ had been added was prepared. DMSO was used as a control.
(Evaluation of Degradation (Knockdown) of G12D Mutant K-Ras Protein Through TUS-007 (Western Blot Analysis))
As in Example 3, degradation of a G12D mutant K-Ras protein through TUS-007 was evaluated by Western blot analysis.

Figure 4:
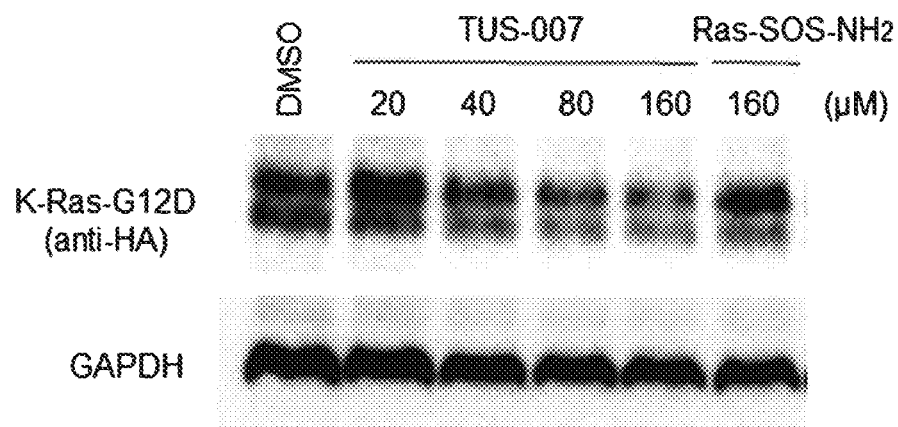
FIG. 4 shows the results of evaluation by Western blot analysis of degradation (knockdown) of G12D mutant K-Ras protein forcibly expressed in HeLa cells through TUS-007.

The results of the Western blot analysis are shown in FIG. 4. As shown in FIG. 4, when TUS-007 was added, the amount of the G12D mutant K-Ras protein was reduced in a concentration-dependent manner, but when Ras-SOS-NH$_2$ was added, the amount of G12D mutant K-Ras protein was not reduced. This result shows that by linking CANDDY_MLN as a protein-degradation inducing tag to Ras-SOS-NH$_2$, the degradation of the G12D mutant K-Ras protein was induced.

Example 6

In Example 6, degradation (knockdown) of an endogenous wild-type K-Ras protein and wild-type H-Ras protein in HeLa cells to which TUS-007 had been added was evaluated by Western blot analysis.
(Cell Seeding)

HeLa cells were seeded in a 24-well plate at a cell density of $8 \times 10^4$ cells/well, and then cultured under conditions of 37° C. and 5 vol % $CO_2$ for 16 hours.
(Addition of TUS-007 to HeLa Cells)

After 16 hours from cell seeding, TUS-007 was added to HeLa cells as follows. As a medium, a serum-free medium (37° C.) in which 1 mass % L-glutamine solution (Sigma-Aldrich) was added to D-MEM (high D-glucose, phenol red, sodium pyruvate (Wako Pure Chemical Industries, Ltd.)) was used. It is noted that the L-glutamine solution was added immediately before use. A DMSO solution containing TUS-007 was mixed with the medium so that the concentration of DMSO was 1 vol %, and added to each well at 500 µL/well, and cultured under conditions of 37° C. and 5 vol % $CO_2$. As a control, DMSO was used.
(Evaluation of Degradation (Knockdown) of Endogenous Wild-Type K-Ras Protein and Wild-Type H-Ras Protein Through TUS-007 (Western Blot Analysis))

The medium was removed 48 hours after addition of TUS-007, and then PBS was added to wash the cells. After removing PBS, a mixed solution of a cell lysis buffer (CelLytic™ M, Sigma) and a protease inhibitor (cOmplete™ Mini, EDTA-free, Roche) was added to each well at 27 µL/well. After being allowed to stand at 4° C. for 15 minutes, cells were detached with a pipette tip on ice. A cell solution was collected in a 1.5 mL tube, and flash frozen in liquid nitrogen, and then thawed on ice. After thawing, the solution was centrifuged (at 13800 rpm×20 minutes, 4° C.), and the supernatant (cell extract) was collected.

The cell extract collected was subjected to Western blot analysis. An SDS-PAGE gel was prepared using TGX™ FastCast™ Acrylamide Kit, 12% (Bio-Rad). Electrophoresis samples were prepared in a 6×SDS-PAGE sample buffer (62.5 mM Tris-HCl pH 6.8, 2% SDS, 5% 2-mercaptoethanol, 10% glycerol, 0.25% BPB), and placed on a heat block at 95° C. for 4 minutes. Electrophoresis was performed at 150 V for 50 minutes (electrophoresis buffer; 195 mM glycine, 25 mM Tris).

After electrophoresis, proteins were transferred to a PVDF membrane (Immobion™-P, Millipore) under conditions of 100 V and 2 hours using a tank-type blotting device and a transfer buffer (25 mM Tris-HCl, 195 mM glycine, 0.01% SDS, 15% methanol). The membrane after transfer was shaken and blocked at room temperature for 30 minutes in 5% skim milk/TBS-T (100 mM Tris-HCl, 150 mM NaCl, 0.1% Tween-20, pH 7.6). After blocking, a primary antibody reaction was performed in 5% skim milk/TBS-T. As the primary antibody, an anti-K-Ras antibody (C-17, SantaCruz, diluted 500 times), an anti-H-Ras antibody (C-20, SantaCruz, diluted 1000 times), and an anti-SOS1 antibody (C-23, SantaCruz, diluted 1000 times) were used. The membrane was shaken at 4° C. for 16 hours, and then washed with TBS-T for 5 minutes. It is noted that washing was performed three times. Further, the membrane was washed with TBS-T for 5 minutes. Subsequently, the membrane was treated with a chemiluminescence reagent Immobilon™ Western (Millipore), and then chemiluminescence was detected using a lumino image analyzer LAS-3000 (FUJIFILM Corporation).

Next, a reaction for detecting GAPDH as a control was performed using the same membrane. The membrane was washed with TBS-T, and shaken and blocked in 5% skim milk/TBS-T at room temperature for 30 minutes. After blocking, primary antibody reaction was performed in 5% skim milk/TBS-T. As the primary antibody, anti-GAPDH antibody (6C5, SantaCruz, diluted 20000 times) was used. The membrane was shaken at room temperature for 60 minutes, and then washed with TBS-T for 5 minutes. It is noted that washing was performed three times. After the primary antibody reaction, secondary antibody reaction was performed in 2% skim milk/TBS-T. As the secondary antibody, anti-mouse IgG (H+L) antibody (A90-116P-33, Bethyl) diluted 20000 times was used. The membrane was shaken at room temperature for 30 minutes, and then washed with TBS-T for 5 minutes. It is noted that washing was performed three times. Further, the membrane was washed with TBS (100 mM Tris-HCl, 150 mM NaCl, pH 7.6) for 5 minutes. Subsequently, the membrane was treated with a chemiluminescence reagent Immobilon™ Western (Millipore), and then chemiluminescence was detected using a lumino image analyzer LAS-3000 (FUJIFILM Corporation). Detected bands were quantified with an image processing software ImageJ (NIH).

Figure 5:
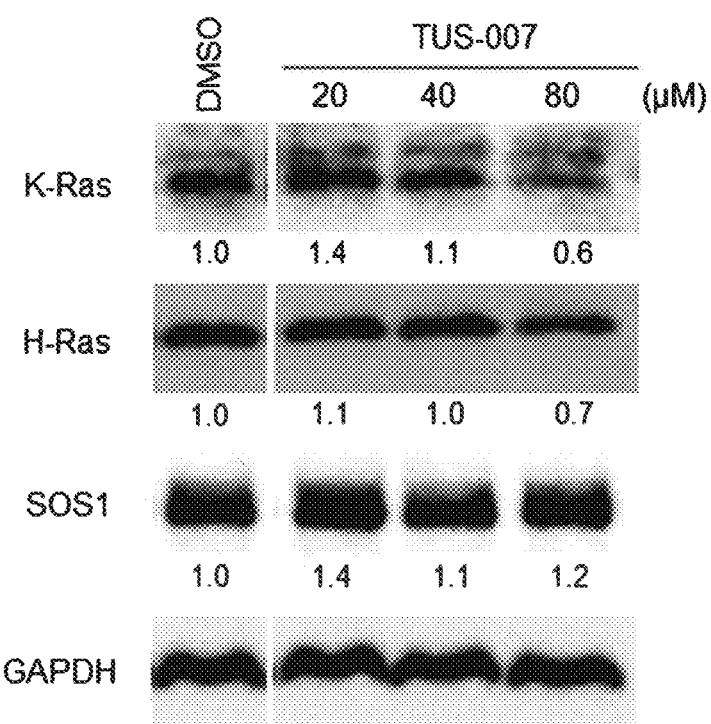
FIG. 5 shows the results of evaluation by Western blot analysis of degradation (knockdown) of an endogenous wild-type K-Ras protein and wild-type H-Ras protein in HeLa cells to which TUS-007 was added.

The results of the Western blot analysis are shown in FIG. 5. Numeric values below each band in FIG. 5 show the quantification result of each protein detected by the Western blot analysis as a relative value when the value of the control (DMSO) was defined as 1.0. As shown in FIG. 5, when TUS-007 was added, the amount of the endogenous wild-type K-Ras protein and wild-type H-Ras protein was reduced, but the amount of the SOS1 protein was not reduced. This result matches the results of the protein affinity of Ras-SOS reported in the document by Sun, Q. et al. (Sun, Q. et al., Angew. Chem. Int. Ed., 2012, 51, 6140-6143).

Example 7

In Example 7, apoptosis induction in a case where TUS-007, Ras-SOS, or Ras-SOS-NH$_2$ was added to HeLa cells or SW1990 cells (human pancreatic cancer cells) had been added was evaluated by the FACS analysis. It is noted that in HeLa cells, the wild-type K-Ras protein (K-Ras-WT) is expressed, and in SW1990 cells, the G12D mutant K-Ras protein (K-Ras-G12D) is expressed.
(Cell Seeding)

HeLa cells or SW1990 cells were seeded in a 24-well plate at a cell density of $8 \times 10^4$ cells/well, and then cultured under conditions of 37° C. and 5 vol % $CO_2$ for 16 hours.
(Addition of TUS-007, Ras-SOS, or Ras-SOS-NH$_2$ to HeLa Cells or SW1990 Cells)

After 16 hours from cell seeding, TUS-007, Ras-SOS, or Ras-SOS-NH$_2$ were added to HeLa cells or SW1990 cells as follows. As a medium, a serum-free medium (37° C.) in which 1 mass % L-glutamine solution (Sigma-Aldrich) was added to D-MEM (high D-glucose, phenol red, sodium pyruvate (Wako Pure Chemical Industries, Ltd.)) was used. It is noted that the L-glutamine solution was added immediately before use. A DMSO solution containing TUS-007, Ras-SOS, or Ras-SOS-NH$_2$ was mixed with the medium so that the concentration of DMSO was 1 vol %, and added to each well at 500 µL/well, and cultured under conditions of 37° C. and 5 vol % $CO_2$. As a control, DMSO was used.

(Apoptosis Induction by TUS-007, Ras-SOS, or Ras-SOS-NH$_2$ (FACS Analysis))

The medium was removed 24 hours after addition of TUS-007, Ras-SOS, or Ras-SOS-NH$_2$, and then PBS was added to wash the cells. After removing PBS, trypsin (0.25 w/v % trypsin-1 mmol/L EDTA•4 Na solution with phenol red) (Wako Pure Chemical Industries, Ltd.) at 37° C. was added to each well at 200 μL/well, and cultured under conditions of 37° C. and 5 vol % CO$_2$ for 1 minute. After culturing, a medium where 10 mass % FBS and 1 mass % PenStrep (100 U/mL sodium penicillin G and 100 μg/mL streptomycin sulfate) (Wako Pure Chemical Industries, Ltd.) had been added to D-MEM (low D-glucose, L-glutamine, phenol red) (Wako Pure Chemical Industries, Ltd.) was added to each well at 800 μL/well, and suspended, and then a cell solution was collected in a 15 mL tube.

The cell solution collected was centrifuged (at 1000 rpm×5 minutes, 4° C.), and the supernatant was removed, and then 85 μL of a binding buffer (Annexin V-FITC Kit, Medical & Biological Laboratories) was added thereto and cells were re-suspended. Furthermore, 10 μL of Annexin V-FITC and 5 μL of propidium iodide (PI) were added and incubated in a dark place at room temperature for 15 minutes, thereby staining the cells. After incubation, 400 μL of the binding buffer was added on ice.

A BD FACSCanto™ II (BD Biosciences) was used for flow cytometry. Immediately before FACS analysis, a cell solution was passed through a mesh having a 32 μm-hole diameter, and transferred to an FACS tube. The proportion of Annexin V-positive and PI-negative cells was calculated using an analysis software FlowJo™ (TOMY Digital Biology Co., Ltd.), and the proportion was defined as a proportion of apoptosis cells.

Figure 6A:
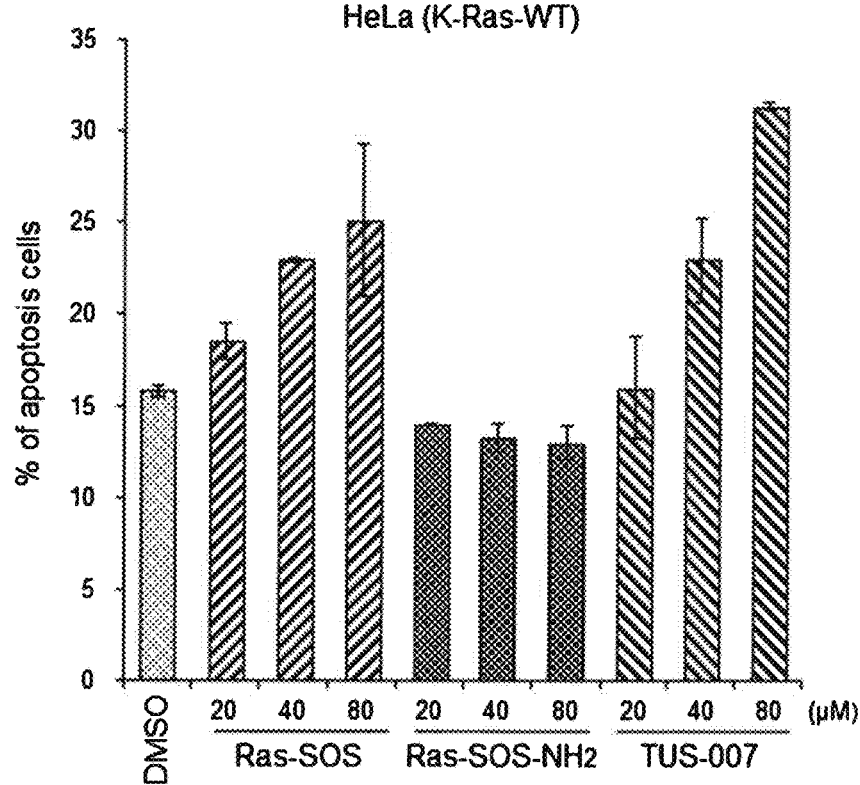
FIG. 6A shows the results of evaluation by FACS analysis of apoptosis induction when TUS-007, Ras-SOS, or Ras-SOS-NH$_2$ was added to HeLa cells.
Figure 6B:
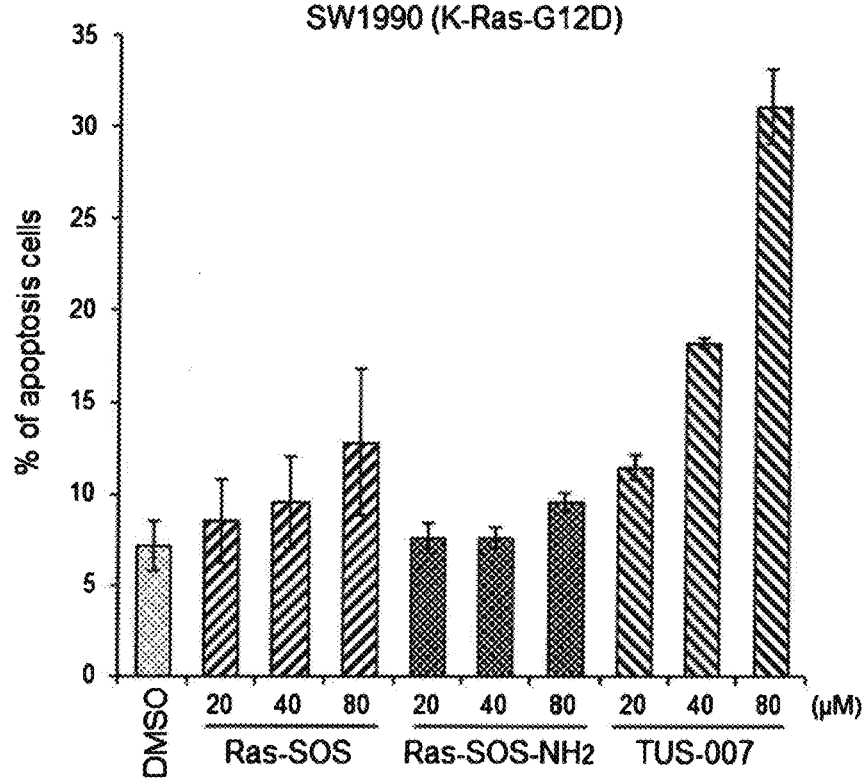
FIG. 6B shows the results of evaluation by FACS analysis of apoptosis induction when TUS-007, Ras-SOS, or Ras-SOS-NH$_2$ was added to SW1990 cells.

The proportion of apoptosis cells in the HeLa cells is shown in FIG. 6A, and the proportion of apoptosis cells in the SW1990 cells is shown in FIG. 6B. FIGS. 6A and 6B show the proportion of apoptosis cells measured by FACS analysis twice, as a mean value±standard error. As shown in FIG. 6A, in the HeLa cells expressing the wild type Ras protein, apoptosis was induced in a concentration-dependent manner by addition of TUS-007 or Ras-SOS, but apoptosis was not induced by addition of Ras-SOS-NH$_2$. On the other hand, as shown in FIG. 6B, in the SW1990 cells expressing the G12D mutant K-Ras protein, the effect of the apoptosis induction by Ras-SOS was largely reduced, but the effect of the apoptosis by TUS-007 was high at the same level as in the case of the HeLa cells.

Example 8

In Example 8, apoptosis induction in a case where TUS-007, Ras-SOS-NH2, or erlotinib as an anticancer agent (EGFR inhibitor) was added to HeLa cells or SW1990 cells was evaluated by FACS analysis as in Example 7.

Figure 7A:
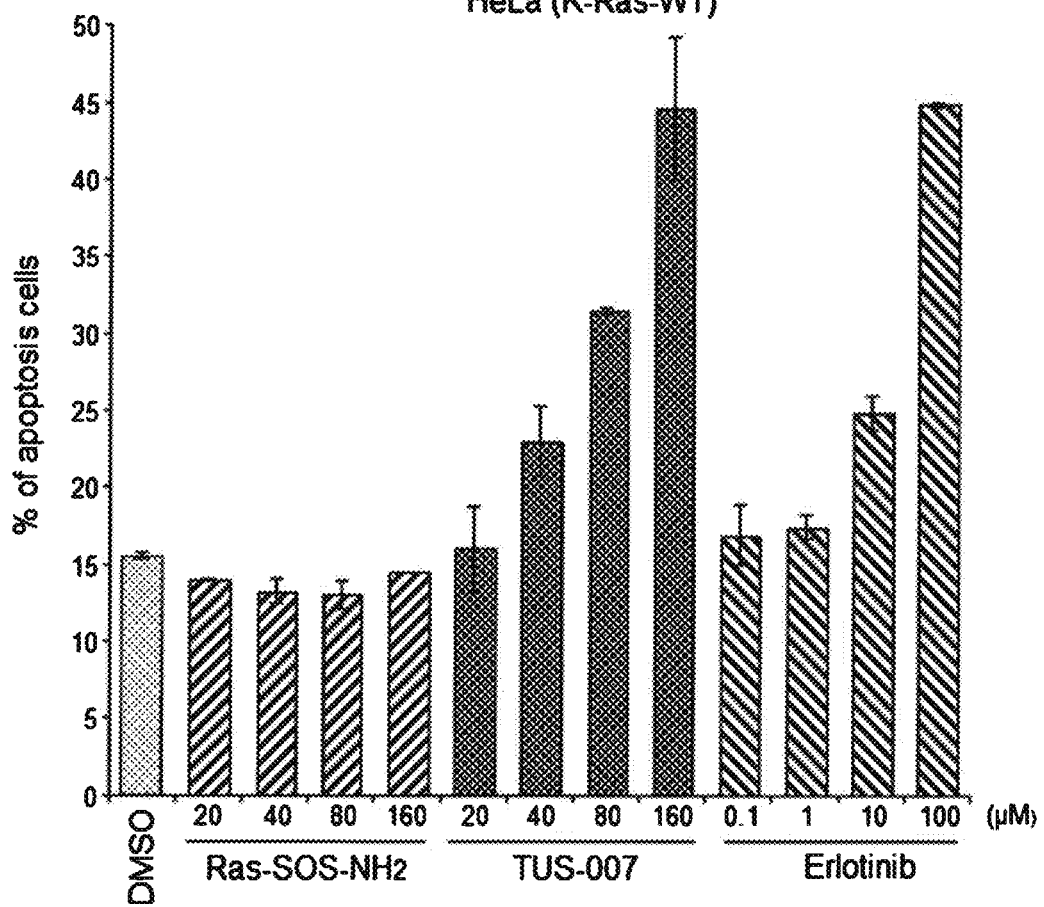
FIG. 7A shows the results of evaluation by FACS analysis of apoptosis induction when TUS-007, Ras-SOS-NH$_2$ or erlotinib was added to HeLa cells.
Figure 7B:
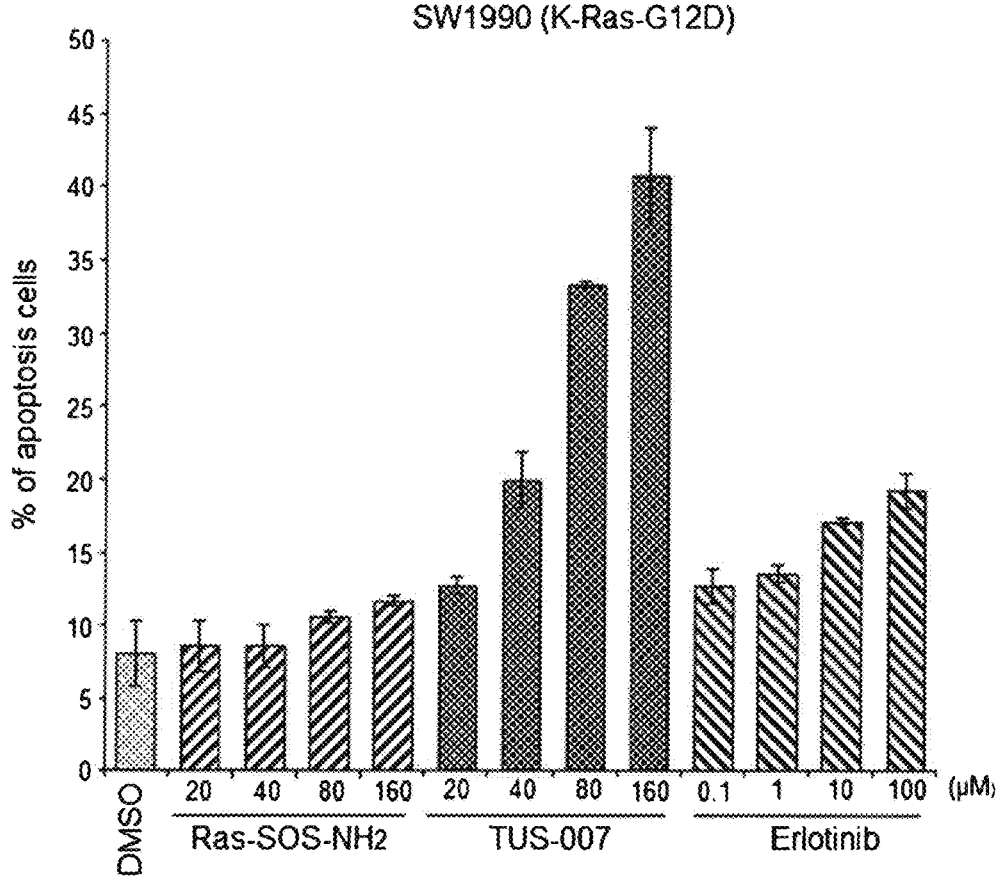
FIG. 7B shows the results of evaluation by FACS analysis of apoptosis induction when TUS-007, Ras-SOS-NH$_2$ or erlotinib was added to SW1990 cells.

The proportion of apoptosis cells in the HeLa cells is shown in FIG. 7A, and the proportion of apoptosis cells in the SW1990 cells is shown in FIG. 7B. FIGS. 7A and 7B show the proportion of apoptosis cells measured by FACS analysis twice, as a mean value±standard error. As shown in FIG. 7A, in the HeLa cells expressing the wild type Ras protein, apoptosis was induced in a concentration-dependent manner by addition of TUS-007 or erlotinib, but apoptosis was not induced by addition of Ras-SOS-NH$_2$. On the other hand, as shown in FIG. 7B, in the SW1990 cells expressing the G12D mutant K-Ras protein, the effect of the apoptosis induction by erlotinib was largely reduced, but the effect of the apoptosis by TUS-007 was high at the same level as in the case of the HeLa cells.

Example 9

In Example 9, in a mouse individual to which TUS-007 had been administered, the degradation (knockdown) of an endogenous wild-type K-Ras protein and wild-type H-Ras protein was evaluated by Western blot analysis.
(Administration of TUS-007 to Mice)

TUS-007 was dissolved in DMSO, and then dissolved in corn oil so that the concentration of DMSO was 10 vol %, and then intraperitoneally administered to C57BL/6J wild-type mice (8 to 9 weeks old, male) (CLEA Japan, Inc.) in an amount of 40 mg/kg body weight or 80 mg/kg body weight (n=3 to 4). Furthermore, in addition to a group in which TUS-007 was administered, a group in which Ras-SOS had been administered in a dose of 80 mg/kg body weight was prepared. As a control, an injection carrier (corn oil containing 10 vol % DMSO) was used. The mice were kept under an environment of ad libitum access to food and water. The mice were dissected under deep anesthesia 48 hours after administration. The pancreas and colon were excised, and flash frozen in liquid nitrogen.
(Western Blot Analysis of Mouse Tissues)

The frozen pancreas and colon were each triturated, and then TKM tissue lysis buffer (50 mM triethanolamine (pH 7.8), 50 mM KCl, 5 mM MgCl$_2$, 0.25 M sucrose, 1 mM PMSF, Protein Inhibitors Cocktail-EDTA free (Nacalai Tesque, Inc.), 1 mM DTT, and a recombinant RNase inhibitor (0.2 U/μL, Takara Bio) were added, and subjected to centrifugation (at 13800 rpm×30 minutes, 4° C.), and the supernatants (pancreatic tissue extract and colorectal tissue extract) were collected. The concentration of the extracted proteins was quantified with a spectrophotometer.

Each tissue extract collected was subjected to Western blot analysis. An SDS-PAGE gel was prepared using TGX™ FastCast™ Acrylamide Kit, 12% (Bio-Rad). Electrophoresis samples were prepared in a 6×SDS-PAGE sample buffer (62.5 mM Tris-HCl pH 6.8, 2% SDS, 5% 2-mercaptoethanol, 10% glycerol, 0.25% BPB), and placed on a heat block at 95° C. for 5 minutes. Electrophoresis was performed at 180 V for 50 minutes (electrophoresis buffer; 195 mM glycine, 25 mM Tris).

After electrophoresis, proteins were transferred to a PVDF membrane (Immobion™-P, Millipore) under conditions of 200 mA and 90 minutes using a tank-type blotting device and a transfer buffer (25 mM Tris-HCl, 195 mM glycine, 0.01% SDS, 15% methanol). The membrane after transfer was shaken and blocked in 5% skim milk/TBS-T (100 mM Tris-HCl, 150 mM NaCl, 0.1% Tween-20, pH 7.6) at room temperature for 30 minutes. After blocking, a primary antibody reaction was performed in 5% skim milk/TBS-T. As the primary antibody, an anti-K-Ras antibody (F-234, SantaCruz, diluted 500 times), an anti-H-Ras antibody (M-90, SantaCruz, diluted 500 times), an anti-SOS1 antibody (C-23, SantaCruz, diluted 1000 times), and an anti-GAPDH antibody (6C5, SantaCruz, diluted 20000 times) were used. The membrane was shaken at room temperature for 2 hours, and then washed with TBS-T for 5 minutes. It is noted that washing was performed three times. Furthermore, the membrane was washed with TBS-T for 5 minutes. Subsequently, the membrane was treated with a chemiluminescence reagent Immobilon™ Western (Millipore), and then chemiluminescence was detected using a lumino image analyzer LAS-3000 (FUJIFILM Corporation).

Figure 8:
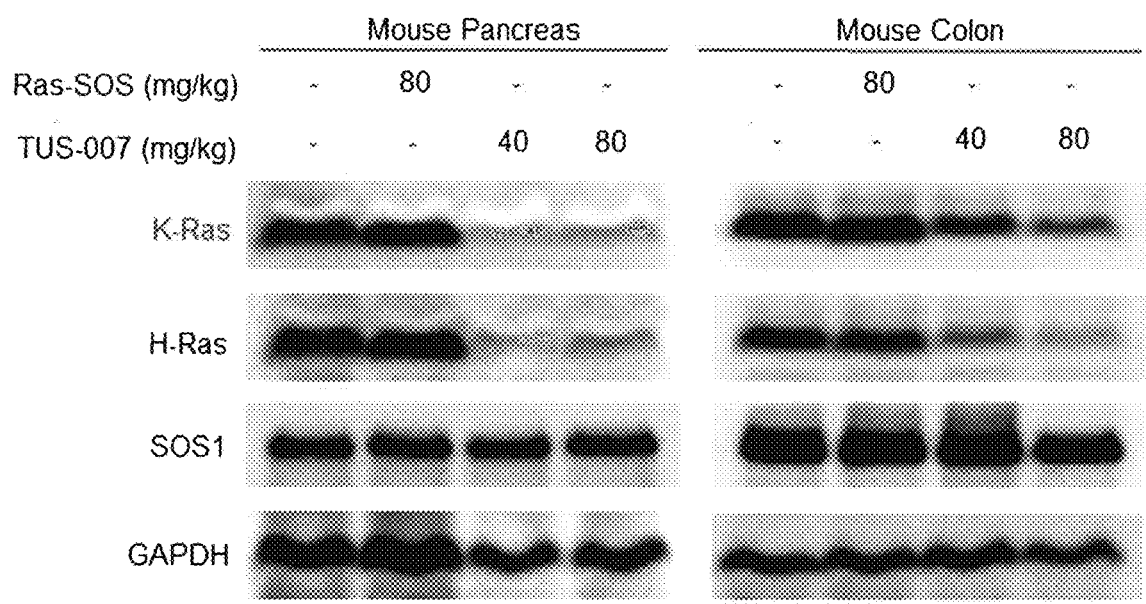
FIG. 8 shows the results of evaluation by Western blot analysis of degradation (knockdown) of an endogenous wild-type K-Ras protein and wild-type H-Ras protein in the pancreas tissue and colorectal tissue when TUS-007 was administered to a mouse individual.

The results of the Western blot analysis are shown in FIG. 8. As shown in FIG. 8, when TUS-007 was administered to mice, the amount of the endogenous wild-type K-Ras protein and wild-type H-Ras protein was reduced in a concentration-dependent manner, and in particular, remarkably reduced in the pancreatic tissue. On the other hand, when Ras-SOS was administered to mice, the amount of the wild-type K-Ras protein and the wild-type H-Ras protein was not reduced.

Example 10

In Example 10, TUS-007 was administered to mice subcutaneously implanted with human pancreatic cancer cells (SW1990 cells), and an anti-tumor effect was evaluated.
(Preparation of Mice with Subcutaneously Implanted SW1990 Cells)

To the subcutis of T-cell deficient mice (BALB/cAJcl-nu/nu, 4 weeks old, female) (CLEA Japan, Inc.), 0.1 mL of cell suspension in which SW1990 cells were suspended in PBS so as to be $1 \times 10^7$ cells/mL was implanted using a 26-gauge injection needle (TERUMO CORPORATION).
(Oral Administration of TUS-007)

Immediately before administration, TUS-007 was dissolved in DMSO, 0.5 mass % carboxymethyl cellulose (Code No. 039-01335, Wako Pure Chemical Industries, Ltd.) solution was added so that the concentration of DMSO became 2.5 vol %, followed by pulverization by ultrasonic treatment to prepare a suspension of TUS-007. When the tumors of mice with subcutaneously implanted SW1990 cells grew to a size of approximately 100 mm³, the prepared TUS-007 suspension was orally administered by gavage with a gastric tube (Code No. 5202K, Fuchigami Kikai) at a dose of 80 mg/kg body weight once every 3 days for a total of 7 doses (n=6 to 9). As a control (Vehicle), 0.5 mass % carboxymethyl cellulose solution containing 2.5 vol % DMSO was administered in the same manner.

(Evaluation of Anti-Tumor Effect)

Figure 9A:
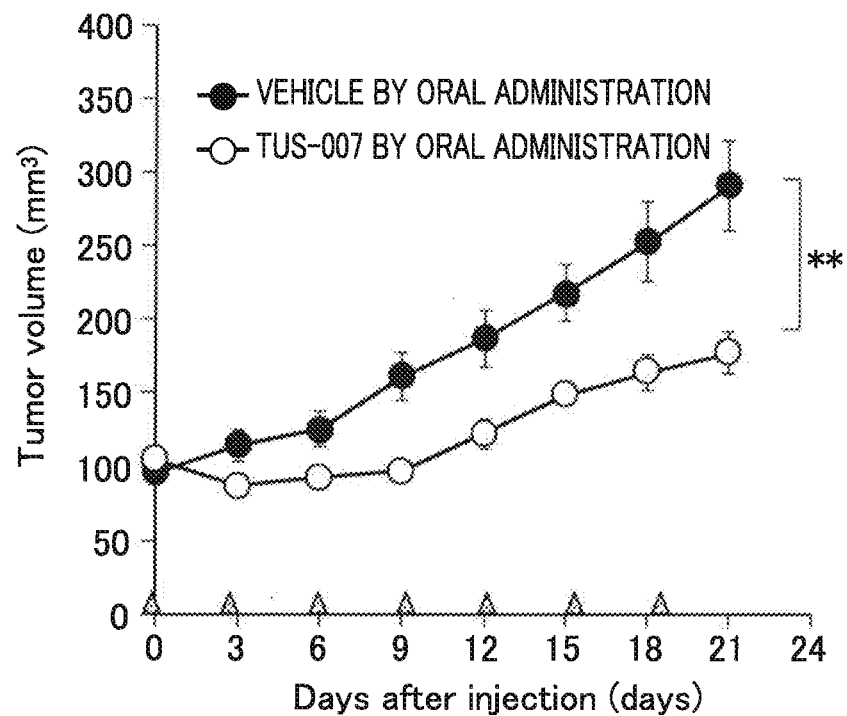
FIG. 9A shows change of a tumor volume over time when TUS-007 was administered to a mouse subcutaneously implanted with human pancreatic cancer cells.

Change over time of a tumor volume by administration of TUS-007 is shown in FIG. 9A. The tumor volume (mm³) was calculated by measuring the tumor size using a caliper, and using the formula (minor axis diameter)²×major axis diameter/2. As shown in FIG. 9A, in the group administered with TUS-007, the increase of the tumor volume was significantly suppressed (p=0.004) as compared with the control group (Vehicle).
(Evaluation of Change of Body Weight)

Figure 9B:
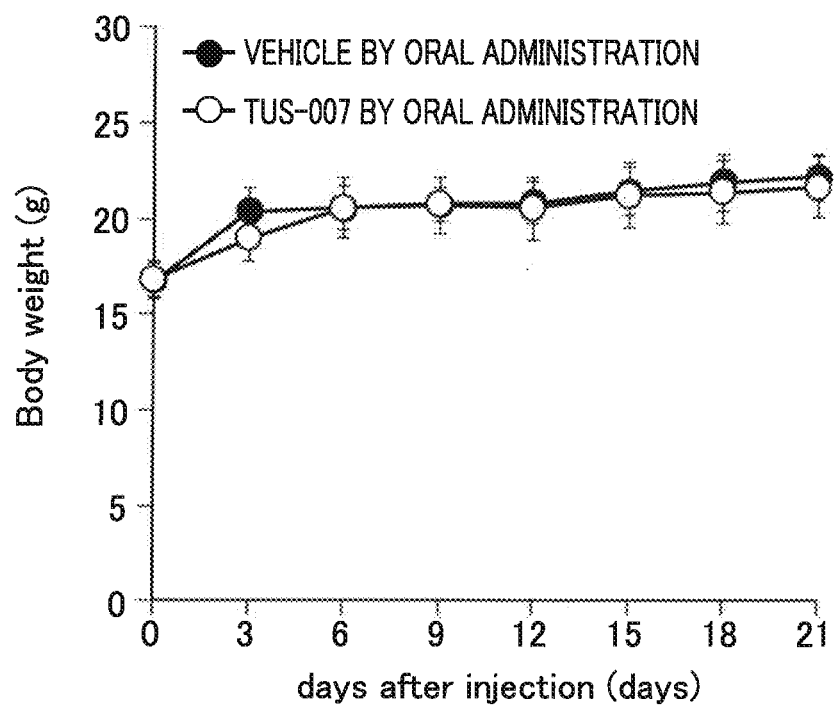
FIG. 9B shows change of a body weight over time when TUS-007 was administered to a mouse subcutaneously implanted with human pancreatic cancer cells.

The change over time of body weight by administration of TUS-007 is shown in FIG. 9B. As shown in FIG. 9B, in repeated administration of TUS-007 once every 3 days for a total of 7 doses, there were no significant differences in body weight changes between the TUS-007 group and the control group (Vehicle). There was no abnormality in the general condition of the mice.
(Evaluation of Acute Toxicity)

Acute toxicity when TUS-007 was orally administered to Jcl:ICR mice (8 weeks old, female) (CLEA Japan, Inc.) in a single dose of 80 mg/kg body weight, 300 mg/kg body weight, or 1000 mg/kg body weight was evaluated. At all doses, there was no abnormality in the general condition of the mice, and $LD_{50}>1000$ mg/kg body weight was satisfied.

REFERENCE EXAMPLE 1

In Reference Example 1, a protein affinity molecule and a protein-degradation inducing tag were linked to each other to synthesize TMP-CANDDY_DMT as a protein-degradation inducing molecule.

As the protein affinity molecule, a TMP derivative (TMP-NH₂) was used. The TMP derivative was obtained by introducing a functional group including an amino group into TMP that is a dihydrofolate reductase inhibitor to be bonded to an ecDHFR protein. Furthermore, as the protein-degradation inducing tag, a compound (DMT) in which $R^1$ and $R^2$ in the aforementioned formula (I) are each a methoxy group was used. DMT is a compound which is not derived from a proteasome inhibitor, but has an affinity with a proteasome.

The method of synthesizing TMP-CANDDY_DMT is described in detail as the following synthesis scheme.

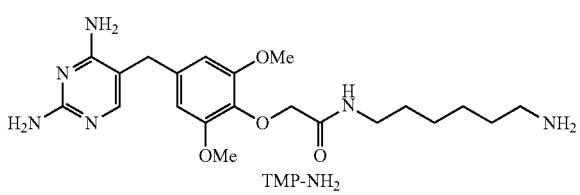

TMP-NH₂

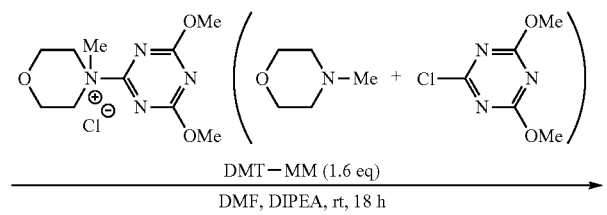

DMT—MM (1.6 eq)
DMF, DIPEA, rt, 18 h

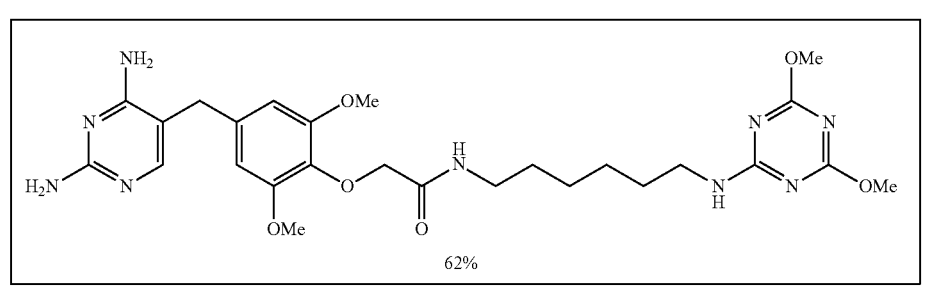

62%

TMP-CANDDY_DMT

TMP-NH$_2$ (Long, M. J. et al., Chem. Biol., 2012, 19 (5), 629-637) (31.7 mg, 0.073 mmol) was charged into an eggplant flask, and 0.3 mL of dehydrate DMF was added. After the resultant solution was stirred at room temperature for 10 minutes, 0.1 mL of DIPEA was added, and stirred at room temperature for 10 minutes. DMT-MM (33.6 mg, 0.12 mmol, 1.6 eq, Wako Pure Chemical Industries, Ltd.) was directly added to the reaction solution, and stirred at room temperature for 18 hours. The reaction solution was diluted with water and aqueous sodium hydrogen carbonate, and extracted with chloroform for five times. After being dried over anhydrous sodium sulfate, the solvent was evaporated under reduced pressure. Separation and purification treatment was performed by silica gel chromatography (chloroform/methanol=92/8) to obtain TMP-CANDDY_DMT (25.8 mg, 0.045 mmol, 62%, isolated yield).

Reference Example 2

In Reference Example 2, the proteasome inhibitory activity of TMP-CANDDY_DMT and the affinity of TMP-CANDDY_DMT with a proteasome were evaluated. As a positive control, MG-132 as a proteasome inhibitor was used.

For evaluation, 20S Proteasome StressXpress™ Assay Kit Gold (Bioscience) was used. AMC was measured by using Multi-Detection Microplate Reader (Synergy HT, BIO-TEK). The AMC was produced by cleaving the C-terminus of an AMC-binding proteasome fluorescence substrate specific to β subunits of a 20S proteasome, including β5 (chymotrypsin-like activity), β2 (trypsin-like activity), and β1 (caspase-like activity). The measuring wavelengths were 360 nm for excitation light (Ex.), and 460 nm for fluorescence (Em.).

Figure 10A:
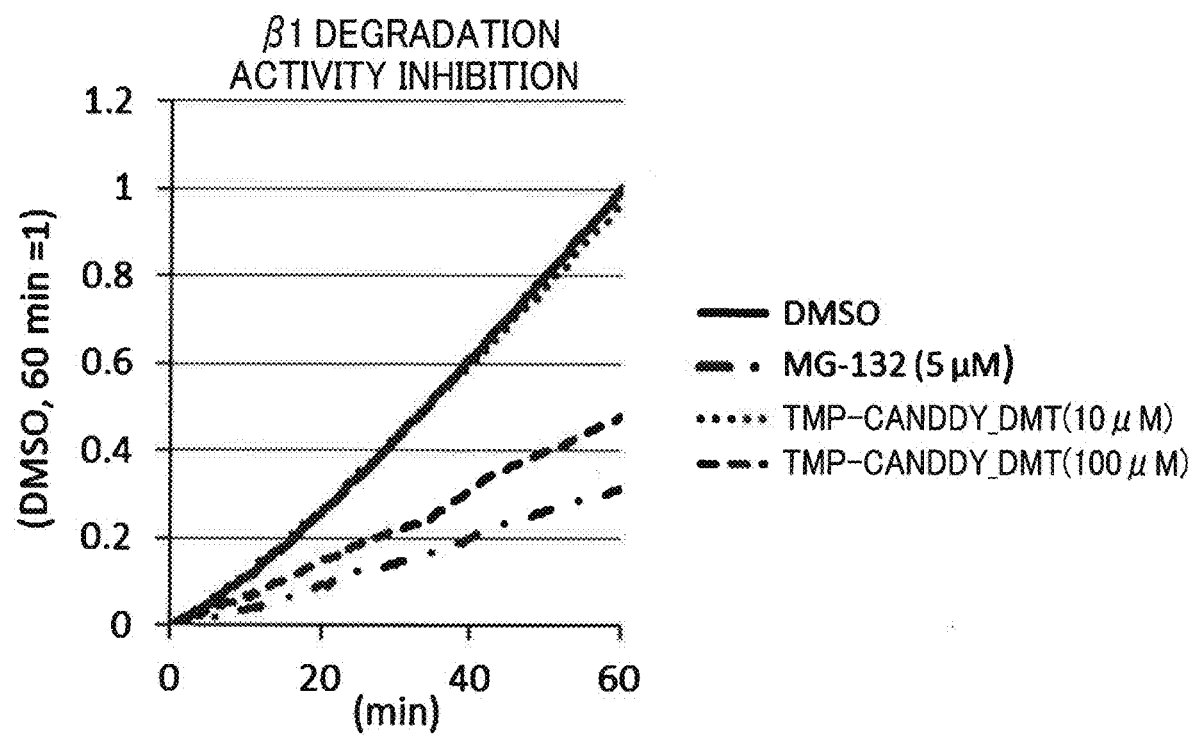
FIG. 10A shows inhibitory activity of TMP-CANDDY_DMT and MG-132 with respect to a catalytic subunit β1 of a proteasome.
Figure 10B:
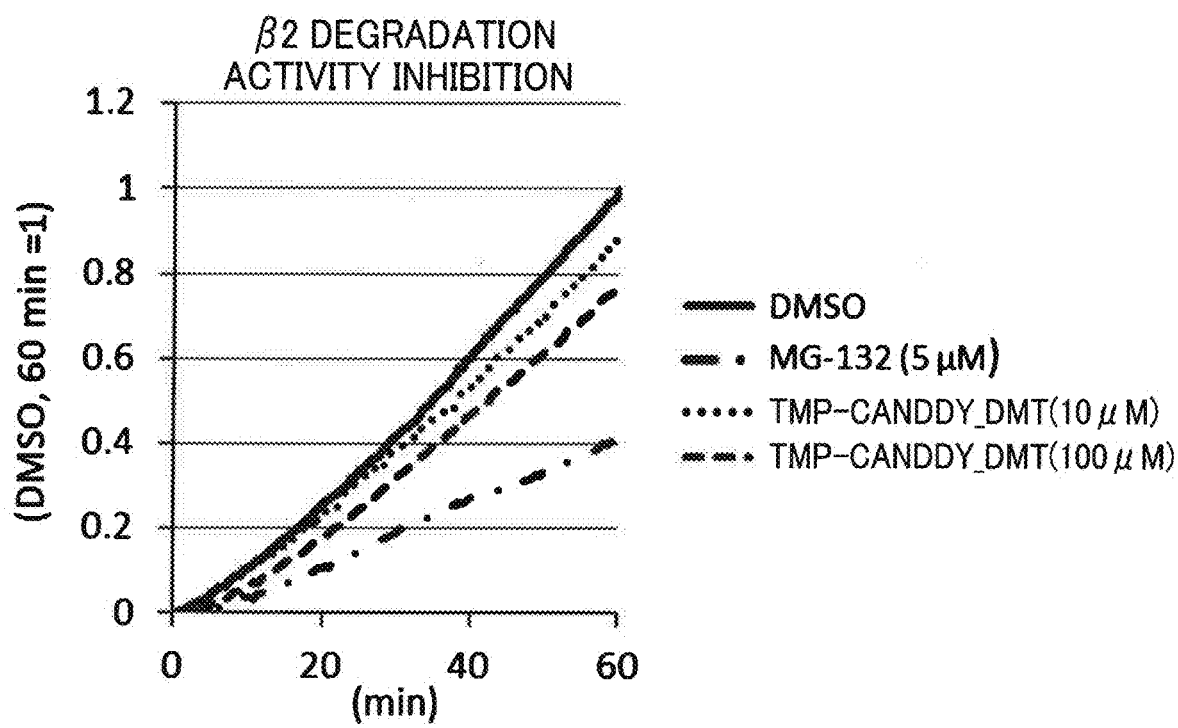
FIG. 10B shows inhibitory activity of TMP-CANDDY_DMT and MG-132 with respect to a catalytic subunit β2 of the proteasome.

FIGS. 10A to 10C show the proteasome activities against β1 (caspase-like activity), β2 (trypsin-like activity), and β5 (chymotrypsin-like activity), respectively. As can be seen in FIGS. 10A to 10C, TMP-CANDDY_DMT was found to have a significantly lower proteasome inhibitory activity as compared with MG-132. Moreover, the inhibitory activity of TMP-CANDDY_DMT was increased in a concentration dependent manner against any of β1, β2, and β5, suggesting that TMP-CANDDY_DMT has a moderate affinity with a proteasome. That is, it was evaluated that DMT has an affinity with a proteasome, and does not inhibit degradation.

Reference Example 3

In Reference Example 3, degradation (knockdown) of a forcibly expressed ecDHFR protein in HeLa cells through TMP-CANDDY_DMT was evaluated by FACS analysis.
(Preparation of Plasmid)
A plasmid (pMIR-DsRed-IRES-ecDHFR-HA-GFP) expressing an ecDHFR protein was amplified in E. coli, and then purified with Miniprep Kit (QIAGEN).
(Introduction of Plasmid into HeLa Cells and Cell Seeding)
As in Example 2, the plasmid was introduced into HeLa cells to transiently overexpress an ecDHFR protein (specifically, a fusion protein of an ecDHFR protein and GFP through a HA tag) or a DsRed protein for comparison in the cells. HeLa cells into which the plasmid had been introduced were seeded in a 24-well plate at a cell density of 6×10$^4$ cells/well, and then cultured under conditions of 37° C. and 5 vol % CO$_2$ for 40 hours.
(Addition of TMP-CANDDY_DMT to HeLa Cells)
Culture was performed for 40 hours after introduction of the plasmid, and then TMP-CANDDY_DMT was added to HeLa cells as follows. As a medium, a serum-free medium (37° C.) in which 1 mass % L-glutamine solution (Sigma-Aldrich) was added to D-MEM (high D-glucose, phenol red, sodium pyruvate (Wako Pure Chemical Industries, Ltd.)) was used, and 297 μL of the medium was added to each well. It is noted that the L-glutamine solution was added immediately before use. A DMSO solution containing TMP-CANDDY_DMT was added to each well at 3 μL/well, and cultured under conditions of 37° C. and 5 vol % CO$_2$. As a control, a TMP-containing DMSO solution or DMSO was used.
(Evaluation of Degradation (Knockdown) of ecDHFR Protein Through TMP-CANDDY_DMT (FACS Analysis))
The medium was removed 24 hours after addition of TMP-CANDDY_DMT, and then PBS was added to wash the cells. After removing PBS, trypsin (0.25 w/v % trypsin-1 mmol/L EDTA•4 Na solution with phenol red) (Wako Pure Chemical Industries, Ltd.) at 37° C. was added to each well at 300 μL/well, and cultured under conditions of 37° C. and 5 vol % CO$_2$ for 1 minute. After culturing, a medium, in which 10 mass % FBS and 1 mass % PenStrep (100 U/mL sodium penicillin G and 100 μg/mL streptomycin sulfate) (Wako Pure Chemical Industries, Ltd.) had been added to D-MEM (low D-glucose, L-glutamine, phenol red) (Wako Pure Chemical Industries, Ltd.), was added to each well at 500 μL/well, and suspended, and then a cell solution was collected in a 15 mL tube.

The cell solution collected was centrifuged (at 1000 rpm×5 minutes, 4° C.), and the supernatant was removed, and then suspended in 2 mL of PBS (37° C.). The cell solution after suspension was centrifuged (at 1000 rpm×5 minutes, 4° C.), and the supernatant was removed, and then 500 μL of an FACS buffer (1 mass % FBS/PBS) at 4° C. was added, and allowed to stand on ice.

A BD FACSCanto™ II (BD Biosciences) was used for flow cytometry, and the expression levels of GFP and the DsRed protein in the cells were quantified. The cell solution was passed through a mesh with a pore size of 32 urn, and transferred to an FACS tube immediately before FACS analysis. The GFP/DsRed ratio per cell was computed using an analysis software FlowJo™ (TOMY Digital Biology Co., Ltd.), and the degradation (knockdown) of the ecDHFR protein by TMP-CANDDY_DMT was determined from a shift in a graph.

Figure 11:
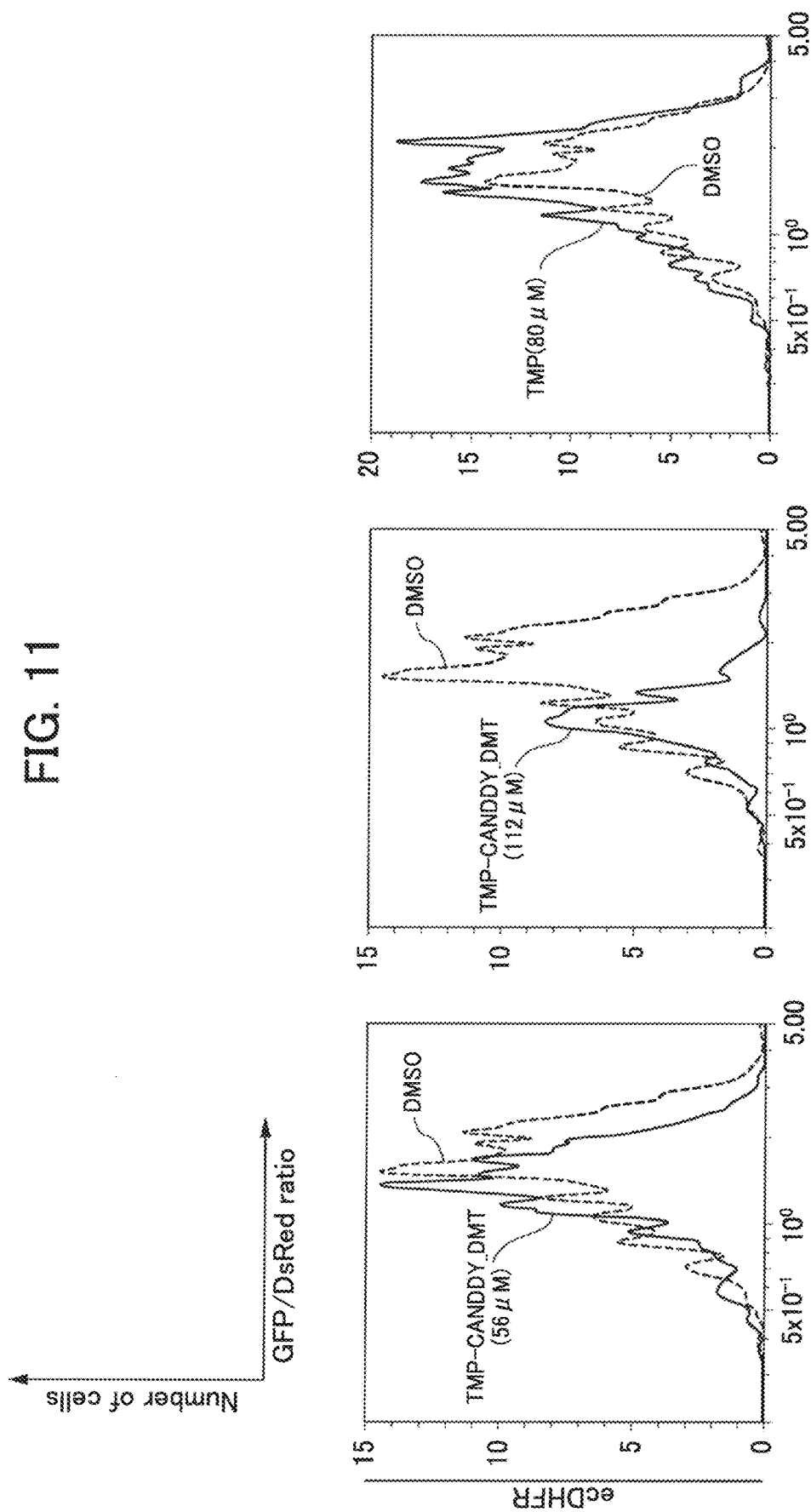
FIG. 11 shows the results of evaluation by FACS analysis of degradation (knockdown) of an ecDHFR protein forcibly expressed in HeLa cells through TMP-CANDDY_DMT.

The results of the FACS analysis are shown in FIG. 11. As shown in FIG. 11, when TMP-CANDDY_DMT was added, the graph is shifted toward the left in a concentration-dependent manner, demonstrating that degradation of the ecDHFR protein was induced by TMP-CANDDY_DMT. On the other hand, when TMP was added, the graph is overlapped to that of the control (DMSO), demonstrating that the ecDHFR protein was not degraded.

Reference Example 4

In Reference Example 4, degradation (knockdown) of a forcibly expressed ecDHFR protein in HeLa cells through TMP-CANDDY_DMT was evaluated by Western blot analysis.
(Preparation of Plasmid)
A plasmid expressing an ecDHFR protein was prepared, as in Reference Example 3.
(Introduction of Plasmid into HeLa Cells and Cell Seeding)
As in Reference Example 3, the plasmid was introduced into HeLa cells to transiently overexpress an ecDHFR protein or a DsRed protein for comparison in the cells. HeLa cells into which the plasmid had been introduced were seeded in a 24-well plate at a cell density of 4×10⁴ cells/well, and then cultured under conditions of 37° C. and 5 vol % $CO_2$ for 40 hours.

(Addition of TMP-CANDDY_DMT to HeLa Cells)

Culture was performed for 40 hours after introduction of the plasmid, and then TMP-CANDDY_DMT was added to HeLa cells as follows. As a medium, a serum-free medium (37° C.) in which 1 mass % L-glutamine solution (Sigma-Aldrich) was added to D-MEM (high D-glucose, phenol red, sodium pyruvate (Wako Pure Chemical Industries, Ltd.)) was used. It is noted that the L-glutamine solution was added immediately before use. A DMSO solution containing TMP-CANDDY_DMT was mixed with the medium so that the concentration of DMSO was 1 vol %, and added to each well at 300 μL/well, and cultured under conditions of 37° C. and 5 vol % $CO_2$. Furthermore, in addition to an experiment group in which a DMSO solution containing TMP-CANDDY_DMT had been added, an experiment group in which a DMSO solution containing both TMP-CANDDY_DMT and bortezomib had been added was prepared. Cycloheximide as a protein synthesis inhibitor was added to the medium so as to give a concentration of 50 μg/mL 12 hours after addition of TMP-CANDDY_DMT. It is noted that as a control, a TMP-containing DMSO solution or DMSO was used.

(Evaluation of Degradation (Knockdown) of ecDHFR Protein Through TMP-CANDDY_DMT (Western Blot Analysis))

The medium was removed 24 hours after addition of TMP-CANDDY_DMT, and PBS was added to wash the cells. After removing PBS, a mixed solution of a cell lysis buffer (CelLytic™ M, Sigma) and a protease inhibitor (cOmplete™ Mini, EDTA-free, Roche) was added to each well at 55 μL/well. After being allowed to stand at 4° C. for 15 minutes, cells were detached with a pipette tip on ice. A cell solution was collected in a 1.5 mL tube, and flash frozen in liquid nitrogen, and then thawed on ice. After repeating this freeze-thaw cycle three times, the solution was centrifuged (at 13000 rpm×20 minutes, 4° C.), and the supernatant (cell extract) was collected.

The cell extract collected was subjected to Western blot analysis. An SDS-PAGE gel was prepared using TGX™ FastCast™ Acrylamide Kit, 12% (Bio-Rad). Electrophoresis samples were prepared in a 6×SDS-PAGE sample buffer (62.5 mM Tris-HCl pH 6.8, 2% SDS, 5% 2-mercaptoethanol, 10% glycerol, 0.25% BPB), and placed on a heat block at 95° C. for 4 minutes. Electrophoresis was performed at 150 V for 50 minutes (electrophoresis buffer; 195 mM glycine, 25 mM Tris).

After electrophoresis, proteins were transferred to a PVDF membrane (Immobion™-P, Millipore) under conditions of 100 V and 40 minutes using a tank-type blotting device and a transfer buffer (25 mM Tris-HCl, 195 mM glycine, 0.01% SDS, 15% methanol). The membrane after transfer was shaken and blocked at room temperature for 30 minutes in 5% skim milk/high-salt TBS-T (100 mM Tris-HCl, 500 mM NaCl, 0.2% Tween-20, pH 7.6). After blocking, the membrane was rinsed with high-salt TBS-T, and an antibody reaction was performed in 1% skim milk/high-salt TBS-T. As the antibody, anti-HA-peroxidase and high-affinity (3F10) rat monoclonal antibody (25 U/mL) (Roche) diluted 1000 times was used. The membrane was shaken at room temperature for 1 hour, and then washed with high-salt TBS-T for 5 minutes. It is noted that washing was performed three times. Further, the membrane was washed with high-salt TBS (100 mM Tris-HCl, 500 mM NaCl, pH 7.6) for 5 minutes. Subsequently, the membrane was treated with a chemiluminescence reagent Immobilon™ Western (Millipore), and then chemiluminescence was detected using a lumino image analyzer LAS-3000 (FUJIFILM Corporation).

Next, a reaction for detecting GAPDH as a control was performed using the same membrane. The membrane was washed with TBS-T (100 mM Tris-HCl, 150 mM NaCl, 0.1% Tween-20, pH 7.6), and blocked by shaking at room temperature for 30 minutes in 5% skim milk/TBS-T. After blocking, a primary antibody reaction was performed in 5% skim milk/TBS-T. As the primary antibody, an anti-GAPDH antibody (6C5, SantaCruz, diluted 20000 times) was used. The membrane was shaken at room temperature for 60 minutes, and then washed with TBS-T for 5 minutes. It is noted that washing was performed three times. After the primary antibody reaction, a secondary antibody reaction was performed in 2% skim milk/TBS-T. As the secondary antibody, anti-mouse IgG (H+L) antibody (A90-116P-33, Bethyl) diluted 20000 times was used. The membrane was shaken at room temperature for 30 minutes, and then washed with TBS-T for 5 minutes. It is noted that washing was performed three times. Further, the membrane was washed with TBS (100 mM Tris-HCl, 150 mM NaCl, pH 7.6) for 5 minutes. Subsequently, the membrane was treated with a chemiluminescence reagent Immobilon™ Western (Millipore), and then chemiluminescence was detected using a lumino image analyzer LAS-3000 (FUJIFILM Corporation). Detected bands were quantified with an image processing software ImageJ (NIH).

Figure 12A:
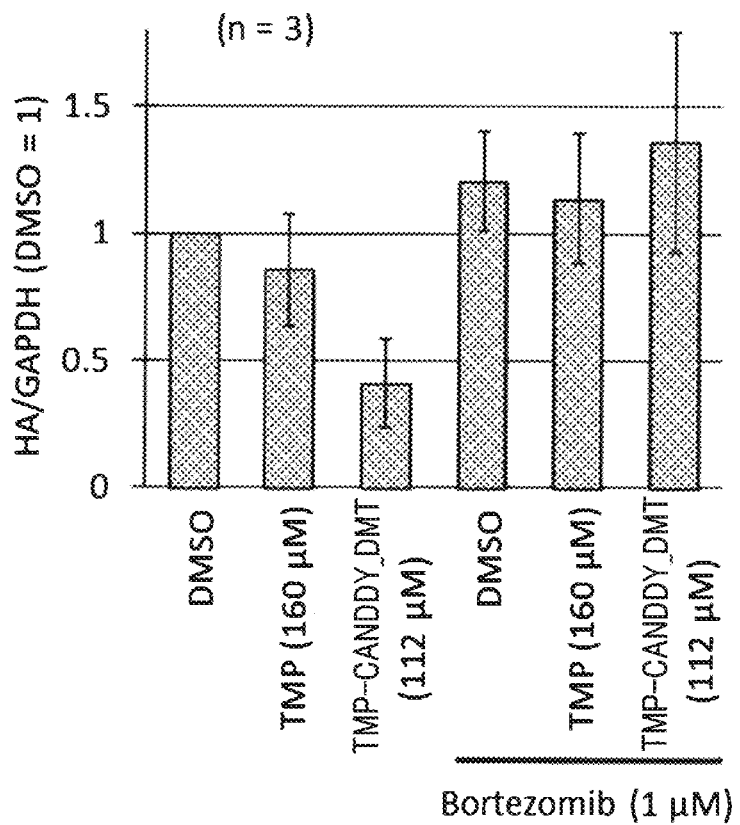
FIG. 12A shows the results of evaluation by Western blot analysis of degradation (knockdown) of an ecDHFR protein forcibly expressed in HeLa cells through TMP-CANDDY_DMT.
Figure 12B:
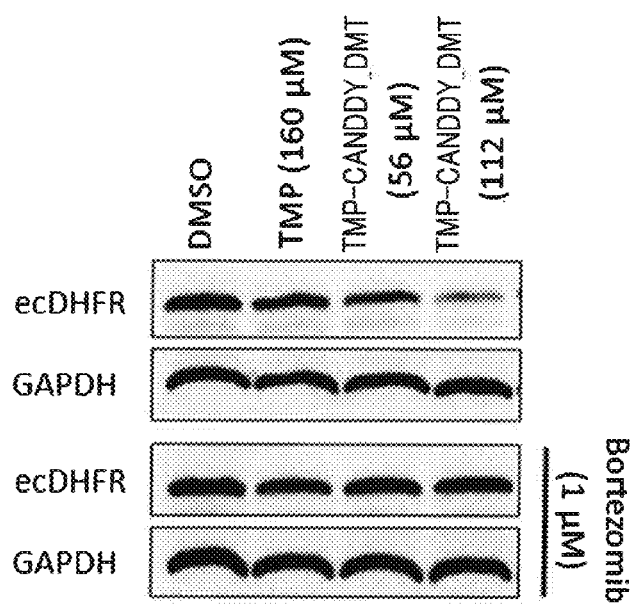
FIG. 12B shows the results of evaluation by Western blot analysis of degradation (knockdown) of an ecDHFR protein forcibly expressed in HeLa cells through TMP-CANDDY_DMT.

The results of the Western blot analysis are shown in FIGS. 12A and 12B. As shown in FIGS. 12A and 12B, when TMP-CANDDY_DMT was added, the amount of the ecDHFR protein was reduced, but when TMP was added, the amount of the ecDHFR protein was not reduced. Furthermore, when both TMP-CANDDY_DMT and bortezomib were added, as compared with the addition of TMP-CANDDY_DMT, degradation of the ecDHFR protein was inhibited. This result supports that TMP-CANDDY_DMT leads the ecDHFR protein to the degradation by a proteasome.

Reference Example 5

In Reference Example 5, a protein affinity molecule and a protein-degradation inducing tag were linked to each other to synthesize TMP-CANDDY_ALLN as a protein-degradation inducing molecule.

As the protein affinity molecule, as in Reference Example 1, TMP-$NH_2$ was used. Furthermore, as the protein-degradation inducing tag, a compound (CANDDY_ALLN) in which an active site (formyl group) of ALLN as a proteasome inhibitor was substituted with a carboxy group was used.

The method of synthesizing TMP-CANDDY_ALLN is described in detail as the following synthesis scheme.

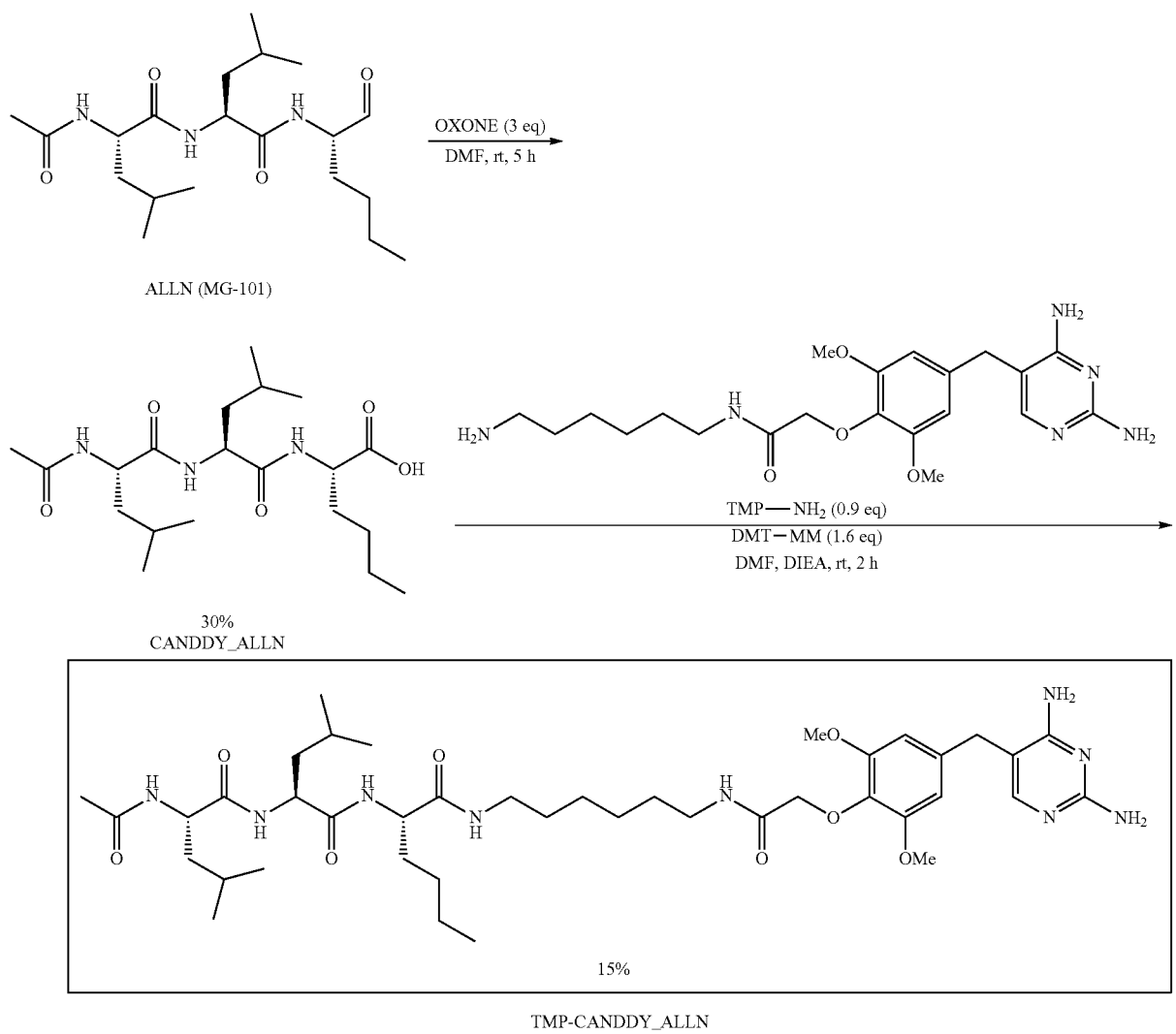

(Synthesis of CANDDY_ALLN)

ALLN (87.2 mg, 0.23 mmol, 1 eq, Code No. 07036-24, Nacalai Tesque, Inc.) was charged into an eggplant flask, and 2 mL of dehydrate DMF was added. After the resultant solution was stirred at room temperature for 5 minutes, Oxone (212.1 mg, 0.69 mmol, 3 eq, Code No. 228036, Sigma-Aldrich) was directly added to a reaction solution, and the reaction solution was stirred at room temperature for 5 hours. The reaction solution was diluted with water, and extracted with chloroform three times. After being dried over anhydrous sodium sulfate, the solvent was evaporated under reduced pressure. Separation and purification treatment was performed by silica gel chromatography (Code No. 30511-35, Nacalai Tesque, Inc.) (chloroform/methanol=20/1 to 10/1, gradient) to obtain CANDDY_ALLN (27.0 mg, 0.068 mmol, 30%).

(Synthesis of TMP-CANDDY_ALLN)

CANDDY_ALLN (26.8 mg, 0.067 mmol, 1 eq) and separately synthesized TMP-NH$_2$ (Long, M. J. et al., Chem. Biol., 2012, 19(5), 629-637) (26.0 mg, 0.060 mmol, 0.9 eq) were charged into an eggplant flask, and 2 mL of dehydrate DMF was added. After the resultant solution was stirred at room temperature for 5 minutes, 0.1 mL of DIPEA was added to neutralize the solution. This was stirred for 5 minutes at room temperature, then DMT-MM (30.0 mg, 0.11 mmol, 1.6 eq, Code No. 329-53751, Wako Pure Chemical Industries, Ltd.) was directly added to a reaction solution, and stirred at room temperature for 2 hours. Under cooling conditions, 10 mL of 10 mass % brine/0.1 N aqueous hydrochloric acid was added, and extracted with ethyl acetate three times. This was washed with 0.5 N aqueous hydrochloric acid and then brine, and then dried over anhydrous sodium sulfate. After evaporating the solvent under reduced pressure, separation and purification treatment was performed by silica gel chromatography (Code No. 30511-35, Nacalai Tesque, Inc.) (chloroform/methanol=10/1) to obtain TMP-CANDDY_ALLN (8.2 mg, 0.010 mmol, 15%, isolated yield).

Reference Example 6

In Reference Example 6, as in Reference Example 2, a proteasome inhibitory activity of TMP-CANDDY_ALLN and an affinity of TMP-CANDDY_ALLN with a proteasome were evaluated.

Figure 13A:
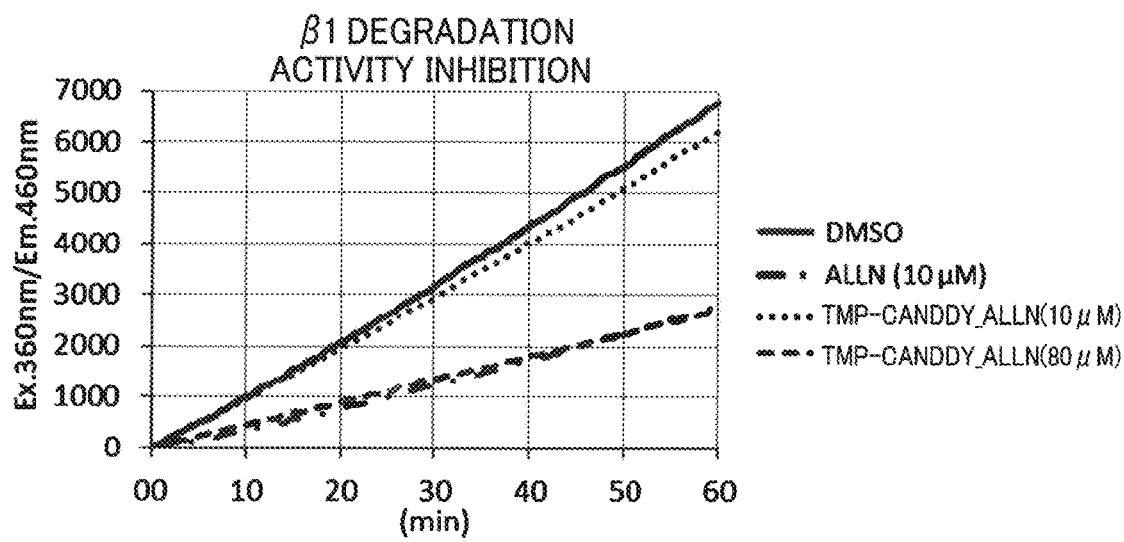
FIG. 13A shows inhibitory activity of TMP-CANDDY_ALLN and ALLN with respect to the catalytic subunit β1 of the proteasome.
Figure 13B:
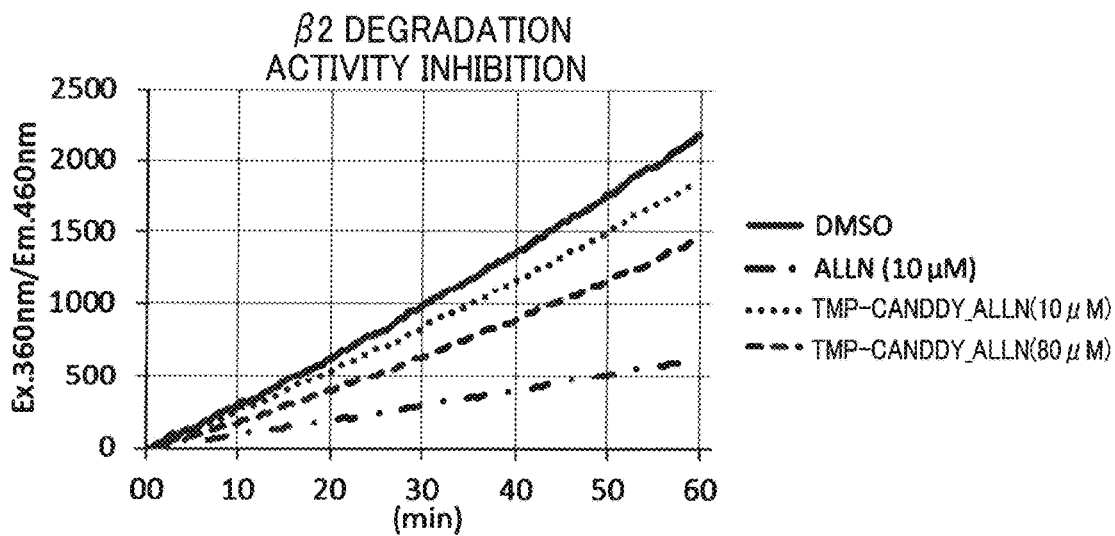
FIG. 13B shows inhibitory activity of TMP-CANDDY_ALLN and ALLN with respect to the catalytic subunit β2 of the proteasome.

FIGS. 13A to 13C show the proteasome activities against β1 (caspase-like activity), β2 (trypsin-like activity), and β5

(chymotrypsin-like activity), respectively. As can be seen in FIGS. 13A to 13C, it was demonstrated that with respect to the activities of β2 and β5, in TMP-CANDDY_ALLN, as compared with single use of ALLN, the inhibitory activity was weakened, and the inhibitory activity of ALLN was inactivated. It was reported that β1 was not inhibited by ALLN (Kaiser, M. et al., Chem. Bio. Chem., 2004, 5, 1256-1266). The result was consistent with this report. Further, the inhibitory activity of TMP-CANDDY_ALLN was found to be increased against any of β1, β2, and β5 in a concentration dependent manner, indicating that TMP-CANDDY_ALLN had an affinity with a proteasome.

Reference Example 7

Figure 14:
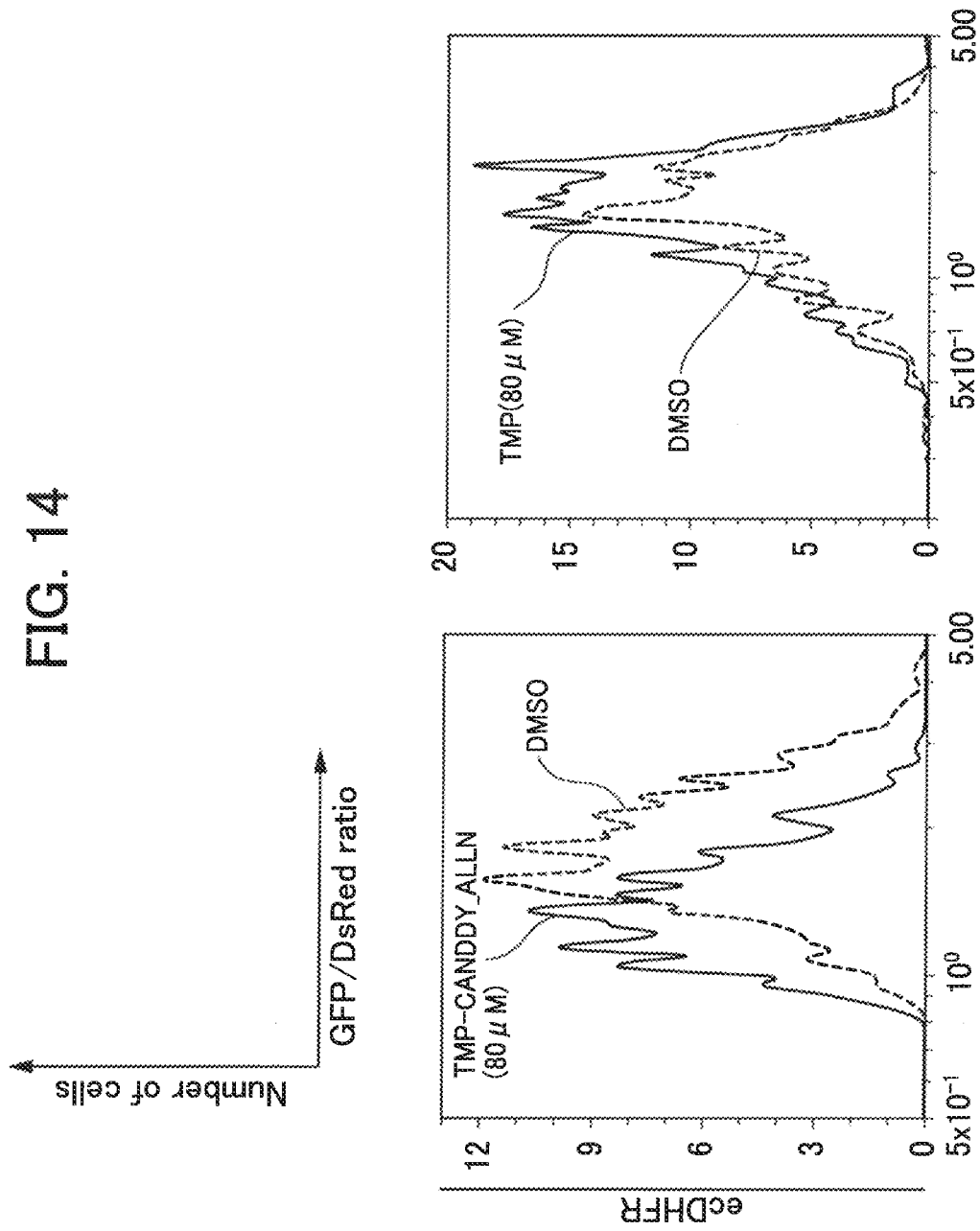
FIG. 14 shows the results of evaluation by FACS analysis of degradation (knockdown) of an ecDHFR protein forcibly expressed in HeLa cells through TMP-CANDDY_ALLN.

In Reference Example 7, degradation (knockdown) of a forcibly expressed ecDHFR protein in HeLa cells through TMP-CANDDY_ALLN was evaluated by FACS analysis.
(Preparation of Plasmid)
A plasmid (pMIR-DsRed-IRES-ecDHFR-HA-GFP) expressing the ecDHFR protein was prepared, as in Reference Example 3.
(Introduction of Plasmid into HeLa Cells and Cell Seeding)
As in Reference Example 3, the plasmid was introduced into HeLa cells to transiently overexpress an ecDHFR protein or a DsRed protein for comparison in the cells. HeLa cells into which the plasmid had been introduced were seeded in a 24-well plate at a cell density of $4\times10^4$ cells/well, and then cultured under conditions of 37° C. and 5 vol % $CO_2$ for 40 hours.
(Addition of TMP-CANDDY_ALLN to HeLa Cells)
Culture was performed for 40 hours after introduction of the plasmid, and then TMP-CANDDY_ALLN was added to HeLa cells as follows. As a medium, a serum-free medium (37° C.) in which 1 mass % L-glutamine solution (Sigma-Aldrich) was added to D-MEM (high D-glucose, phenol red, sodium pyruvate (Wako Pure Chemical Industries, Ltd.)) was used, and added to each well at 300 μL/well. It is noted that the L-glutamine solution was added immediately before use. A DMSO solution containing TMP-CANDDY_ALLN was added to each well at 3 μL/well, and cultured under conditions of 37° C. and 5 vol % $CO_2$. As a control, a TMP-containing DMSO solution or DMSO was used.
(Evaluation of Degradation of Protein (Knockdown) of ecDHFR Protein Through TMP-CANDDY_ALLN (FACS Analysis))
As in Example 2, degradation of the ecDHFR protein through TMP-CANDDY_ALLN was evaluated by FACS analysis.
The results of the FACS analysis are shown in FIG. 14. As shown in FIG. 14, when TMP-CANDDY_ALLN was added, a graph is largely shifted toward the left as compared with the case where the control (DMSO) was added, demonstrating that degradation of the ecDHFR protein was induced by TMP-CANDDY_ALLN. On the other hand, when TMP was added, the graph is overlapped to that of the control (DMSO), demonstrating that the ecDHFR protein was not degraded.

The disclosure of Japanese Patent Application No. 2016-222683 filed on Nov. 15, 2016 is entirely incorporated herein by reference. All documents, patent applications, and technical standards cited herein are incorporated herein by reference to the same extent as if each of the documents, patent applications, and technical standards was specifically and individually indicated to be incorporated by reference.

The invention claimed is:

1. A Ras protein-degradation inducing molecule, wherein the Ras protein-degradation inducing molecule is a conjugate of a Ras protein affinity molecule that has an affinity with a Ras protein, and a protein-degradation inducing tag that has an affinity with a 26S proteasome and does not inhibit degradation of a protein by the 26S proteasome, with the proviso that the conjugate excludes a fusion protein; and the Ras protein-degradation inducing molecule is capable of inducing degradation of the Ras protein.

2. The Ras protein-degradation inducing molecule according to claim 1, wherein the Ras protein-degradation inducing molecule is capable of inducing degradation of the Ras protein in a ubiquitin-independent manner.

3. The Ras protein-degradation inducing molecule according to claim 1, wherein the protein-degradation inducing tag has a structure represented by the following formula (I), or has a structure where a 26S proteasome inhibitory activity of a 26S proteasome inhibitor is inactivated, or has a structure of a proteasome activator:

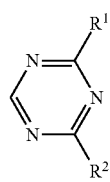

(I)

wherein in the formula (I), $R^1$ and $R^2$ each independently represent a hydrocarbon group having 1 to 20 carbon atoms, an alkoxy group having 1 to 20 carbon atoms, an aryloxy group having 6 to 20 carbon atoms, a hydroxy group, a carboxy group, an amino group, or a halogen group.

4. The Ras protein-degradation inducing molecule according to claim 3, wherein the proteasome inhibitory activity is an inhibitory activity against at least one selected from the group consisting of a caspase-like activity, a trypsin-like activity, and a chymotrypsin-like activity.

5. A pharmaceutical composition comprising the Ras protein-degradation inducing molecule according to claim 1.

6. The pharmaceutical composition according to claim 5, wherein the pharmaceutical composition is used for preventing or treating a Ras protein-mediated disease or condition.

7. The pharmaceutical composition according to claim 6, wherein the Ras protein-mediated disease or condition is a cancer, an immune disease, an infection, a neurological disease, a RAS/MAPK syndrome, cirrhosis, chronic hepatitis, or a memory impairment.

8. The pharmaceutical composition according to claim 7, wherein the Ras protein-mediated disease or condition is a cancer.

9. The Ras protein-degradation inducing molecule according to claim 1, wherein the Ras protein-degradation inducing molecule is represented by the following formula:

175 176
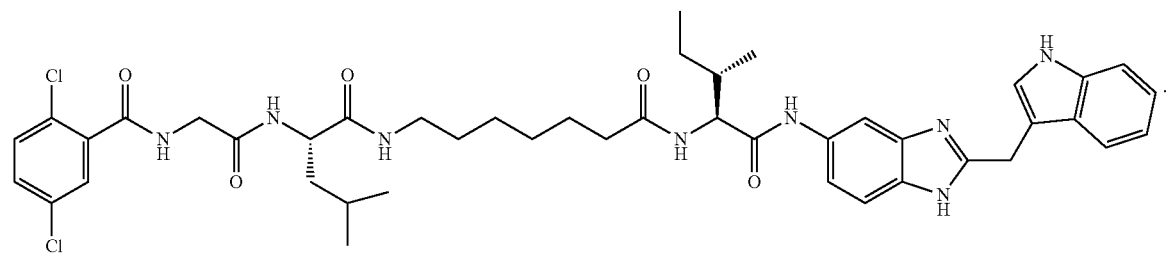 [SMILES: CC[C@H](C)[C@H](NC(=O)CCCCCCNC(=O)[C@H](CC(C)C)NC(=O)CNC(=O)c1cc(Cl)ccc1Cl)C(=O)Nc1ccc2[nH]c(Cc3c[nH]c4ccccc34)nc2c1]
\* \* \* \* \*

SEQUENCE LISTING

```
<160> NUMBER OF SEQ ID NOS: 6

<210> SEQ ID NO 1
<211> LENGTH: 49
<212> TYPE: DNA
<213> ORGANISM: Artificial Sequence
<220> FEATURE:
<223> OTHER INFORMATION: Forward primer for RF cloning

<400> SEQUENCE: 1
cacgatgata atatggccac aaccatgact gaatataaac ttgtggtag              49

<210> SEQ ID NO 2
<211> LENGTH: 47
<212> TYPE: DNA
<213> ORGANISM: Artificial Sequence
<220> FEATURE:
<223> OTHER INFORMATION: Reverse primer for RF cloning

<400> SEQUENCE: 2
gaacgtcgta cgggtaatcg atcataatta cacactttgt ctttgac                47

<210> SEQ ID NO 3
<211> LENGTH: 26
<212> TYPE: DNA
<213> ORGANISM: Artificial Sequence
<220> FEATURE:
<223> OTHER INFORMATION: Forward primer for site-directed mutagenesis
      (G12D) of K-ras gene

<400> SEQUENCE: 3
```

```
ggagctgatg gcgtaggcaa gagtgc                                  26

<210> SEQ ID NO 4
<211> LENGTH: 27
<212> TYPE: DNA
<213> ORGANISM: Artificial Sequence
<220> FEATURE:
<223> OTHER INFORMATION: Reverse primer for site-directed mutagenesis
      (G12D) of K-ras gene

<400> SEQUENCE: 4
tacgccatca gctccaacta ccacaag                                 27

<210> SEQ ID NO 5
<211> LENGTH: 26
<212> TYPE: DNA
<213> ORGANISM: Artificial Sequence
<220> FEATURE:
<223> OTHER INFORMATION: Forward primer for site-directed mutagenesis
      (G12V) of K-ras gene

<400> SEQUENCE: 5
ggagctgttg gcgtaggcaa gagtgc                                  26

<210> SEQ ID NO 6
<211> LENGTH: 27
<212> TYPE: DNA
<213> ORGANISM: Artificial Sequence
<220> FEATURE:
<223> OTHER INFORMATION: Reverse primer for site-directed mutagenesis
      (G12V) of K-ras gene

<400> SEQUENCE: 6
tacgccaaca gctccaacta ccacaag                                 27
```